United States Patent
Drake et al.

(10) Patent No.: US 10,874,850 B2
(45) Date of Patent: Dec. 29, 2020

(54) IMPEDANCE-BASED VERIFICATION FOR DELIVERY OF IMPLANTABLE MEDICAL DEVICES

(71) Applicant: Medtronic, Inc., Minneapolis, MN (US)

(72) Inventors: Ronald A. Drake, St. Louis Park, MN (US); Kathryn Hilpisch, Cottage Grove, MN (US); Kevin R. Seifert, Forest Lake, MN (US); William Schindeldecker, Foreston, MN (US); Stephanie Koppes, Coon Rapids, MN (US); Brian P. Colin, Shakopee, MN (US); Alexander R. Mattson, St. Paul, MN (US)

(73) Assignee: MEDTRONIC, INC., Minneapolis, MN (US)

(*) Notice: Subject to any disclaimer, the term of this patent is extended or adjusted under 35 U.S.C. 154(b) by 57 days.

(21) Appl. No.: 16/146,391

(22) Filed: Sep. 28, 2018

(65) Prior Publication Data
US 2020/0101279 A1    Apr. 2, 2020

(51) Int. Cl.
*A61N 1/05* (2006.01)
*A61N 1/08* (2006.01)
*A61N 1/37* (2006.01)

(52) U.S. Cl.
CPC ............ *A61N 1/057* (2013.01); *A61N 1/059* (2013.01); *A61N 1/08* (2013.01); *A61N 1/37* (2013.01); *A61N 2001/083* (2013.01)

(58) Field of Classification Search
CPC .......... A61N 1/057; A61N 1/059; A61N 1/08; A61N 1/37
See application file for complete search history.

(56) References Cited

U.S. PATENT DOCUMENTS 4,035,909 A   7/1977   Dey
4,103,690 A   8/1978   Harris
(Continued)

FOREIGN PATENT DOCUMENTS

EP            3192559        7/2017
WO       WO 00/59376 A1    10/2000
(Continued)

OTHER PUBLICATIONS

Rozenman et al., "Wireless Acoustic Communication with a Miniature Pressure Sensor in the Pulmonary Artery for Disease Surveillance and Therapy of Patients With Congestive Heart Failure," J Am Coli Cardiol Feb. 2007; vol. 49, No. 7 pp. 784-790.
(Continued)

*Primary Examiner* — Joseph M Dietrich
(74) *Attorney, Agent, or Firm* — Shumaker & Sieffert, P.A.

(57) ABSTRACT

A device for delivering an implantable medical device (IMD) includes an elongated member and a deployment bay configured to house the IMD, the deployment bay defining a distal opening for deploying the IMD out of the deployment bay. The device includes a first electrode located inside the deployment bay during intravascular navigation, a second electrode, and impedance detection circuitry configured to deliver an electrical signal to a path between the first electrode and the second electrode through at least one of a fluid or tissue of the patient. The device also includes processing circuitry configured to determine an impedance of the path based on the signal and control a user interface to indicate when an impedance of the path indicates that at least one of the IMD or the distal opening is in a fixation configuration relative to the target site of the patient.

28 Claims, 15 Drawing Sheets

(56) References Cited

U.S. PATENT DOCUMENTS

| | | |
|---|---|---|
| 4,112,952 A | 9/1978 | Thomas et al. |
| 4,376,811 A | 3/1983 | Goebel |
| 4,494,531 A | 1/1985 | Gianturco |
| 4,727,873 A | 3/1988 | Mabin-Uddin |
| 4,731,305 A | 5/1988 | Goebel et al. |
| 5,002,067 A | 3/1991 | Berthelsen |
| 5,024,239 A | 6/1991 | Rosenstein |
| 5,098,393 A | 3/1992 | Amplatz et al. |
| 5,249,574 A | 10/1993 | Bush et al. |
| 5,255,678 A | 10/1993 | Deslauriers et al. |
| 5,255,679 A | 10/1993 | Imran |
| 5,265,608 A | 11/1993 | Lee et al. |
| 5,282,845 A | 2/1994 | Bush et al. |
| 5,306,581 A | 4/1994 | Taylor et al. |
| 5,314,462 A | 5/1994 | Heil, Jr. et al. |
| 5,324,316 A | 6/1994 | Schulman et al. |
| 5,358,514 A | 10/1994 | Schulman et al. |
| 5,383,922 A | 1/1995 | Zipes et al. |
| 5,387,233 A | 2/1995 | Alferness et al. |
| 5,492,119 A | 2/1996 | Abrams |
| 5,540,734 A | 7/1996 | Zabara |
| 5,545,219 A | 8/1996 | Kuzma |
| 5,562,723 A | 10/1996 | Rugland et al. |
| 5,766,234 A | 6/1998 | Chen et al. |
| 5,776,632 A | 7/1998 | Honegger |
| 5,814,089 A | 9/1998 | Stokes et al. |
| 5,824,041 A | 10/1998 | Lenker et al. |
| 5,840,076 A | 11/1998 | Swanson et al. |
| 5,860,974 A | 1/1999 | Abele |
| 5,895,391 A | 4/1999 | Farnholtz |
| 5,897,584 A | 4/1999 | Herman |
| 5,968,052 A | 10/1999 | Sullivan et al. |
| 5,984,944 A | 11/1999 | Forber |
| 6,024,752 A | 2/2000 | Horn et al. |
| 6,074,401 A | 6/2000 | Gardiner et al. |
| 6,113,593 A | 9/2000 | Tu et al. |
| 6,120,480 A | 9/2000 | Zhang et al. |
| 6,136,005 A | 10/2000 | Goode et al. |
| 6,149,658 A | 11/2000 | Gardiner et al. |
| 6,183,305 B1 | 2/2001 | Doan et al. |
| 6,238,813 B1 | 5/2001 | Maile et al. |
| 6,258,098 B1 | 7/2001 | Taylor et al. |
| 6,266,568 B1 | 7/2001 | Mann et al. |
| 6,270,489 B1 | 8/2001 | Wise et al. |
| 6,308,105 B1 | 10/2001 | Duysens et al. |
| 6,322,586 B1 | 11/2001 | Monroe et al. |
| 6,350,278 B1 | 2/2002 | Lenker et al. |
| 6,352,561 B1 | 3/2002 | Leopold et al. |
| 6,395,017 B1 | 5/2002 | Dwyer et al. |
| 6,434,431 B1 | 8/2002 | Camps et al. |
| 6,468,301 B1 | 10/2002 | Amplatz et al. |
| 6,477,423 B1 | 11/2002 | Jenkins |
| 6,498,951 B1 | 12/2002 | Larson et al. |
| 6,505,075 B1 | 1/2003 | Weiner |
| 6,510,332 B1 | 1/2003 | Greenstein |
| 6,514,265 B2 | 2/2003 | Ho et al. |
| 6,514,280 B1 | 2/2003 | Gilson |
| 6,529,777 B1 | 3/2003 | Holmstrom et al. |
| 6,551,332 B1 | 4/2003 | Nguyen et al. |
| 6,582,400 B1 | 6/2003 | Hawk et al. |
| 6,585,634 B1 | 7/2003 | Henckel et al. |
| 6,589,238 B2 | 7/2003 | Edwards et al. |
| 6,600,955 B1 | 7/2003 | Zierhofer |
| 6,607,541 B1 | 8/2003 | Gardiner et al. |
| 6,607,843 B2 | 8/2003 | Ruth, II et al. |
| 6,613,059 B2 | 9/2003 | Schaller et al. |
| 6,623,518 B2 | 9/2003 | Thompson et al. |
| 6,626,916 B1 | 9/2003 | Yeung et al. |
| 6,641,593 B1 | 11/2003 | Schaller et al. |
| 6,645,143 B2 | 11/2003 | VanTassel et al. |
| 6,679,902 B1 | 1/2004 | Boyle et al. |
| 6,689,056 B1 | 2/2004 | Kilcoyne et al. |
| 6,695,859 B1 | 2/2004 | Golden et al. |
| 6,840,956 B1 | 1/2005 | Wolinsky et al. |
| 6,866,650 B2 | 3/2005 | Stevens et al. |
| 6,876,885 B2 | 4/2005 | Swoyer et al. |
| 6,889,093 B1 | 5/2005 | Flammang |
| 6,895,283 B2 | 5/2005 | Erickson et al. |
| 6,913,607 B2 | 7/2005 | Ainsworth et al. |
| 6,918,917 B1 | 7/2005 | Nguyen et al. |
| 6,921,407 B2 | 7/2005 | Nguyen et al. |
| 6,926,730 B1 | 8/2005 | Nguyen et al. |
| 6,932,837 B2 | 8/2005 | Amplatz et al. |
| 6,960,221 B2 | 11/2005 | Ho et al. |
| 7,047,084 B2 | 5/2006 | Erickson et al. |
| 7,054,692 B1 | 5/2006 | Whitehurst et al. |
| 7,060,038 B2 | 6/2006 | Letort et al. |
| 7,070,881 B2 | 7/2006 | Kishiyama et al. |
| 7,072,703 B2 | 7/2006 | Zhang et al. |
| 7,099,718 B1 | 8/2006 | Thacker et al. |
| 7,128,765 B2 | 10/2006 | Paulot et al. |
| 7,147,604 B1 | 12/2006 | Allen et al. |
| 7,172,620 B2 | 2/2007 | Gilson |
| 7,177,702 B2 | 2/2007 | Wallace et al. |
| 7,181,288 B1 | 2/2007 | Rezai et al. |
| 7,236,821 B2 | 6/2007 | Cates et al. |
| 7,288,096 B2 | 10/2007 | Chin |
| 7,291,186 B2 | 11/2007 | Zhang |
| 7,294,334 B1 | 11/2007 | Michal et al. |
| 7,309,349 B2 | 12/2007 | Jackson et al. |
| 7,364,541 B2 | 4/2008 | Chu et al. |
| 7,410,512 B2 | 8/2008 | Tsukamoto et al. |
| 7,473,266 B2 | 1/2009 | Glaser et al. |
| 7,499,758 B2 | 3/2009 | Cates et al. |
| 7,572,228 B2 | 8/2009 | Wolinsky et al. |
| 7,699,059 B2 | 4/2010 | Fonseca et al. |
| 7,704,245 B2 | 4/2010 | Dittman et al. |
| 7,717,854 B2 | 5/2010 | Mann et al. |
| 7,740,655 B2 | 6/2010 | Birdsall |
| 7,765,014 B2 | 7/2010 | Eversull et al. |
| 7,769,420 B2 | 8/2010 | Silver et al. |
| 7,776,080 B2 | 8/2010 | Bei et al. |
| 7,783,338 B2 | 8/2010 | Ainsworth et al. |
| 7,785,360 B2 | 8/2010 | Freitag |
| 7,797,053 B2 | 9/2010 | Atkinson et al. |
| 7,801,626 B2 | 9/2010 | Moser |
| 7,871,430 B2 | 1/2011 | Pavcnik et al. |
| 7,963,952 B2 | 6/2011 | Wright et al. |
| 8,062,327 B2 | 11/2011 | Chaduszko et al. |
| 8,352,028 B2 | 1/2013 | Wenger |
| 8,532,790 B2 | 9/2013 | Griswold |
| 8,715,332 B2 | 5/2014 | Tan et al. |
| 9,186,501 B2 | 11/2015 | Brijmohansigngh et al. |
| 9,775,982 B2 | 10/2017 | Grubac et al. |
| 9,844,659 B2 | 12/2017 | Grubac et al. |
| 10,052,127 B2 | 8/2018 | Wood |
| 10,071,243 B2 | 9/2018 | Kuhn et al. |
| 10,080,888 B2 | 9/2018 | Kelly et al. |
| 10,099,050 B2 | 10/2018 | Chen et al. |
| 10,112,045 B2 | 10/2018 | Anderson et al. |
| 10,118,026 B2 | 11/2018 | Grubac et al. |
| 10,173,050 B2 | 1/2019 | Grubac et al. |
| 2001/0002300 A1 | 5/2001 | Tinker et al. |
| 2001/0047181 A1 | 11/2001 | Ho et al. |
| 2002/0010490 A1 | 1/2002 | Schaller et al. |
| 2002/0082610 A1 | 6/2002 | Cioanta et al. |
| 2002/0103521 A1 | 8/2002 | Swoyer et al. |
| 2002/0111659 A1 | 8/2002 | Davis et al. |
| 2002/0120250 A1 | 8/2002 | Altman |
| 2002/0147485 A1 | 10/2002 | Mamo et al. |
| 2002/0156513 A1 | 10/2002 | Borkan |
| 2002/0195872 A1 | 12/2002 | Weiner |
| 2003/0004537 A1 | 1/2003 | Boyle et al. |
| 2003/0036790 A1 | 2/2003 | Corbett, III et al. |
| 2003/0045901 A1 | 3/2003 | Opolski |
| 2003/0069623 A1 | 4/2003 | Stypulkowski |
| 2003/0078603 A1 | 4/2003 | Schaller et al. |
| 2003/0088301 A1 | 5/2003 | King |
| 2003/0093118 A1 | 5/2003 | Ho et al. |
| 2003/0093130 A1 | 5/2003 | Stypulkowski |
| 2003/0120328 A1 | 6/2003 | Jenkins et al. |
| 2003/0199974 A1 | 10/2003 | Lee et al. |
| 2003/0236545 A1 | 12/2003 | Gilson |
| 2004/0059393 A1 | 3/2004 | Policker et al. |

(56) References Cited

U.S. PATENT DOCUMENTS

| | | |
|---|---|---|
| 2004/0093053 A1 | 5/2004 | Gelber et al. |
| 2004/0101746 A1 | 5/2004 | Ota et al. |
| 2004/0102797 A1 | 5/2004 | Golden et al. |
| 2004/0111099 A1 | 6/2004 | Nguyen et al. |
| 2004/0111139 A1 | 6/2004 | McCreery |
| 2004/0116878 A1 | 6/2004 | Byrd et al. |
| 2004/0116992 A1 | 6/2004 | Wardle et al. |
| 2004/0148007 A1 | 7/2004 | Jackson et al. |
| 2004/0176782 A1 | 9/2004 | Hanse et al. |
| 2004/0181206 A1 | 9/2004 | Chin et al. |
| 2004/0185337 A1 | 9/2004 | Ishizaki |
| 2004/0193229 A1 | 9/2004 | Starkebaum et al. |
| 2004/0215230 A1 | 10/2004 | Frazier et al. |
| 2004/0230279 A1 | 11/2004 | Cates et al. |
| 2004/0243206 A1 | 12/2004 | Tadlock |
| 2004/0249433 A1 | 12/2004 | Freitag |
| 2005/0015129 A1 | 1/2005 | Mische |
| 2005/0021054 A1 | 1/2005 | Ainsworth et al. |
| 2005/0060014 A1 | 3/2005 | Swoyer et al. |
| 2005/0065601 A1 | 3/2005 | Lee et al. |
| 2005/0070924 A1 | 3/2005 | Schaller et al. |
| 2005/0090884 A1 | 4/2005 | Honeck |
| 2005/0096718 A1 | 5/2005 | Gerber et al. |
| 2005/0102006 A1 | 5/2005 | Whitehurst et al. |
| 2005/0107861 A1 | 5/2005 | Harris et al. |
| 2005/0107862 A1 | 5/2005 | Ohlenschlaeger |
| 2005/0149141 A1 | 7/2005 | Starkebaum |
| 2005/0149142 A1 | 7/2005 | Starkebaum |
| 2005/0154321 A1 | 7/2005 | Wolinsky et al. |
| 2005/0171479 A1 | 8/2005 | Hruska et al. |
| 2005/0209653 A1 | 9/2005 | Herbert et al. |
| 2005/0221054 A1 | 10/2005 | Kawano et al. |
| 2005/0222632 A1 | 10/2005 | Obino |
| 2005/0245840 A1 | 11/2005 | Christopherson et al. |
| 2005/0245986 A1 | 11/2005 | Starkebaum |
| 2005/0246004 A1 | 11/2005 | Cameron et al. |
| 2005/0267487 A1 | 12/2005 | Christensen et al. |
| 2005/0287859 A1 | 12/2005 | Komizo et al. |
| 2005/0288596 A1 | 12/2005 | Eigler et al. |
| 2006/0047205 A1 | 3/2006 | Ludomirsky et al. |
| 2006/0057458 A1 | 3/2006 | O'Dea et al. |
| 2006/0069422 A9 | 3/2006 | Bolduc et al. |
| 2006/0079943 A1 | 4/2006 | Narciso, Jr. |
| 2006/0079950 A1 | 4/2006 | Lehnhardt et al. |
| 2006/0085041 A1 | 4/2006 | Hastings et al. |
| 2006/0085042 A1 | 4/2006 | Hastings et al. |
| 2006/0085971 A1 | 4/2006 | Andrevvs et al. |
| 2006/0099238 A1 | 5/2006 | Khosravi et al. |
| 2006/0100686 A1 | 5/2006 | Bolduc et al. |
| 2006/0149324 A1 | 7/2006 | Mann et al. |
| 2006/0149330 A1 | 7/2006 | Mann et al. |
| 2006/0206163 A1 | 9/2006 | Wahlstrand et al. |
| 2006/0206165 A1 | 9/2006 | Jaax et al. |
| 2006/0206166 A1 | 9/2006 | Weiner |
| 2006/0212096 A1 | 9/2006 | Stevenson |
| 2006/0222942 A1 | 10/2006 | Zhao et al. |
| 2006/0241733 A1 | 10/2006 | Zhang et al. |
| 2006/0259128 A1 | 11/2006 | Pavcnik et al. |
| 2006/0271137 A1 | 11/2006 | Stanton-Hicks |
| 2006/0275659 A1 | 12/2006 | Kim et al. |
| 2007/0027514 A1 | 2/2007 | Gerber |
| 2007/0027515 A1 | 2/2007 | Gerber |
| 2007/0043414 A1 | 2/2007 | Fifer et al. |
| 2007/0043424 A1 | 2/2007 | Pryor |
| 2007/0073391 A1 | 3/2007 | Bourang et al. |
| 2007/0088230 A1 | 4/2007 | Terashi et al. |
| 2007/0088396 A1 | 4/2007 | Jacobson |
| 2007/0088418 A1 | 4/2007 | Jacobson |
| 2007/0129637 A1 | 6/2007 | Wolinksy et al. |
| 2007/0135826 A1 | 6/2007 | Zaver et al. |
| 2007/0150020 A1 | 6/2007 | Hokanson et al. |
| 2007/0154801 A1 | 7/2007 | Hyung et al. |
| 2007/0156126 A1 | 7/2007 | Flaherty |
| 2007/0179552 A1 | 8/2007 | Dennis et al. |
| 2007/0197939 A1 | 8/2007 | Wallace et al. |
| 2007/0219590 A1 | 9/2007 | Hastings et al. |
| 2007/0247786 A1 | 10/2007 | Aamodt et al. |
| 2007/0255295 A1 | 11/2007 | Starkebaum et al. |
| 2007/0255383 A1 | 11/2007 | Gelber et al. |
| 2007/0274565 A1 | 11/2007 | Penner et al. |
| 2007/0276461 A1 | 11/2007 | Andreas et al. |
| 2007/0293090 A1 | 12/2007 | Cowan et al. |
| 2007/0293909 A1 | 12/2007 | Cowan et al. |
| 2007/0293922 A1 | 12/2007 | Soltis et al. |
| 2007/0299498 A1 | 12/2007 | Perez et al. |
| 2008/0009750 A1 | 1/2008 | Aeby et al. |
| 2008/0051704 A1 | 2/2008 | Patel et al. |
| 2008/0071178 A1 | 3/2008 | Greenland et al. |
| 2008/0077227 A1 | 3/2008 | Ouellete et al. |
| 2008/0103578 A1 | 5/2008 | Gerber |
| 2008/0125844 A1 | 5/2008 | Swoyer et al. |
| 2008/0132981 A1 | 6/2008 | Gerber |
| 2008/0132982 A1 | 6/2008 | Gerber |
| 2008/0148554 A1 | 6/2008 | Merrill et al. |
| 2008/0172118 A1 | 7/2008 | Johnson et al. |
| 2008/0255475 A1 | 10/2008 | Kondrosky et al. |
| 2008/0262422 A1 | 10/2008 | Cahill |
| 2008/0269710 A1 | 10/2008 | Bonde et al. |
| 2008/0275350 A1 | 11/2008 | Liao et al. |
| 2008/0283066 A1 | 11/2008 | Delgado et al. |
| 2008/0300672 A1 | 12/2008 | Kassab et al. |
| 2009/0043367 A1 | 2/2009 | Zilberman et al. |
| 2009/0082828 A1 | 3/2009 | Ostroff |
| 2009/0082843 A1 | 3/2009 | Cox et al. |
| 2009/0099641 A1 | 4/2009 | Wu et al. |
| 2009/0105799 A1 | 4/2009 | Hekmat et al. |
| 2009/0131970 A1 | 5/2009 | Chanduszko et al. |
| 2009/0157092 A1 | 6/2009 | Blumenkranz et al. |
| 2009/0163969 A1 | 6/2009 | Donofrio |
| 2009/0177095 A1 | 7/2009 | Aeby et al. |
| 2009/0182412 A1 | 7/2009 | Tan et al. |
| 2009/0192514 A1 | 7/2009 | Feinberg et al. |
| 2009/0192585 A1 | 7/2009 | Bloom et al. |
| 2009/0192601 A1 | 7/2009 | Rafiee et al. |
| 2009/0234367 A1 | 9/2009 | Verma |
| 2009/0270741 A1 | 10/2009 | Vanney et al. |
| 2009/0275818 A1 | 11/2009 | Rau et al. |
| 2009/0299429 A1 | 12/2009 | Mayotte |
| 2009/0306539 A1 | 12/2009 | Woodruff et al. |
| 2009/0326346 A1 | 12/2009 | Kracker et al. |
| 2010/0004730 A1 | 1/2010 | Benjamin et al. |
| 2010/0030063 A1 | 2/2010 | Lee et al. |
| 2010/0030139 A1 | 2/2010 | Copa |
| 2010/0057009 A1 | 3/2010 | McQueen et al. |
| 2010/0063478 A1 | 3/2010 | Selkee |
| 2010/0076398 A1 | 3/2010 | Scheurer et al. |
| 2010/0082087 A1 | 4/2010 | Silipo et al. |
| 2010/0094400 A1 | 4/2010 | Bolduc et al. |
| 2010/0168612 A1 | 7/2010 | Ducharme et al. |
| 2010/0179561 A1 | 7/2010 | Pilarski et al. |
| 2010/0185172 A1 | 7/2010 | Fabro |
| 2010/0234698 A1 | 9/2010 | Manstrom et al. |
| 2010/0274221 A1 | 10/2010 | Sigg et al. |
| 2010/0274227 A1 | 10/2010 | Khairkhahan et al. |
| 2010/0274345 A1 | 10/2010 | Rust |
| 2010/0304209 A1 | 12/2010 | Lund et al. |
| 2010/0305653 A1 | 12/2010 | Lund et al. |
| 2011/0160557 A1 | 6/2011 | Cinbis et al. |
| 2011/0190842 A1 | 8/2011 | Johnson et al. |
| 2011/0220274 A1 | 9/2011 | Erskine |
| 2011/0251662 A1 | 10/2011 | Griswold et al. |
| 2011/0264194 A1 | 10/2011 | Griswold |
| 2011/0270339 A1 | 11/2011 | Murray, III et al. |
| 2011/0313503 A1 | 12/2011 | Berra et al. |
| 2012/0029598 A1 | 2/2012 | Zhao |
| 2012/0172690 A1 | 7/2012 | Anderson et al. |
| 2012/0172691 A1 | 7/2012 | Brauker et al. |
| 2012/0172891 A1 | 7/2012 | Lee |
| 2012/0172892 A1 | 7/2012 | Grubac et al. |
| 2013/0253309 A1 | 9/2013 | Allan et al. |
| 2013/0253346 A1 | 9/2013 | Griswold et al. |
| 2014/0275991 A1 | 9/2014 | Potter et al. |
| 2015/0045868 A1 | 2/2015 | Boner et al. |
| 2016/0310747 A1 | 10/2016 | Grubac et al. |

(56) References Cited

U.S. PATENT DOCUMENTS

| | | |
|---|---|---|
| 2017/0095662 A1 | 4/2017 | McDonnell et al. |
| 2017/0224997 A1 | 8/2017 | Shuros et al. |
| 2018/0028805 A1 | 2/2018 | Anderson et al. |
| 2018/0318591 A1 | 11/2018 | Kabe et al. |
| 2019/0009078 A1 | 1/2019 | Kuhn et al. |

FOREIGN PATENT DOCUMENTS

| | | |
|---|---|---|
| WO | WO 200166151 A1 | 9/2001 |
| WO | WO 02/30295 A1 | 4/2002 |
| WO | WO 03/084398 A1 | 10/2003 |
| WO | WO 2004014456 A2 | 2/2004 |
| WO | WO 2005028023 A1 | 3/2005 |
| WO | WO 2007021340 A1 | 2/2007 |
| WO | WO 2007022180 A1 | 2/2007 |
| WO | WO 2009039400 A2 | 3/2009 |
| WO | WO 2009120636 A1 | 10/2009 |
| WO | WO 2009124287 A1 | 10/2009 |
| WO | WO 10/088687 A1 | 5/2010 |
| WO | 2015023486 A1 | 2/2015 |

OTHER PUBLICATIONS

Medtronic, Inc., Cardiac Resynchronization Therapy for Heart Failure Management-Implant and Follow-up-Brief Overview 4 pages, 2002. (Applicant points out, in accordance with MPEP 609.04(a), that the year of publication, 2002, is sufficiently earlier than the effective U.S. filing date, so that the particular month of publication is not in issue.).

Luna Technologies, "About Distributed Sensing Technology", accessed on or about Dec. 28, 2010, 2 pp.

U.S. Appl. No. 16/169,276, filed Oct. 24, 2018, naming Inventors Grubac et al.

U.S. Appl. No. 16/158,724, filed Oct. 12, 2018, naming Inventors Chen et al.

U.S. Appl. No. 13/959,808, filed Aug. 6, 2013, naming Inventors Bonner et al.

(PCT/US2019/053419) PCT Notification of Transmittal of the International Search Report and the Written Opinion of the International Searching Authority, dated Dec. 18, 2019, 12 pages.

U.S. Appl. No. 16/847,315, naming inventors Drake et al., filed Apr. 13, 2020.

U.S. Appl. No. 16/847,344, naming inventors Drake et al., filed Apr. 13, 2020.

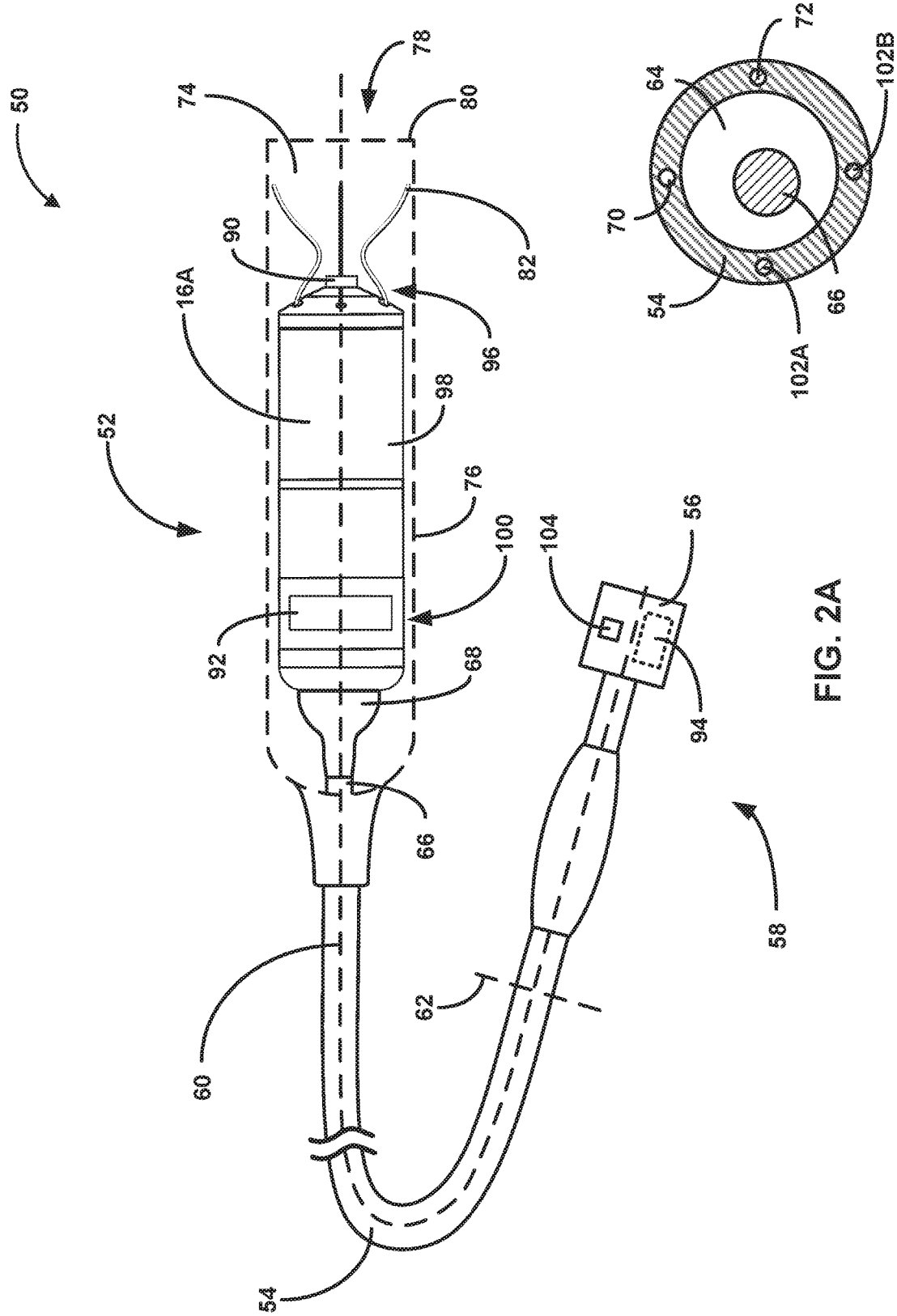

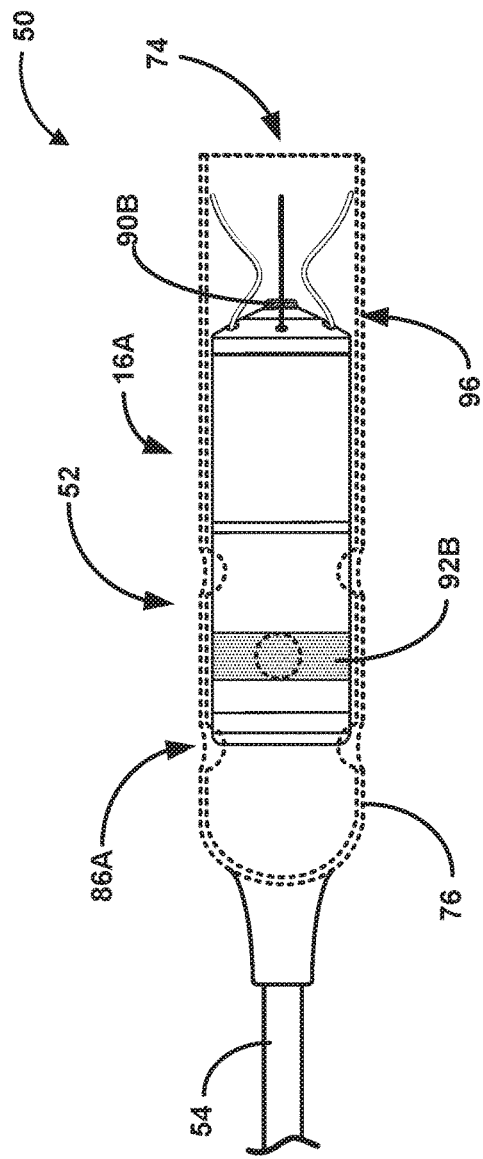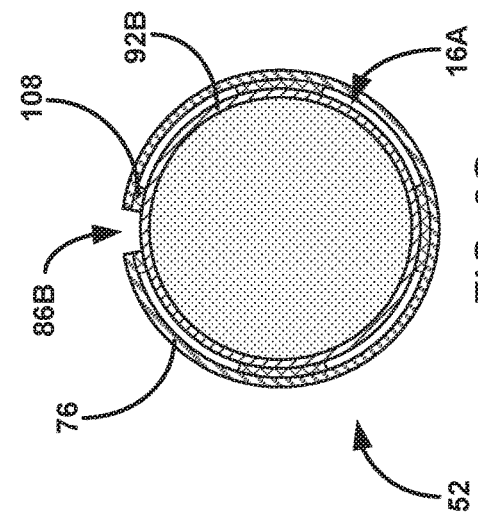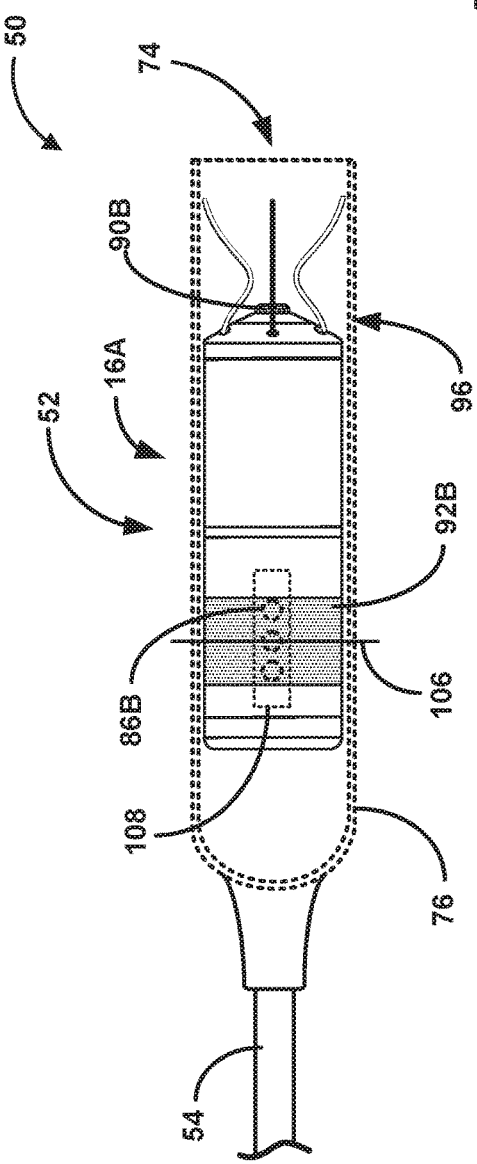

IMPEDANCE-BASED VERIFICATION FOR DELIVERY OF IMPLANTABLE MEDICAL DEVICES

TECHNICAL FIELD

The disclosure generally relates to medical delivery devices that are configured to deliver implantable and/or insertable medical devices to a target site within a human body.

BACKGROUND

A variety of medical devices for delivering a therapy and/or monitoring a physiological condition have been used clinically or proposed for clinical use in patients. Examples include medical devices that deliver therapy to and/or monitor conditions associated with the heart, muscles, nerves, brain, stomach or other organs or tissue or a patient. Some medical devices may employ one or more electrodes for the delivery of therapeutic electrical signals to such organs or tissues and/or one or more electrodes for sensing intrinsic electrical signals within the patient that are generated by such organs or tissue. Similarly, some medical devices may additionally or alternatively include one or more other sensors for sensing physiological parameters of a patient.

For example, some medical devices may function as cardiac pacemakers or cardioverter-defibrillators that provide therapeutic electrical signals to the heart. The therapeutic electrical signals may include pulses for pacing, or shocks for cardioversion or defibrillation. In some examples, a medical device may sense intrinsic depolarizations of the heart and thereby control delivery of therapeutic signals to the heart based on the sensed depolarizations. Upon detection of an abnormal rhythm, such as bradycardia, tachycardia, or fibrillation, an appropriate therapeutic electrical signal or signals may be delivered to restore or maintain a predetermined (e.g., relatively more normal) rhythm. For example, in some cases, an implanted medical device may deliver pacing stimulation to the heart of the patient upon detecting tachycardia or bradycardia, and/or deliver cardioversion or defibrillation shocks to the heart upon detecting fibrillation.

In some examples a medical device may utilize one or more medical leads with one or more electrodes or other sensors for delivery of therapeutic electrical signals or sensing. For example, electrodes or sensors may be carried at a distal portion of a lead, where, a proximal portion of the lead may be coupled to a medical device housing that contains circuitry such as signal generation and/or sensing circuitry. Alternatively, an implanted medical device may function without a lead, such that the implantable medical device includes one or more electrodes on its outer housing to deliver therapeutic electrical signals to patient, and/or sense intrinsic electrical signals of patient. For example, leadless cardiac devices, such as leadless pacemakers, may sense intrinsic depolarizations and/or other physiological parameters of the heart and/or deliver therapeutic electrical signals to the heart. Leadless cardiac devices may be positioned within or outside of the heart and, in some examples, may be anchored to a wall of the heart via a fixation mechanism. Leadless cardiac devices may be delivered to the heart percutaneously and/or transvascularly using a device that includes a catheter.

SUMMARY

Aspects of the disclosure are directed to methods and structures related to delivery devices for delivering implantable medical devices (IMDs) that are configured to verify that the delivery device and/or IMD are defining one or more fixation configurations relative to a target site of the patient. Fixation configurations may include spatial arrangements of the delivery device, IMD, and/or tissue of the target site that are indicative of efficacious fixation of the IMD to the target site. The fixation configurations may include a first fixation configuration that is tested (and potentially defined and therein verified) prior to deployment (and fixation) of the IMD to the target site. The first fixation configuration may include a spatial relationship of the delivery device relative to the tissue of the target site, wherein the spatial relationship is conducive to fixation elements of the IMD achieving desired fixation to the target site. For example, the first fixation configuration may relate to a delivery device orienting a deployment port in a predetermined manner relative to a surface of the target site. Additionally, or alternatively, the fixation configurations may include a second fixation configuration that is tested (and potentially defined and therein verified) subsequent to deployment and fixation of the IMD that relates to the IMD achieving a threshold amount of fixation. For example, the threshold amount of fixation may relate to a threshold number of fixation elements being fixated to tissue of the target site, therein causing a component (e.g., an electrode) of the IMD to achieve a threshold level of contact against the target site, or the threshold amount of fixation may relate to a threshold number of turns of a single distal screw being inserted into tissue of the target site.

The system may verify these fixation configurations by providing an electrical signal to fluid and/or tissue of a patient at the target site between two electrodes and then identifying and analyzing an impedance of this electrical signal as provided. For example, prior to deployment of the IMD, the system may send an electrical signal to fluid and/or tissue in an electrical path between a first electrode that is located inside of the deployment bay that houses the IMD and a second electrode that is located outside of the deployment bay. The system may then identify an impedance of the signal between these two electrodes. The system may be configured to identify that the delivery device defines the first fixation configuration when an impedance of this signal rises above a predetermined threshold (e.g., as a result of the electrical signal defining a path through tissue which has a higher resistance, indicating that the delivery port is adequately pressed against tissue of the target site). Similarly, the system may be configured to identify that the IMD defines the second fixation configuration when an impedance of this signal is stable, such as stable during a tug test (where the IMD is tugged lightly after the fixation elements have been supposedly secured to the target site). For example, the system may be configured to identify when the impedance of the signal picks up some harmonics such as a bimodal signature or relatively "noisy" slopes when the IMD is not in the second fixation configuration. Additionally, or alternatively, the system may identify an amount of lag between the voltage and the current (e.g., an amount that the voltage leads/lags the current) across the electrodes to identify phase waveform of the impedance electrical signal(s), and therein determine that the deployment bay and/or IMD define a first or second fixation configuration depending upon if the phase waveform is noisy or clean. Further, the system may be configured to execute fast Fourier transform (FFT) algorithms on the impedance signal to isolate frequency components that may indicate whether the deployment bay or IMD define fixation configurations. The system may then identify for the clinician if and whether the delivery device and/or IMD define the first, second, or neither fixation configuration.

In some examples, an implantable medical device delivery system includes an elongated member configured to navigate an intravascular system of a patient. The delivery system also includes a deployment bay connected to a distal portion of the elongated member and configured to house at least a portion of an implantable medical device (IMD). The deployment bay defines a distal opening configured for deployment of the IMD out of the deployment bay at a target site in a patient. The delivery system also includes a first electrode located inside of the deployment bay as the elongated member navigates the intravascular system. The delivery system also includes a second electrode. The delivery system also includes signal generation circuitry configured to deliver an electrical signal to a path between the first electrode and the second electrode through at least one of a fluid or tissue of the patient. The delivery system also includes processing circuitry configured to determine an impedance of the path based on the signal and control a user interface to indicate when an impedance of the path indicates that at least one of the IMD or the distal opening is in a fixation configuration relative to the target site of the patient.

In other examples, an implantable medical device delivery system includes an elongated member configured to navigate an intravascular system of a patient. The delivery system also includes a deployment bay connected to a distal portion of the elongated member and configured to house at least a portion of an implantable medical device (IMD). The deployment bay defines a distal opening configured for deployment of the IMD out of the deployment bay at a target site in a patient. The delivery system also includes a first electrode secured to an inner surface of the deployment bay. The delivery system also includes a second electrode secured to an outer surface of either the deployment bay or the elongated member. The delivery system also includes signal generation circuitry configured to deliver an electrical signal to a path between the first electrode and the second electrode through at least one of a fluid or tissue of the patient. The delivery system also includes processing circuitry configured to determine an impedance of the path based on the signal and control a user interface to indicate when an impedance of the path indicates that the distal opening is in a fixation configuration relative to the target site of the patient.

In other examples, an implantable medical device delivery system includes an implantable medical device (IMD) configured to be secured to a target site in a patient via a plurality of fixation elements extending distally from a distal tip of a housing of the IMD. The delivery system also includes a first electrode secured to the distal tip of the housing. The delivery system also includes a second electrode secured to an outer surface of a proximal portion of the housing. The delivery system also includes signal generation circuitry configured to deliver an electrical signal to a path between the first electrode and the second electrode through at least one of a fluid or tissue of the patient. The delivery system also includes processing circuitry configured to determine an impedance of the path based on the signal and control a user interface to indicate when an impedance of the path indicates that the IMD is in a fixation configuration relative to the target site of the patient.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

BRIEF DESCRIPTION OF DRAWINGS

FIG. 2A is a conceptual diagram illustrating an example delivery device that includes an elongated member, a deployment bay that is housing an example IMD, two electrodes, and circuitry that is configured to use impedance of an electrical signal between the two electrodes to determine if one of the deployment bay or IMD are defining a fixation configuration.

FIG. 2B is a conceptual diagram illustrating a cross-sectional view through the elongated member of the delivery device of FIG. 2A.

FIG. 2E is a conceptual diagram illustrating an example first and second electrode that are both secured to the IMD of FIG. 2A such that both are used to verifying if the deployment bay is defining the first fixation configuration and the IMD is defining a second fixation configuration as a result of a first set of holes through the wall of the deployment bay.

FIG. 2F is a conceptual diagram illustrating an example first and second electrode that are both secured to the IMD of FIG. 2A such that both are used to verifying if the deployment bay is defining the first fixation configuration and the IMD is defining a second fixation configuration as a result of a second set of holes through the wall of the deployment bay and one or ribs of deployment bay.

FIG. 2G is a conceptual diagram illustrating a cross-sectional view of the deployment bay, second electrode and ribs of FIG. 2F.

DETAILED DESCRIPTION

Figure 1A:
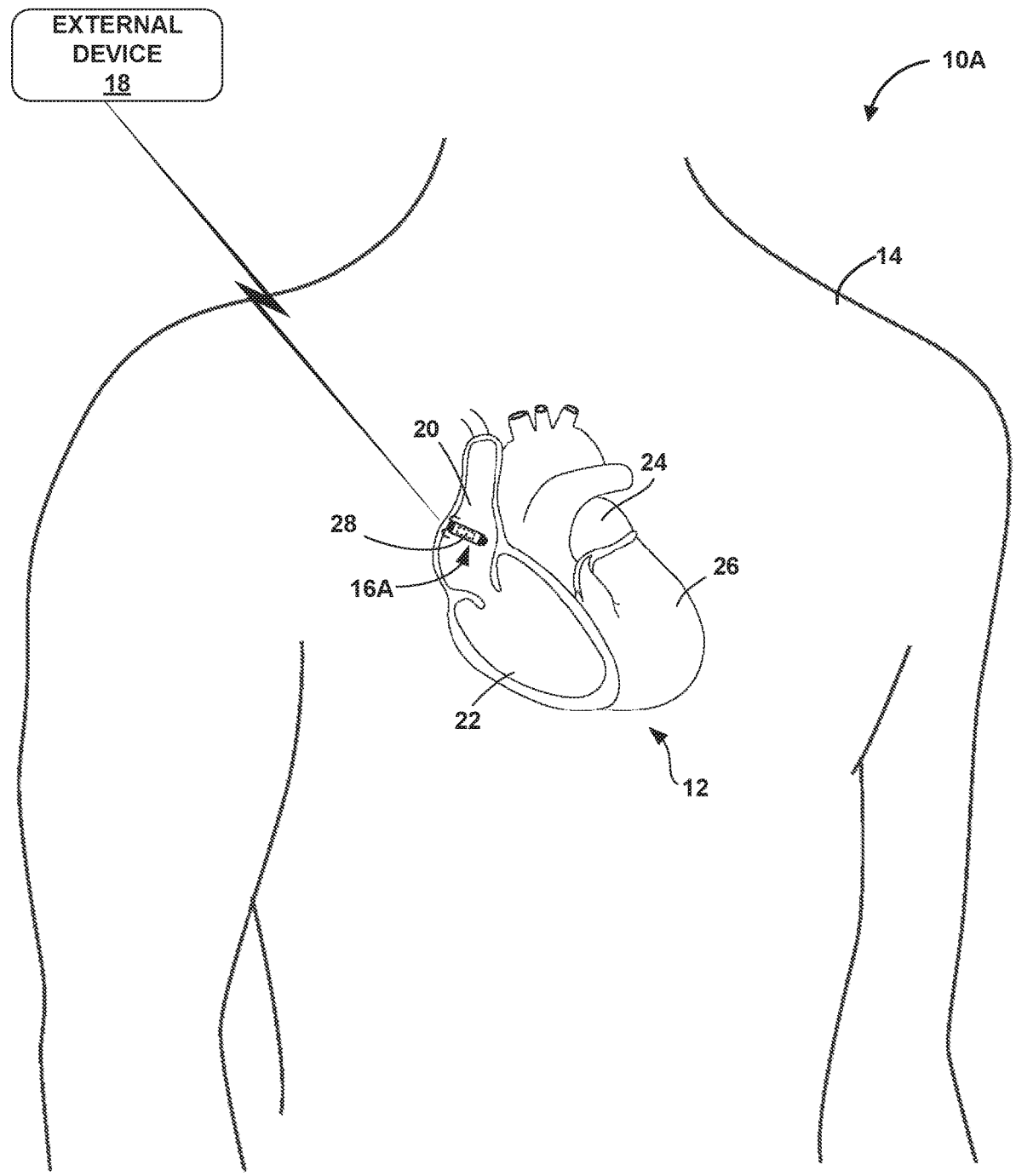
FIG. 1A is a conceptual diagram illustrating an example therapy system comprising a leadless implantable medical device (IMD) that may be used to monitor one or more physiological parameters of a patient and/or provide therapy to the heart of a patient.

Aspects of this disclosure relate to methods and systems for delivering an implantable medical device (IMD) to a target site in a patient and therein verifying efficacious fixation configuration of the delivery device and IMD relative to the target site. The IMD may be secured to the target site once navigated to the target site with fixation elements on or near a distal end of the IMD. The delivery device may include a navigable elongated member (e.g., a catheter), a deployment bay at a distal end of the elongated member, and a verification system that is configured to verify when the delivery device and/or IMD define one or more fixation configurations relative to the target site. For example, aspects of the methods and systems disclosed herein relate to providing an electrical signal to fluid and/or tissue of the patient between electrodes of the system, and therein analyzing an impedance of the delivered electrical signal to verify when the delivery device and/or IMD define fixation configurations relative to the target site.

The delivery device and/or IMD may include a first electrode that is contained within a deployment bay of the delivery device during intravascular navigation and at least a second electrode. Further, the delivery device and/or IMD may include circuitry that is configured to deliver (and then analyze) an electrical signal to fluid and/or tissue between two electrodes. For example, a first electrode may be secured to an inner surface (e.g., a surface that faces the IMD) of the deployment bay and a second electrode may be secured to an outer surface (a surface that faces the vasculature) of the deployment bay, and circuitry may be configured to provide an electrical signal to fluid and tissue between the two electrodes. The circuitry may therein be configured to monitor an impedance of the electrical signal as provided across the electrodes, and identify when the signal rises above a threshold magnitude. Where the IMD includes distal-extending fixation elements of the IMD, deploying the IMD from the deployment bay at an angle that is substantially square to the surface of the tissue site may improve an ability of the fixation elements to secure the IMD to the tissue. As such, configuring the circuitry to detect when an impedance of an electrical signal provided across the distal port of the deployment bay may functionally provide an indication as to when the delivery device defines an efficacious deployment arrangement. The circuitry may be configured to provide an indication to a clinician as to when the delivery device defines such a fixation configuration (e.g., using a user interface of the system).

Similarly, the IMD may include a first electrode that is secured to a distal tip of the IMD and a second electrode that is proximal to the distal tip. In some examples, the first electrode of the delivery device may be the first electrode of the IMD. In such examples, the second electrode of the delivery device may be a second electrode of the IMD that is secured to the IMD at a location proximal to the distal tip of the IMD, or the second electrode may be secured to the deployment receptacle at a location proximal to the distal tip of the IMD. In other examples, the delivery device may include two discrete electrodes and the IMD may include two discrete electrodes, such that the full system includes two sets of electrodes that each verify one of the fixation configurations. Circuitry of the IMD may be configured to provide an electrical signal to fluid and tissue between the first electrode on the distal tip and the second electrode proximal to the first electrode. The circuitry may therein be configured to monitor an impedance of the electrical signal as provided across the electrodes, and identify if the signal incorporates any harmonics over time and during a stress test. Where the IMD includes a therapeutic element on its distal tip (e.g., such as an electrode configured to provide therapy or sensing to a patient), the IMD may have an improved ability to provide therapy using this therapeutic element when the IMD is squarely and securely pressing the therapeutic element into tissue of the patient. As such, configuring the circuitry to detect when an impedance of an electrical signal provided through an electrode on the distal tip includes harmonics may functionally provide an indication as to when the IMD has not been deployed such that a therapeutic element on its distal tip is squarely and securely pressing into tissue at the target site. The circuitry may be configured to provide an indication to a clinician as to when the IMD is not identifying an impedance with such harmonics and is therein defining an efficacious fixation configuration.

FIG. 1A is a conceptual diagram illustrating an example therapy system 10A that may be used to monitor one or more physiological parameters of heart 12 of patient 14 and/or to provide therapy to heart 12 of patient 14 using one or more medical devices delivered using the delivery device of this disclosure. Patient 14 is ordinarily, but not necessarily, a human patient. Therapy system 10A includes implantable medical device (IMD) 16A, which is communicatively coupled, e.g., wirelessly, to external device 18. IMD 16A may be an implantable leadless pacemaker that provides electrical signals to heart 12 via one or more electrodes (not shown in FIG. 1) on its outer housing. Additionally, or alternatively, IMD 16A may sense electrical signals attendant to the depolarization and repolarization of heart 12 via electrodes on its outer housing. In some examples, IMD 16A provides pacing pulses to heart 12 based on the electrical signals sensed within heart 12. For example, IMD 16A may be a Micra™ device of the Transcatheter Pacing System (TPS), which is commercial available from Medtronic Public Limited Company, of Dublin, Ireland.

IMD 16A may include circuitry within a hermetically sealed housing of IMD 16A. IMD 16A may also include a power source and/or memory for circuitry 28. Circuitry 28 may be configured to provide the functionality attributed to IMD 16A as described herein. For example, as described in greater detail below, circuitry 28 of IMD 16A may include circuitry configured to provide electrical signals across electrodes to verify that a delivery device and/or IMD 16A is defining efficacious fixation configurations during a deployment procedure. These electrical signals may include sinusoidal waveforms and/or pulses. Circuitry 28 may include one or more microprocessors, digital signal processors (DSPs), application specific integrated circuits (ASICs), field programmable gate arrays (FPGAs), or any other equivalent integrated or discrete logic circuitry, as well as any combinations of such components.

For example, circuitry 28 may include processing circuitry, stimulation circuitry, telemetry circuitry, sensing circuitry, or the like. Stimulation circuitry may generate and deliver electrical stimulation under the control of processing circuitry. For example, in operation, processing circuitry may access a memory to load therapy programs to stimulation circuitry, where stimulation parameters of therapy programs may include a voltage amplitude, a current amplitude, a pulse rate, a pulse width, a duty cycle, or a combination of electrodes (e.g., where electrodes are secured to IMD 16A). Further, stimulation circuitry may have some overlap with signal generation circuitry as described below (e.g., signal generation circuitry 124 of FIG. 3).

Telemetry circuitry may be configured for wireless communication using radio frequency protocols or inductive communication protocols. Telemetry circuitry may include one or more antennas configured to communicate with external device 18, for example. Processing circuitry may transmit operational information such as sensing information and receive therapy programs or therapy parameter adjustments via telemetry circuit. Also, in some examples, IMD 16A may communicate with other implanted devices, such as stimulators, control devices, or sensors, via telemetry circuit. Sensing circuitry may be configured to sense one or more parameters of patient 14. For example, sensing circuitry may sense parameters of heart 12 using electrodes of IMD 16A. Based on sensed values of sensing circuitry, processing circuitry may use telemetry circuitry to provide information or use stimulation circuitry to provide therapy related to sensed values. Further, as described herein, processing circuitry may use telemetry circuitry to send indications of fixation or indications of non-fixation to various user interfaces for a clinician.

IMD 16A may include fixation elements such as a set of fixation tines to secure IMD 16A to patient tissue. The fixation elements of IMD 16A may be located near a distal end of IMD 16A, such that the fixation elements are configured to extend out the distal opening of the deployment bay of the delivery device prior to and/or concurrently with IMD 16A being deployed using the delivery device. In the example of FIG. 1A, IMD 16A is positioned wholly within heart 12 proximate to an inner wall of right atrium 20 to provide right atrium 20 pacing. In other examples, IMD 16A may be positioned at any other location outside of or within heart 12. For example, IMD 16A may be positioned outside or within right ventricle 22, left atrium 24, and/or left ventricle 26 (e.g., to provide right ventricle, left atrial, and left ventricular pacing), respectively. Further, although a single IMD 16A is shown in FIG. 1A, system 10A may include additional IMDs that are similar to or different from IMD 16A.

Depending on the location of implant, IMD 16A may include other stimulation functionalities. For example, IMD 16A may provide atrioventricular nodal stimulation, fat pad stimulation, vagal stimulation, or other types of electrical stimulation. In other examples, IMD 16A may be a monitor that senses one or more parameters of heart 12 (e.g., electrical activity mechanical activity, and/or blood pressure) and may not provide any stimulation functionality. In some examples, system 10A may include a plurality of leadless IMDs 16A to provide stimulation and/or sensing at a variety of locations.

As mentioned above, IMD 16A may be delivered and deployed to its target site using the delivery device described herein. IMD 16A may be contained substantially entirely within a deployment bay of the delivery device such that fixation elements of IMD 16A are adjacent a distal opening of the deployment bay. Upon securing attachment of IMD 16A to the target site (e.g., through fixation tines as depicted in FIG. 1A), delivery device may be retracted from patient 14 (e.g., including retracting the delivery device over a proximal end of IMD 16A, depending upon whether IMD 16A may be secured before full deployment).

In many cases, an efficacy of IMD 16A may be impacted by a quality of fixation of IMD 16A. For example, IMD 16A may include a plurality of fixation tines that are configured to press a distal electrode of IMD 16A up against tissue of target site of patient 14. If fixation tines have a disadvantageous fixation to the tissue, it may be difficult or impossible for IMD 16A to provide the functionality described herein using such a distal electrode. For example, if only one of a plurality of fixation tines is affixed to the tissue, or if fixation tines are affixing IMD 16A at an angle relative to the tissue, a distal electrode may have relatively poor contact with the target site (e.g., poor contact with right atrium 20). As a result of such poor contact (which is itself a result of disadvantageous fixation), an efficacy of IMD 16A may be reduced.

In some examples, a clinician may utilize a "tug test" to verify if fixation elements of IMD 16A have properly engaged tissue of the target site. A tug test may include tugging on a proximal end of IMD 16A with, e.g., a tether (such as tether 162 of FIGS. 5B and 5D). In some examples, as depicted in FIGS. 5B and 5D, the tug test may be conducted when IMD 16A is substantially entirely deployed out of deployment bay 52 and therein substantially unconstrained by deployment bay 52. A clinician may view IMD 16A at the target site using fluoroscopy or the like to ensure that fixation elements appear to have properly engaged tissue of the target site. However, in some examples, a target site may a relatively thin wall of tissue such that it may be difficult for a clinician to adequately see such engagement. For example, walls of right atrium 20 and/or left atrium 24 may be relatively thin, such that it is difficult or impossible for a clinician to verify that IMD 16A has been efficaciously attached to tissue of the target site using fixation elements.

Aspects of this disclosure relate to verifying that one or both of a delivery device and IMD 16A are defining advantageous fixation configurations that are likely to result in good contact of a distal electrode or the like of IMD 16A with tissue of a target site. For example, a delivery device may be configured to provide an electrical signal to fluid and/or tissue of patient 14 between a first electrode within a deployment bay of the delivery device and a second electrode outside of the deployment bay. When a distal opening of the delivery device is not aligned with a target site (e.g., such that a face that defines the distal opening is at an angle relative to the tissue of the target site), the path between the two electrodes (e.g., the path of least resistance that the electrical between the electrodes will take) may substantially include fluid of patient 14. Conversely, when a distal opening of the delivery device is aligned and adequately pressed into tissue of a target site, the path between the two electrodes may include at least some tissue of patient 14 (e.g., the path for the electrical signal to exit the enclosure of the deployment bay, such as through the distal port). A path through tissue of patient 14 may have a higher impedance than a path that substantially or entirely includes fluid of patient 14. Processing circuitry (such as processing circuitry of the delivery device or circuitry 28 of IMD 16A) may detect this relatively higher impedance, e.g., an impedance that exceeds or otherwise satisfies a threshold, and may cause a user interface (e.g., a screen or a light or the like) to indicate to a clinician that the delivery device is oriented properly for the deployment of IMD 16A.

Additionally, or alternatively, processing circuitry (of the delivery device or of IMD 16A) may be configured to send an electrical signal between a distal electrode of IMD 16A and a second electrode proximal to the distal electrode of IMD 16A after IMD 16A is deployed. In this example, processing circuitry may be configured to evaluate the impedance of signal provided between the first electrode and another electrode after IMD 16A has been deployed and secured to tissue. If the fixation elements of IMD 16A (e.g., such as the fixation tines as described above) have pressed the first electrode against tissue of the target site, impedance of the signal may include substantially stable impedance values. Conversely, if the fixation means of IMD 16A did not engage tissue of the target site as expected, the processing circuitry of the delivery device may identify harmonics in the impedance values of the electrical signal across the electrodes, such as bimodal signatures or relatively "noisy" slopes. Processing circuitry of the delivery device may determine whether the signal is "stable" or includes harmonics, and may cause a user interface (e.g., a screen or a light or the like) to indicate to a clinician that fixation means of IMD 16A are well engaged or poorly engaged, respectively, as a result of this determination.

As a result of processing circuitry (of the delivery device and/or of IMD 16A) verifying whether the delivery device is properly oriented for deployment and/or verifying whether IMD 16A has achieved proper fixation post-deployment, the processing circuitry may improve an ability of a clinician to arrange system 10A such that each IMD 16A (and therein a distal electrode of each IMD 16A) has good contact with tissue of intended target sites. As a result of IMDs 16A having good contact, system 10A may have an approved ability to treat and/or monitor patients 14 as described herein.

FIG. 1A further depicts external device 18 such as a (clinician or patient) programmer in wireless communication with IMD 16A. In some examples, external device 18 comprises a handheld computing device, computer workstation, or networked computing device. External device 18 may include a user interface that presents information to and receives input from a user. It should be noted that the user may also interact with external device 18 remotely via a networked computing device.

A user, such as a physician, technician, surgeon, electrophysiologist, other clinician, or patient, interacts with external device 18 to communicate with IMD 16A. For example, the user may interact with external device 18 to retrieve physiological or diagnostic information from IMD 16A. For example, the user may use external device 18 to retrieve information from IMD 16A regarding the rhythm of heart 12, heart rhythm trends over time, or arrhythmic episodes. A user may also interact with external device 18 to program IMD 16A.

In some examples, the user may use external device 18 to retrieve information from IMD 16A regarding other sensed physiological parameters of patient 14 or identify information that is derived from sensed physiological parameters, such as intracardiac or intravascular pressure, activity, posture, tissue oxygen levels, blood oxygen levels, respiration, tissue perfusion, heart sounds, cardiac electrogram (EGM), intracardiac impedance, thoracic impedance, or the like. In some examples, the user may use external device 18 to retrieve information from IMD 16A regarding the performance or integrity of IMD 16A or the performance or integrity of respective components of system 10A, such as a power source of IMD 16A. As another example, the user may interact with external device 18 to select values of parameters of therapies provided by IMD 16A, such as pacing and/or neurostimulation therapies.

Further, in some examples external device 18 may include a user interface as described herein that is used to indicate fixation and/or non-fixation configurations to clinician. For example, circuitry that is configured to deliver an electrical signal to tissue and/or fluid between two electrodes and therein use an impedance of the signal to verify whether or not a delivery device and/or IMD 16A defines fixation configurations may then provide this information (using telemetry techniques described herein) to external device 18. Further, a clinician may provide inputs or commands to circuitry regarding verifying or testing fixation configurations using external device 18. For example, a clinician may use an interface of external device 18 to have circuitry of IMD 16A and/or a delivery device start verifying whether the delivery device defines a first fixation configuration, stop verifying whether the delivery device defines the first fixation configuration, start verifying whether IMD 16A defines the second fixation configuration, stop verifying whether IMD 16A defines the second fixation configuration, or the like.

IMD 16A and external device 18 may communicate via wireless communication using any technique known in the art. Examples of communication techniques may include low frequency or radiofrequency (RF) telemetry. In some examples, external device 18 may include a programming head that may be placed proximate to the patient's body near the IMD 16A implant site in order to improve the quality or security of communication between IMD 16A and external device 18.

Figure 1B:
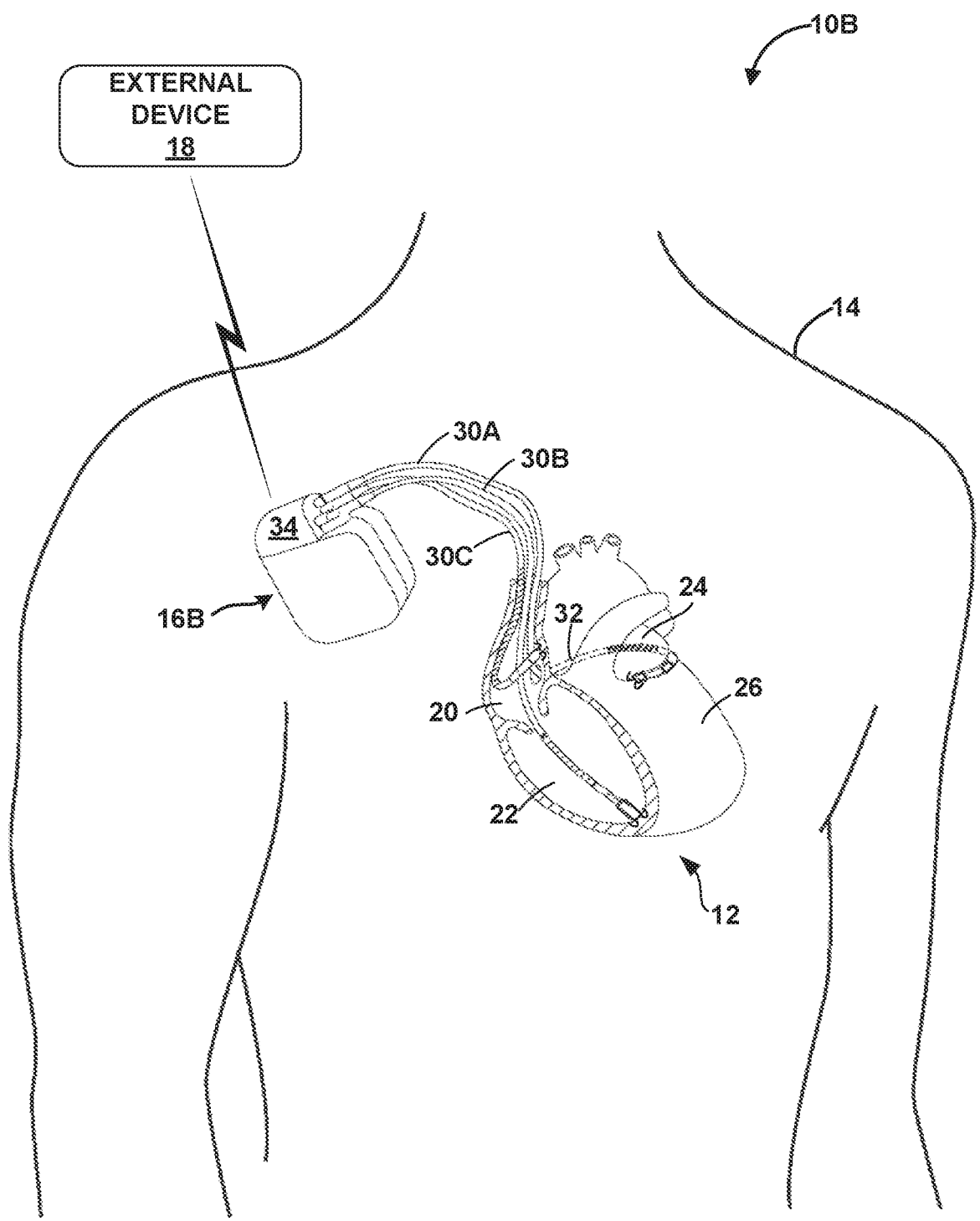
FIG. 1B is a conceptual diagram illustrating another example therapy system comprising an IMD coupled to a plurality of leads that may be used to monitor one or more physiological parameters of a patient and/or provide therapy to the heart of a patient.

FIG. 1B is a conceptual diagram illustrating another example therapy system 10B that may be used to monitor one or more physiological parameters of patient 14 and/or to provide therapy to heart 12 of patient 14 using leads 30A, 30B, 30C (collectively "leads 30") implanted in patient 14 using the delivery device and methods described herein. Therapy system 10B includes IMD 16B which is coupled to leads 30 and external device 18. As referred to herein, all of IMD 16B and leads 30 may be collectively referred to generally as an IMD. In one example, IMD 16B may be an implantable pacemaker that provides electrical signals to heart 12 via electrodes coupled to one or more of leads 30. IMD 16B may include an electrical stimulation generator and may be attached to the proximal end of medical leads 30. In other examples, in addition to or alternatively to pacing therapy, IMD 16B may deliver neurostimulation signals. In some examples, IMD 16B may also include cardioversion and/or defibrillation functionalities. In other examples, IMD 16B may exclusively or predominantly provide monitoring functionalities.

Medical leads 30 extend into the heart 12 of patient 14 to sense electrical activity of heart 12 and/or deliver electrical stimulation to heart 12. In some examples, each medical lead 30 of FIG. 1B may be delivered to their respective target sites using the delivery device according to the delivery techniques described herein. In the example shown in FIG. 1B, right ventricular (RV) lead 30B extends through one or more veins (not shown), the superior vena cava (not shown), right atrium 20, and into right ventricle 22. RV lead 30B may be used to deliver RV pacing to heart 12. Left ventricular (LV) lead 30A extends through one or more veins, the vena cava, right atrium 20, and into the coronary sinus 32 to a region adjacent to the free wall of left ventricle 26 of heart 12. Alternatively, LV lead 30A may be implanted "directly" into the left ventricle 26, such that LV lead 30A, e.g., extends through a hole in the ventricular septum or atrial septum. LV lead 30A may be used to deliver LV pacing to heart 12. Right atrial (RA) lead 30C extends through one or more veins and the vena cava, and into the right atrium 20 of heart 12. RA lead 30C may be used to deliver RA pacing to heart 12.

In some examples, system 10B may additionally or alternatively include one or more leads or lead segments (not shown in FIG. 1B) that deploy one or more electrodes within the vena cava or other vein, or within or near the aorta. Furthermore, in another example, system 10B may additionally or alternatively include one or more additional intravenous or extravascular leads or lead segments that deploy one or more electrodes epicardially, such as near an epicardial fat pad, or proximate to the vagus nerve. In other examples, system 10B may not include one of ventricular leads 30A and 30B.

One or more of medical leads 30 may include one or more fixation elements such as a set of fixation tines to secure a distal end of the medical lead to patient tissue or at a fixed position relative to patient tissue (e.g., where a fixation element of one or more medical leads 30 expands against rather than penetrates patient tissue). The inclusion of fixation elements such as tines for each medical lead 30 is merely illustrated for purposes of clarity, as in some examples other fixation means (such as a distal helical coil or the like) may be utilized. As depicted, fixation elements may include distal tines that are configured to distally extend from leads 30 and are self-biasing upon deployment (e.g., deployed from a deployment bay of a delivery device as described herein to a biased configuration). In other examples, fixation elements may include other types of tines, such as tines that do not self-bias (but are caused to bias or deform or actuate by another component), tines of other shapes (e.g., helical tines), tines that are configured to be manually controlled to a clinician, or the like. Fixation elements such as tines may be constructed of substantially any bio-compatible material.

As mentioned above, one or more medical leads 30 may be delivered and deployed to respective target sites using the delivery device described herein. Medical leads 30 may be deployed to respective target sites within or near heart 12 in subsequent procedures using one or more the delivery devices herein. In such examples, the fixation elements of the respective medical leads 30 may be navigated to the target site within a deployment bay of the delivery device, such that other portions of respective medical leads 30 may be housed by a lumen of some of the deployment bay and/or elongated member of the delivery device. Upon deploying the distal end of medical leads 30 to secure respective medical leads 30 to the target site, the delivery device may be withdrawn over respective medical leads 30 to retract the delivery device from patient 14. In this way, upon successfully deploying one of medical leads 30, a clinician may retract the delivery device such that the delivery device moves proximally relative to the respective deployed medical lead 30 (e.g., such that respective deployed and distally secured medical lead 30 slides within the one or more lumens of the delivery device as defined by the deployment bay and/or elongated member of the delivery device as the delivery device is retracted).

IMD 16B may sense electrical signals attendant to the depolarization and repolarization of heart 12 via electrodes coupled to at least one of the leads 30. In some examples, IMD 16B provides pacing pulses to heart 12 based on the electrical signals sensed within heart 12. The configurations of electrodes used by IMD 16B for sensing and pacing may be unipolar or bipolar.

IMD 16B may also provide neurostimulation therapy, defibrillation therapy and/or cardioversion therapy via electrodes located on at least one of the leads 30. For example, IMD 16B may deliver defibrillation therapy to heart 12 in the form of electrical pulses upon detecting ventricular fibrillation of ventricles 22 and 26. In some examples, IMD 16B may be programmed to deliver a progression of therapies, such as pulses with increasing energy levels, until a fibrillation of heart 12 is stopped. As another example, IMD 16B may deliver cardioversion or anti-tachycardia pacing (ATP) in response to detecting ventricular tachycardia, such as tachycardia of ventricles 22 and 26.

As described above with respect to IMD 16A of FIG. 1, external device 18 such as a clinician or patient programmer may be used to communicate with IMD 16B. In addition to the functions described with respect to IMD 16A of FIG. 1, a user may use external device 18 to retrieve information from IMD 16B regarding the performance or integrity of leads 30 and may interact with external device 18 to select parameters for any additional therapies provided by IMD 16B, such as cardioversion and/or defibrillation.

Leads 30 may be electrically coupled to signal generation circuitry and sensing circuitry (not shown) of IMD 16B via connector block 34. In some examples, proximal ends of leads 30 may include electrical contacts that electrically couple to respective electrical contacts within connector block 34 of IMD 16B. Although not shown in FIG. 1B, IMD 16B may include circuitry 28, similar to IMD 16A. Circuitry 28 may include the processing circuitry, signal generation circuitry, and sensing circuitry described above, along with any other circuitry, power source, antennas, or other hardware or software necessary or helpful to configure IMD 16B to provide therapy and/or monitor a condition of patient 14. In some examples, signal generation circuitry of IMD 16A may be used to deliver the electrical signal between electrodes described herein to verify fixation configurations. In other examples, leads 30 may be coupled to another system to generate electrical signals and identify impedance of those signals to verify fixation configurations as described herein.

The configuration of system 10B illustrated in FIG. 1B is merely one example. In other examples, a system may include extravascular leads, subcutaneous lead, substernal leads, epicardial leads and/or patch electrodes instead of or in addition to the transvenous leads 30 illustrated in FIG. 1B. Further, IMD 16B need not be implanted within patient 14. For each of these examples, any number of the medical leads may include a set of fixation tines on a distal end of the medical lead that were navigated to their respective target sites using delivery devices in accordance with the techniques described herein.

In addition, in other examples, a system may include any suitable number of leads coupled to IMD 16B, and each of the leads may extend to any location within or proximate to heart 12. For example, other examples of systems may include three transvenous leads located as illustrated in FIG. 1B, and an additional lead located within or proximate to left atrium 24. Other examples of systems may include a single lead that extends from IMD 16B into right atrium 20 or right ventricle 22, or two leads that extend into a respective one of the right ventricle 22 and right atrium 20. In each of these examples, any number of the medical leads may include a fixation mechanism on a distal end of the medical lead and may be delivered with a medical delivery device in accordance with the techniques described herein.

FIG. 2A depicts an example medical delivery device 50 for delivering implantable medical devices such as IMD 16A. Though delivery device 50 is depicted and discussed herein as deploying and verifying fixation configurations of and/or for IMD 16A, it is to be understood that delivery device 50 may be used to deploy and verify fixation configurations for other IMDs or other IMD components (e.g., leads 30 of IMD 16B) in other examples. Delivery device 50 may include deployment bay 52 that is configured to house at least a portion of IMD 16A and deploy IMD 16A. In some examples, deployment bay 52 may be configured to house substantially all of IMD 16A prior to deploying IMD 16A. Deployment bay 52 may be connected to a distal portion of elongated member 54 of delivery device 50. Deployment bay 52 and elongated member 54 may be configured to navigate an intravascular system of a patient. For example, a clinician may navigate deployment bay 52 and elongated member 54 through an intravascular system until deployment bay 52 is at a target site in a patient in order to deploy IMD 16A from deployment bay 52. A clinician may use hub 56 of delivery device 50 to handle delivery device 50 and/or navigate deployment bay 52 to a target site. Hub 56 of delivery device 50 may be at proximal portion 58 of delivery device 50. In some examples, hub 56 may be configured to remain external to patient 14 as deployment bay 52 is navigated to the target site, enabling a clinician to navigate an intravenous system and deploy IMD 16A using one or more mechanisms or ports (not depicted) of hub 56. Deployment bay 52 may be located at or near a distal end of delivery device 50, and hub 56 may be located at or near a proximal end of delivery device 50, with elongated member 54 extending between hub 56 and deployment bay 52.

Elongated member 54 may be a flexible elongated component that longitudinally extends along delivery device 50. Elongated member 54 may extend between deployment bay 52 and hub 56 of delivery device 50 along longitudinal axis 60 of delivery device 50. Elongated member 54 may be substantially cylindrical such that elongated member 54 defines a substantially circular cross-sectional shape. In other examples, elongated member 54 may define one or more other cross-section shapes, including defining a plurality of cross-sectional shapes along a longitudinal length of elongated member 54.

Elongated member 54 may define a number of longitudinal lumens for a variety of purposes. For example, as depicted in conceptual cross-sectional view of FIG. 2B as taken along cut-line 62, elongated member 54 may define lumen 64 that occupies a majority of a cross-sectional width of elongated member 54. Lumen 64 may be configured to house deployment mechanism 66 that can axially slide (e.g., slides along longitudinal axis 60 of delivery device 50) within lumen 64 relative to delivery device 50. In this way, a clinician may, e.g., deploy IMD 16A from deployment bay 52 once the clinician navigates deployment bay 52 to a target site as a result of an action executed using deployment mechanism 66. For example, turning back to FIG. 2A, deployment mechanism 66 may include pushing element 68 at a distal end of deployment mechanism 66. Pushing element 68 may be configured to contact and impart a distal force on a proximal face of IMD 16A in response to deployment mechanism 66 being slide distally within lumen 64. Additionally, or alternatively, deployment mechanism 66 may include a tether or catch (e.g., similar to tether 162 of FIGS. 5B and 5D) that is used to hold, push, retract, or otherwise move IMD 16A relative to deployment bay 52.

Turning back to FIG. 2B, lumen 64 may alternatively or additionally be configured to house a portion of an insertable or implantable medical device (e.g., where an implantable medical device includes one of leads 30 of FIG. 1B) to be deployed by delivery device 50. Elongated member 62 may further define guidewire lumen 70 that is configured to house a guidewire that can axially slide (e.g., move along longitudinal axis 60 of delivery device 50) within guidewire lumen 70 relative to delivery device 50 (e.g., such that deployment bay 52 is navigated to the target site by sliding delivery device 50 along a guidewire that was previously navigated to the target site). Alternatively, or additionally, one or more deflection members 72 may be embedded within elongated member 54. Deflection members 72 may be configured to deflect elongated member 54 in one or more directions. For example, deflection members 72 may include wires that are pulled or pushed using a port or control member on hub 56 to deflect elongated member 54. Deflection members 72 may be configured to deflect elongated member 54 in a predetermined manner that is configured to navigate delivery device 50 to the target site. Put differently, deflection members 72 as longitudinally embedded within elongated member 54 may be configured to deflect elongated member 54 in a predetermined manner when delivery device 50 is inserted in patient 14 (e.g., to navigate through a particularly tortuous and predetermined length of intravenous system).

Turning back to FIG. 2A, as discussed above, delivery device 50 may be configured to be inserted into patient 14 to deliver IMD 16A. In some examples, delivery device 50 may be configured to be inserted into patient 14 using an introducer sheath (not depicted). Delivery device 50 may be made of one or more biocompatible materials. For example, delivery device 50 may include polymeric materials such as polyether block amide (PEBA), low density polyethylene (LDPE), high density polyethylene (HDPE), polytetrafluoroethylene (PTFE), polybutylene terephthalate (PBT), polyethylene terephthalate (PET), nylons, or the like, and/or delivery device 50 may be made out of metallic materials such as titanium, nitinol, stainless steel, or the like.

In some examples, as depicted in FIG. 2A, deployment bay 52 may house IMD 16A within recess 74 as defined by outer wall 76 of deployment bay 52. Deployment bay 52 may define recess 74 as a physical space that is sized to partially or entirely contain IMD 16A as delivery device 50. Outer wall 76 may enclose an axial length of IMD 16A. In some examples, as depicted, outer wall 76 may extend radially in at a proximal end of deployment bay 52 to block proximal movement of IMD 16A relative to deployment bay 52. Though deployment bay 52 is depicted as transparent in FIG. 2A for purposes of illustration (to depict IMD 16A), it is to be understood that deployment bay 52 may define a substantially continuous enclosure that may or may not be transparent and mostly or fully radially encloses IMD 16A along a length of IMD 16A.

Deployment bay 52 may define distal opening 78 to recess 74 through which IMD 16A. Delivery device 50 may be configured to deploy IMD 16A from recess 74 through distal opening 78. In some examples, distal surface 80 of deployment bay 52 may define distal opening 78. Deployment bay 52 may define recess 74 such that, when IMD 16A is received within recess 74, one or more fixation elements 82 are proximal to distal opening 78. In some examples, one or more fixation elements 82 may interface with an inner surface of outer wall 76 of deployment bay 52 prior to and during the navigation of IMD 16A to a target site. Put differently, a distal end of fixation elements 82 may contact an inner surface of outer wall 76 when IMD 16A is within deployment bay 52, and further, fixation elements 82 may press against the inner surface and/or distal surface 80 to deploy IMD 16A at the target site.

Figure 2C:
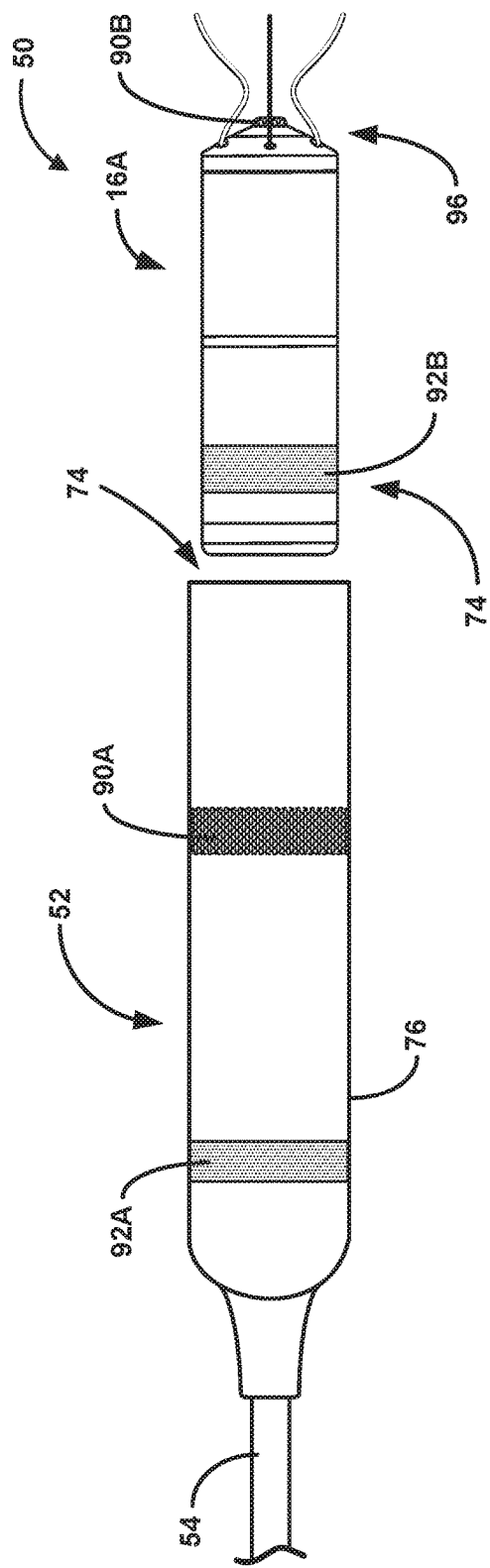
FIG. 2C is a conceptual diagram illustrating an example first and second electrode on the deployment bay of FIG. 2A for verifying if the deployment bay is defining a first fixation configuration as well as an example first and second electrode on the IMD of FIG. 2A for verifying if the IMD is defining a second fixation configuration.
Figure 2D:
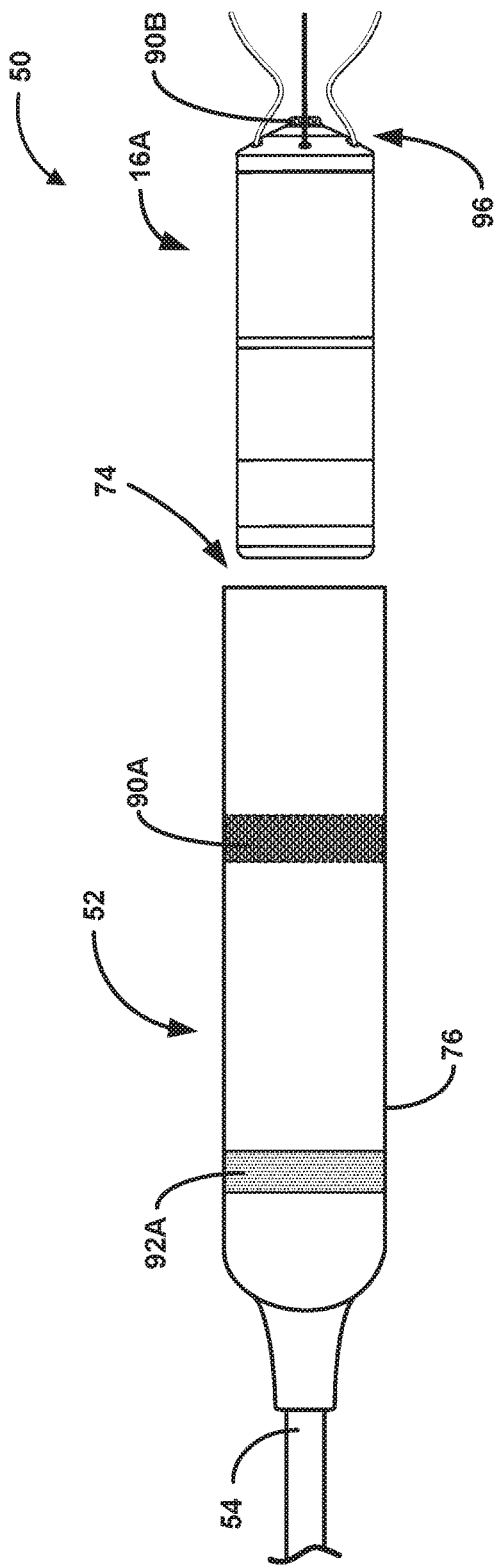
FIG. 2D is a conceptual diagram illustrating an example first electrode on the deployment bay of FIG. 2A for verifying if the deployment bay is defining a first fixation configuration as well as an example first electrode on the IMD of FIG. 2A for verifying if the IMD is defining a second fixation configuration, wherein both first electrodes are configured to be used with a common second electrode on the deployment bay.

Delivery device 50 may include a plurality of electrodes and a set of circuitry that is configured to verify when deployment bay 52 and/or IMD 16A defines one or more fixation configurations relative to tissue of a target site within patient 14. For example, delivery device 50 may include first electrode 90, second electrode 92, and circuitry 94 for verifying if deployment bay 52 and/or IMD 16A defines a fixation configuration. Circuitry 94 may be configured to cause first electrode 90 and second electrode 92 to deliver an electrical signal to fluid and/or tissue along a path between first electrode 90 and second electrode 92. Circuitry 94 may then use a determined impedance of the electrical signal across this path to verify whether the deployment bay 52 and/or IMD 16A are defining a fixation configuration relative to target site tissue. The depicted location and size of each of first electrode 90, second electrode 92, and circuitry 94 is for purposes of illustration only, as each of these components may be at many locations and may be sized and shaped differently as described herein (e.g., as depicted in FIGS. 2C and 2D).

First electrode 90 may be located within recess 74 of deployment bay 52. For example, first electrode 90 may be secured to an inner surface of outer wall 76 of deployment bay 52. Alternatively, first electrode 90 may be secured to distal tip 96 of housing 98 of IMD 16A. In such examples, first electrode 90 may be the primary sensing/pacing/defibrillation electrode of IMD 16A. Regardless of location, first electrode 90 may be configured to be exposed to fluid of a patient when deployment bay 52 is navigated to a target site. Put differently, a conductive surface of first electrode 90 may be configured to directly electrically couple with a fluid (e.g., such as blood) of a patient when deployment bay 52 is navigated to a target site in a patient.

In some examples, second electrode 92 may be located outside of recess 74 of deployment bay 52. For example, second electrode 92 may be secured to an outer surface of outer wall 76 of deployment bay 52. In other examples, second electrode 92 may be secured to an outer surface of a distal portion of elongated member 54, or second electrode 92 may be secured to a transition between elongated member 54 and deployment bay 52. Alternatively (or additionally as described below), second electrode 92 may be located within recess 74 of deployment bay 52. For example, second electrode 92 may be secured to proximal portion 100 of IMD 16A. Similar to first electrode 90, second electrode 92 may be configured to be exposed to a fluid of patient 14 when deployment bay 52 is navigated to a target site in patient 14.

Both first electrode 90 and second electrode 92 may be electrically coupled to circuitry 94. Delivery device 50 may include one or more conductors configured to electrically couple first electrode 90 and second electrode 92 to circuitry 94. For example, turning back to FIG. 2B, first conductor 102A and second conductor 102B (collectively, "conductors 102") may extend longitudinally throughout delivery device 50 embedded in wall of elongated member 54. First conductor 102A may be coupled to first electrode 90 and second conductor 102B may be coupled to second electrode 92. In other examples (not depicted), one or both of conductors 102 may be embedded within deployment mechanism 66 or may be configured to extend within a lumen of (rather than be embedded within) elongated member 54. For example, one or both of conductors 102 may extend longitudinally within lumen 64 of elongated member 54.

Conductors 102 may be electrically insulated from each other as they extend longitudinally through delivery device 50. In other examples (e.g., where circuitry 28 of IMD 16A comprises some or all of circuitry 94 as described herein), conductors 102 may extend entirely or partially within IMD 16A to coupled circuitry 94 to first electrode 90 and second electrode 92.

Turning back to FIG. 2A, as depicted circuitry 94 may be located within delivery device 50. For example, circuitry 94 may be located within hub 56 of delivery device 50. In other examples, circuitry 94 may be within a separate housing that may be coupled to delivery device 50. For example, circuitry 94 may be contained within an enclosure that may be coupled to delivery device 50 (e.g., coupled to ports of hub 56 in such a way that circuitry 94 of the enclose is electrically coupled to conductors 102 and therein first electrode 90 and second electrode 92 of delivery device 50). Alternatively, some of all of circuitry 94 may be included in circuitry 28 of IMD 16A as depicted in FIG. 1A. For example, first electrode 90 may be on distal tip 96 of IMD 16A, second electrode 92 may be secured to proximal portion 92 of IMD 16A, and circuitry 94 may be within a hermetically sealed housing of IMD 16A, such that techniques for verifying a fixation of IMD 16A to the target site are executed by components solely of IMD 16A.

Circuitry 94 may include circuitry configured to deliver an electrical signal to fluid and/or tissue along a path between first electrode 90 and second electrode 92. For example, circuitry 94 may be configured to couple first electrode 90 to a positive or supply terminal of an energy supply and couple second electrode 92 to a negative or return terminal of an energy supply. In this way, circuitry 92 may create an electrical circuit when a conductive medium such as tissue or fluid is provided on the path between first and second electrodes 90, 92. The path may include fluid and/or tissue at the target site of patient 14. In some examples (e.g., where circuitry 94 uses a power source such as a battery to generate the electrical signal), circuitry 94 may be configured to maintain a substantially static voltage potential or a substantially static current across first electrode 90 and second electrode 92 (through substantially static voltage potentials are predominantly discussed herein for purposes of clarity). This static voltage or current may be provided in a sinusoidal or pulse format. As a result of first electrode 90 and second electrode 92 delivering an electrical signal with a substantially static voltage potential or current, a value of the impedance of the signal may be reliably correlated to changes in the materials of the path. Put differently, as a result of providing a known and/or constant voltage, a resistance of the path traveled by the signal may be calculated by measuring the current, and alternatively as a result of providing a known and/or constant current, a resistance of the path may be calculated by measuring the voltage. For example, tissue of patient 14 may have relatively higher electrical resistance than fluid of patient 14, such that an impedance of the signal may increase when the electrical signal passes through tissue rather than just fluid of patient 14.

Circuitry 94 may identify an impedance of the electrical signal. Internal signal 94 may determine when the impedance indicates that the deployment bay 52 and/or IMD 16A define one or more fixation configurations. For example, circuitry 94 may cause first electrode 90 within deployment bay 52 and second electrode 92 secured to outer surface of deployment bay 52 to delivery electrical signal to fluid of patient 14 that is between first and second electrodes 90, 92. When distal surface 80 of deployment bay 52 that defines distal opening 78 is not flush against tissue of patient 14 (e.g., such that fluid of the patient 14 can flow into and out of recess 74 through distal opening 78), the electrical signal may follow a path that does not pass through any tissue of patient 14. Circuitry 94 may be configured to identify that the impedance of the electrical signal is lower than a predetermined threshold value (e.g., a level that indicates that the electrical signal has passed through tissue). Similarly, when distal surface 80 of deployment bay 52 is flush against tissue of patient 14, the path of the electrical signal may go through at least some tissue (e.g., as a result of fluid of the patient 14 being trapped in deployment bay 52). As a result of the path including at least some tissue, an impedance of the electrical signal between first electrode 90 inside recess 74 and second electrode 92 outside of recess 74 may increase. Circuitry 94 may identify that the impedance of the electrical signal has raised above the impedance threshold, indicating that the distal surface 80 of the deployment bay 52 is flush (substantially or adequately) against the target site, and therein deployment bay 52 is defining a first fixation configuration.

Figure 4A:
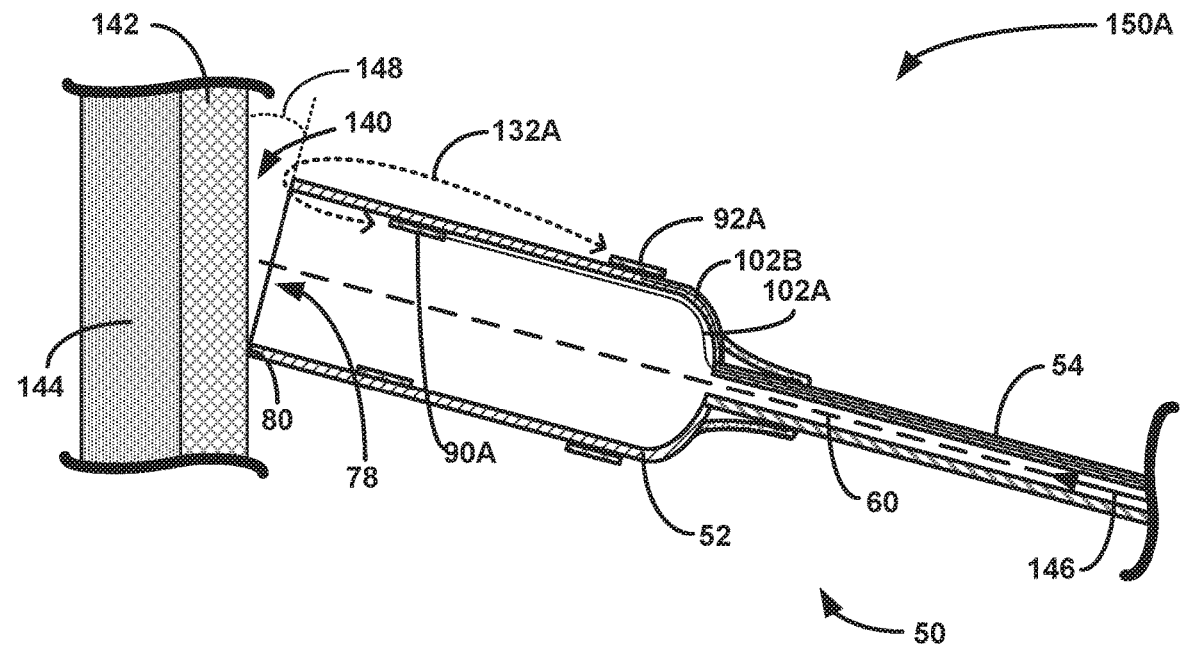
FIG. 4A is a conceptual diagram illustrating a side view of the delivery device of FIG. 2A defining a first non-fixation configuration relative to a target site.
Figure 4B:
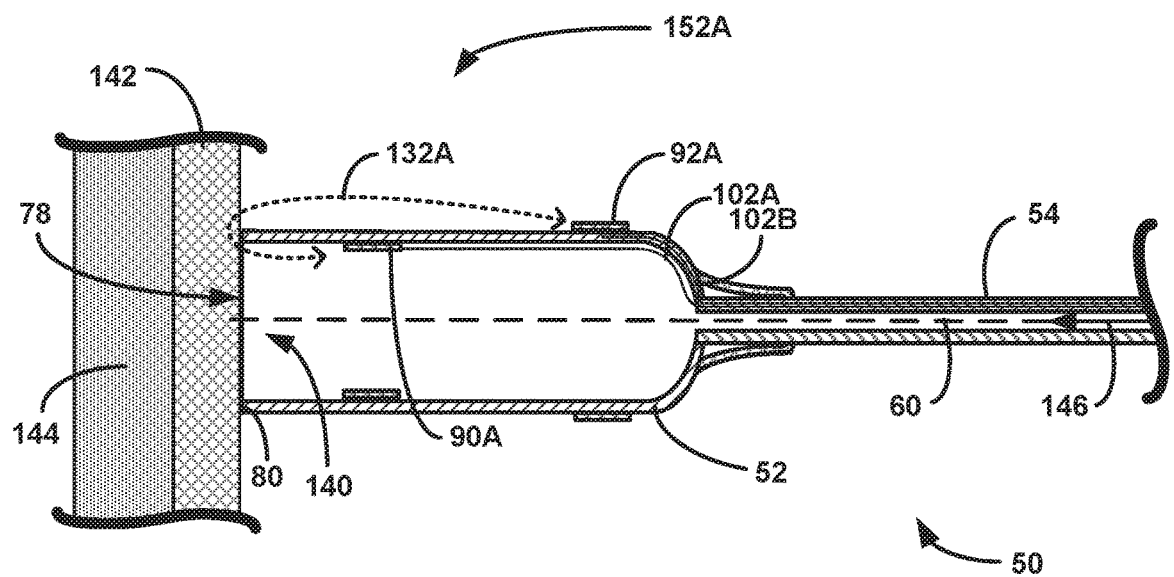
FIG. 4B is a conceptual diagram illustration a side view of the delivery device of FIG. 2A defining a first fixation configuration relative to a target site.

As a result of deployment bay 52 defining a first fixation configuration, circuitry 94 may cause user interface 104 to indicate the realization of the first fixation configuration (e.g., first fixation configuration 152A as depicted in FIG. 4B). User interface 104 may include an interface that is configured to present information or data or feedback to a user such as a clinician. For example, user interface 104 may include a display screen, a speaker or other device capable of provide audible feedback, or a haptic device. Where user interface 104 is a display screen, circuitry 94 may be configured to cause user interface 104 to present current impedance values to a clinician (e.g., by displaying text or imagery that indicates a successful first fixation configuration and/or a non-successful first fixation configuration, and/or one or more transformations between the two). In some examples, user interface 104 may be located on programmer 18 of FIGS. 1A and 1B, such as where user interface 104 is a display of programmer 18 and circuitry 94 communicates with user interface 104 using telemetry techniques as described herein.

Alternatively, or additionally, user interface 104 may be located on a proximal portion of delivery device 50. For example, user interface 104 may be located on hub 56 of delivery device 50. Where circuitry 94 is located on a separate device as described herein, user interface 104 may be located on the same device. In some examples, user interface 104 may include a light such as a light-emitting diode (LED) or the like. For example, where user interface 104 includes an LED, circuitry 94 may be configured to cause LED to display a first predetermined color (e.g., red) in response to identifying that the impedance of the electrical signal is below the threshold level (e.g., such that deployment bay 52 does not define the first fixation configuration) and subsequently display a second predetermined color (e.g., green) in response to identifying that the impedance of the electrical signal rises above the threshold level (e.g., as a result of deployment bay 52 defining the first fixation configuration relative to the target site), flipping back and forth between the two in response to changing impedance levels.

Alternatively, or additionally, circuitry 94 may be configured to verify when an electrical signal between first electrode 90 and second electrode 92 indicates that IMD 16A defines a second fixation configuration with tissue of a target site of patient 14. For example, first electrode 90 may be secured to distal tip 96 of IMD 16A, and second electrode 92 may be secured to an outer surface of outer wall 76 of deployment bay 52. As discussed herein, first electrode 90 may be configured to press into tissue at the target site of patient 14 upon deployment from deployment bay 52. In some examples, the target site may be a target site at or within heart 12 of patient 14.

In some examples where the target site is at or within heart 12 of patient 14, a manner in which IMD 16A presses into heart 12 may impact an efficacy of treatment and/or monitoring provided by IMD 16A. For example, where IMD 16A is deployed from deployment bay 52 such that only one of fixation elements 82 becomes secured to target site, first electrode 90 may not press into tissue "square" such that one side of first electrode 90 is not contacting the tissue, or first electrode 90 may be pressed into the tissue with less than a threshold force such that signals between tissue and first electrode 90 are not passed efficaciously. When IMD 16A is deployed such that first electrode 90 on distal tip 90 of IMD 16A does not press into tissue as desired, it may be difficult or impossible for IMD 16A to provide monitoring, pacing, or defibrillation techniques as desired. Circuitry 94 may be configured to verify when fixation elements 82 cause first electrode 90 to press into tissue of the target site squarely (e.g., straight-on such that a longitudinal axis of IMD 16A is at a right angle with a surface of the target site) with at least a threshold force.

For example, circuitry 94 may analyze a "stability" or a "clarity" of an impedance of the electrical signal passed between first electrode 90 and second electrode 92, where stability or clarity indicate a smooth and nonvolatile set of slopes of the impedance waveform as discussed herein. Put differently, as a result of IMD 16A being deployed near or within heart 12, an impedance of the electrical signal as sent between a path of tissue and fluid between first and second electrodes 90, 92 may reflect and/or incorporate intrinsic waveforms of heart 12 (e.g., electrocardiography waveforms, phase waveforms, pressure waveforms). The impedance of the electrical signal as detected by circuitry 94 may reflect these intrinsic waveforms with more "clarity" or with "noise" (e.g., noise being series of relatively non-smooth slopes between repeated peaks and valleys of a waveform, and/or a bimodal signature within the waveform) depending upon the quality of the deployment of IMD 16A from deployment bay 52. Further, circuitry 94 may be configured to isolate or highlight this noise or clarity. For example, circuitry 94 may be configured to determine a first derivative of the impedance values, such that any noise may be magnified and therein be easier to identify. Additionally, or alternatively, circuitry 94 may be configured to execute fast Fourier transform (FFT) algorithms over the impedance values to isolate specific frequency components of the signal, therein analyzing these frequency components for noise or clarity. Further, circuitry 94 may be configured to identify an amount of lag between the current and the voltage across the electrodes 90, 92 to identify a phase of the impedance of the electrical signal, and therein identify if the phase waveform satisfies various noise thresholds as described herein.

When IMD 16A is deployed in such a manner that first electrode 90 on distal tip 96 of IMD 16A presses loosely or at an angle into tissue of the target site, the impedance of the electrical signal as identified by circuitry 94 may be relatively noisy. Conversely, where IMD 16A is deployed such that first electrode 90 on distal tip 96 presses squarely with at least a threshold force into tissue of the target site, the impedance waveform as identified by circuitry 94 repeatable, predictable, and may be maintain a magnitude. In some examples, a clinician may determine that IMD 16A defines a second fixation configuration when circuitry 94 indicates that an impedance waveform maintains a relatively static and stable waveform upon (such that the impedance waveform does not acquire a bimodal signature or define slopes that are too noisy to be within a predetermined slope threshold) even when the IMD 16A is tugged upon deployment.

As a result of circuitry 94 determining that an impedance indicates that IMD 16A defines the second fixation configuration, circuitry 94 may cause user interface 104 to indicate the realization of the second fixation configuration. For example, where user interface 104 is an LED, circuitry 94 may be configured to cause LED to display a predetermined color (e.g., blue) in response to identifying that the impedance waveform is stable and relatively static (e.g., as a result of IMD 16A defining the second fixation configuration relative to the target site). Alternatively, where user interface 104 is a display screen (e.g., where external device 18 comprises user interface 104), circuitry 94 may be configured to cause user interface 104 to present impedance waveforms and/or noise levels to a clinician, along with a "pass" or "fail" message.

In some examples, delivery device 50 may include one or more radiopaque elements that may indicate a location of deployment bay 52 within patient. For example, deployment bay 52 may include radiopaque elements that enable a clinician monitoring an intravenous navigation of delivery device 50 to determine when deployment bay 52 has arrived at a target site. A clinician may track a location of deployment bay 52 using various fluoroscopy techniques. Radiopaque element may be secured to elongated member 54 at a location immediately proximal to deployment bay 52, and/or radiopaque elements may be secured to deployment bay 52. Radiopaque elements include a band of radiopaque materials that are embedded within delivery device 50, a band that runs along an outer circumference of a portion of delivery device 50, a doped portion of delivery device 50 (e.g., relative to adjacent portions), or the like. In other examples, a clinician may track a location of deployment bay 52 using materials of IMD 16A. For example, a clinician may track a progress of an electrode on distal tip 96 of IMD 16A to track a location of deployment bay 52.

As discussed above, delivery device 50 may include two or more electrodes. For example, as depicted in the conceptual diagram of FIG. 2C illustrating a side view of delivery device 50 with IMD 16A out of deployment bay 52, deployment bay 52 may include one pair of first electrode 90A and second electrode 92A while IMD 16A includes a second pair of first electrode 90B and second electrode 92B. First electrode 90A may include a conductive material that is secured to an inner surface of outer wall 76 of deployment bay, and second electrode 92A may include a conductive material that is secured to an outer surface of outer wall 76 of deployment bay 52. First electrode 90A may only expose a conductive material to the inner surface of deployment bay 52, while second electrode 92A only exposes a conductive material to the outer surface of deployment bay 52. Additionally, first electrode 90B may be secured to distal tip 96 of housing of IMD 16A, while second electrode 92B is secured to proximal portion 100 of IMD 16A. Both first electrodes 90A, 90B may be substantially similar to first electrode 90 with the exception of any differences described herein. Similarly, both second electrodes 92A, 92B may be substantially similar to second electrode 92 as described herein with the exception of any differences described herein.

Circuitry 94 may be configured to provide a first electrical signal between first electrode 90A and second electrode 92A of deployment bay to determine if deployment bay 52 defines a first fixation configuration. Additionally, circuitry 94 may be configured to provide a second electrical signal between first electrode 90B and second electrode 92B of IMD 16A to determine if IMD 16A defines second fixation configuration. In some examples, a different set of circuitry 94 may provide and analyze first electrical signal as provides and analyzes second electrical signal. For example, first set of circuitry 94 may reside in hub 56 of delivery device 50, while circuitry 28 of IMD 16A may comprise second set of circuitry 94. Alternatively, in some examples a single set of circuitry 94 may provide and analyze both first electrical signal between first and second electrodes 90A, 92A of deployment bay 52 as well as second electrical signal between first and second electrodes 90B, 92B of IMD 16A.

Alternatively, in some examples, delivery device 50 may include one common electrode that sends a signal to two (or more) other electrodes to verify fixation configurations. For example, as depicted in the conceptual diagram of FIG. 2D illustrating a side view of delivery device 50 with IMD 16A out of deployment bay 52, deployment bay 52 may include one pair of first electrode 90A and second electrode 92A while IMD 16A includes a second version of first electrode 92A. Circuitry 94 of delivery device 50 may be configured to provide a first electrical signal between first electrode 90A of deployment bay and second electrode 92A to determine if deployment bay 52 defines a first fixation configuration, as well as being configured to provide a second electrical signal between first electrode 90B of IMD 16A and second electrode 92A to determine if IMD 16A defines second fixation configuration. Put differently, in some examples a common electrode (here, second electrode 92) may be configured to provide an electrical signal to two different paths between two different electrodes (here, first electrode 90A and first electrode 90B).

In some examples, delivery device 50 may be configured to use first electrode 90B and second electrode 92B of IMD 16A to both verify a first and a second fixation configuration. For example, as depicted in the conceptual diagram of FIG. 2E illustrating a side view of delivery device 50 with IMD 16A housed within deployment bay 52, deployment bay 52 may include define one or more holes 86A through outer wall 76 of deployment bay 52 while IMD 16A includes first electrode 90B and second electrode 92B. One or more holes 86A of deployment bay 52 may extend radially through outer wall 76. One or more holes 86A may be configured to enable blood to flow through holes 86A to access second electrode 92B. In some examples, one or more holes 86A may be located along deployment bay 52 at a location that is adjacent where second electrode 92B may be located when IMD 16A is housed within deployment bay 52. As depicted, deployment bay 52 may define a plurality of holes 86A at a plurality of radial and longitudinal locations. Further, in some examples IMD 16A may be configured to generally engage an inner surface of outer wall 76 of deployment bay (e.g., such that an outer diameter of IMD 16A is only nominally smaller than an inner diameter of deployment bay 52), such that it is difficult for fluid to flow within deployment bay 52 between first electrode 90B and second electrode 92B. Rather, for fluid to flow between first electrode 90B and second electrode 92B, such fluid may flow out of distal opening 74 and then through one of one or more holes 86A to define such a path. Circuitry 94 of delivery device 50 (e.g., which may be included within circuitry 28 of IMD 16A) may be configured to provide a first electrical signal between first electrode 90B and second electrode 92B to determine if deployment bay 52 defines a first fixation configuration, as well as being configured to provide a second electrical signal between first electrode 90B of IMD 16A and second electrode 92B to determine if IMD 16A defines second fixation configuration.

In some examples, delivery device 50 may define holes in such a way that the holes are sealed within the delivery device. For example, as depicted in the conceptual diagram of FIG. 2F illustrating a side view of delivery device 50 and FIG. 2G depicting a cross-sectional view through cut plane 106, deployment bay 52 may include one or more ribs 108 that extend in from outer wall 76 to engage IMD 16A. Ribs 108 may be configured to be deformable to radially compress to secure IMD 16A within deployment bay 52 prior to deployment. For example, ribs 108 may be made of a relatively soft and compressible biocompatible material, such as rubber, silicone, LDPE, thermoplastic elastomers, polyethylene (PE), or the like. Ribs 108 may extend longitudinally along a length of deployment bay 52. Deployment bay 52 may define a plurality of ribs 108 at different longitudinal and radial locations. In some examples, deployment bay 52 may include a plurality of ribs 108 that are radially arranged around inner surface of outer wall 76 of deployment bay 52. For example, as depicted deployment bay 52 may include four separate ribs 108 that are all equally spaced around longitudinal axis 60 of delivery device 50 at a shared longitudinal location within deployment bay 52 (e.g., such that each of ribs 108 is 90° away from a circumferentially adjacent rib 108). In other examples, deployment bay 52 may include more or less ribs 108 that are radially arranged around longitudinal axis 60, such as three ribs 108 that are 120° away from each other, or five ribs 108 that are each approximately 72° away from circumferentially adjacent ribs 108. Ribs 108 may be adhesively bonded or otherwise fixedly attached to an inner surface of outer wall 76 of deployment bay 52.

Delivery device 50 may include one or more holes 86B that are substantially similar to holes 86A with the exception of any differences described herein. As depicted in FIGS. 2F and 2G, each of holes 86B may be aligned with one of ribs 108. Holes 86B may radially extend in through both outer wall 76 and ribs 108. Though FIG. 2G depicts holes 86B extending through only one of ribs 108, in other examples holes 86B may extend through more or all of ribs 108.

As a result of ribs 108 extending in to engage IMD 16A, holes 86B are sealed against second electrode 92B. As a result of ribs 108 sealing second electrode 92B within deployment bay 52 such that second electrode 92B is only exposed to fluid of patient when inserted in patient, circuitry 94 as discussed herein may identify more pronounced impedance changes as a result of deployment bay 52 defining a first fixation configuration as described herein. As a result of impedance changes being more pronounced, delivery device 50 may be relatively more likely to correctly determine when the deployment bay 52 is or isn't defining a fixation configuration, therein improving a likelihood that IMD 16A is deployed in an efficacious manner.

Further, in some examples holes 86A, 86B (collectively, "holes 86") may improve a manner in which deployment bay 52 is withdrawn from patient 14. For example, as deployment bay 52 is withdrawn from patient 14 (e.g., following the deployment of IMD 16A), distal opening 74 may create a relatively negative pressure within deployment bay 52 that pulls some fluid or tissue of patient into deployment bay 52. Once deployment bay 52 is fully withdrawn out of patient 14 (e.g., through an introducer sheath or the like) this relatively negative pressure may stabilize, causing any fluid or tissue that has been pulled into deployment bay 52 to be leaked or ejected from deployment bay 52. Holes 86 may improve an ability of pressure within deployment bay 52 to normalize (e.g., be relatively equal within and outside of deployment bay 52) as deployment bay 52 is withdrawn from patient, therein reducing or elimination a vacuum effect that may pull fluid or tissue into deployment bay 52. Reducing or eliminating this vacuum effect may reduce or eliminate the likelihood that deployment bay 52 gathers and then leaks and/or ejects patient 14 fluid or tissue as a result of withdrawing deployment bay 52 from patient 14.

Figure 2H:
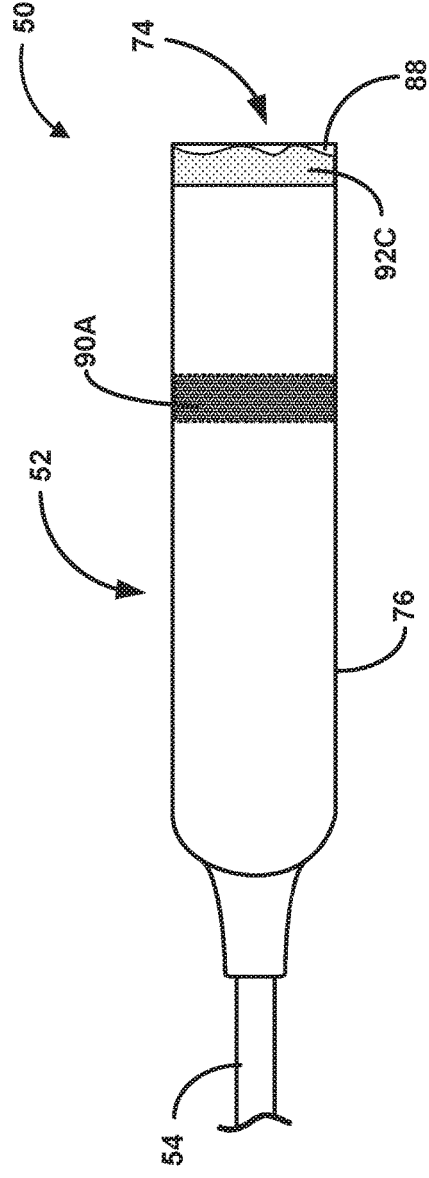
FIG. 2H is a conceptual diagram illustrating an example first electrode in the deployment bay and a second electrode on the distal tip of the deployment bay of FIG. 2A for verifying if the deployment bay is defining a first fixation configuration.

In some examples, delivery device 50 may be configured to verify when deployment bay 52 presses into tissue of a patient with a threshold amount of force. For example, as depicted in the conceptual diagram of FIG. 2H illustrating a side view of delivery device 50, deployment bay 52 may include first electrode 90A within deployment bay 52 and second electrode 92C at a distal tip of deployment bay 52. First electrode 90A may be secured to an inner surface of deployment bay 52 and/or a first electrode may be secured to IMD 16A (e.g., such that first electrode 90B is used with second electrode 92C).

In some examples, second electrode 92C may be "masked" with a non-conductive material 88 near the distal tip of the deployment bay 52. Non-conductive material 88 may be any material that does not conduct electricity well. For example, non-conductive material 88 may include an adhesive that is applied to the outer surface of second electrode 92C. The region of second electrode 92C that is masked by non-conductive material 88 may include most or all of second electrode 92 that is immediately adjacent (e.g., within approximately 1 millimeter of) distal surface 80 of deployment bay 52. Though region that is masked by non-conductive material 88 is depicted as masking an uneven portion of second electrode 92C, in other examples a distal edge second electrode 92C may be uniformly masked by non-conductive material 88.

As a result of non-conductive material 88 masking second electrode 92C, a conductive surface of second electrode 92C may not contact tissue of a target site when deployment bay 52 initially contacts the tissue of the target site. Thus, when deployment bay 52 initially contacts but does press into tissue of the target site, the electrical signal may include fluid between first electrode 90A and tissue of the target site and fluid between second electrode 92C and tissue of the target site. If a clinician provides a further distal force on delivery device 50, deployment bay 52 may press into tissue of the target site with sufficient force for the tissue to deform up around outer wall 76 of deployment bay 52 and contact a conductive surface of second electrode 92C that is not masked by non-conductive material 88. Thus, an electrical signal between first electrode 90A and second electrode 92C may include fluid between first electrode 90 and tissue and then tissue between this fluid and second electrode 92C (e.g., and not include any fluid between second electrode 92C and tissue). Circuitry 94 of delivery device 50 may be configured to identify when an impedance of the electrical signal changes as a result of a non-masked portion of second electrode 92C contacting tissue of the target site. Where it is advantageous for deployment bay 52 to press into tissue with at least a threshold amount of force prior to deploying IMD 16A, circuitry 94 may indicate when the impedance of the electrical signal rises above a threshold level that indicates this threshold amount of force such that deployment bay 52 defines a first fixation configuration.

Figure 2I:
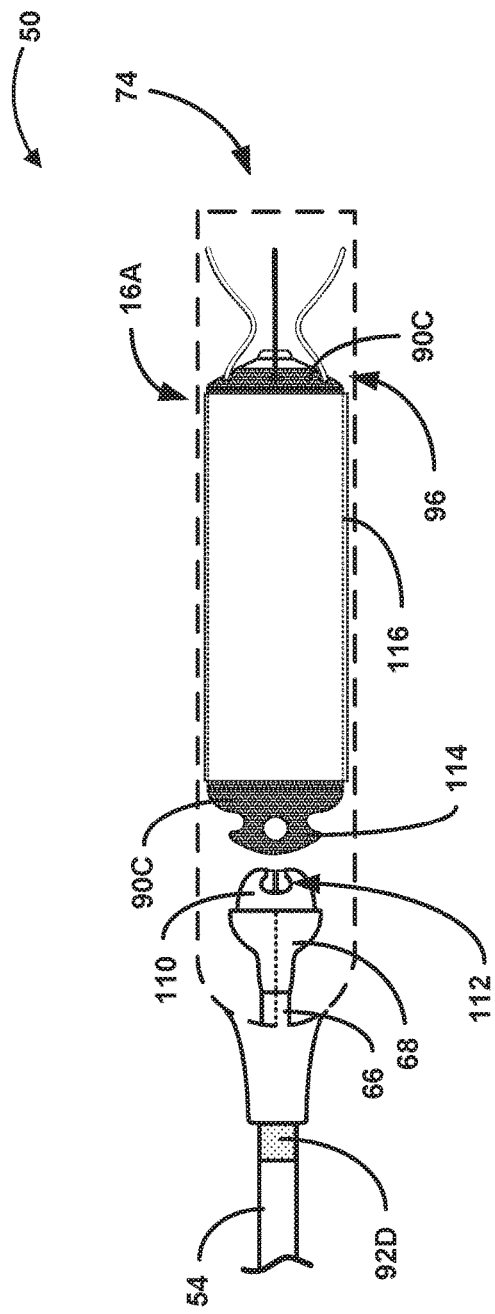
FIG. 2I is a conceptual diagram illustrating an example first electrode comprised of the metal can of an IMD and a second electrode on the elongated member of the delivery device of FIG. 2A for verifying if the deployment bay is defining a first fixation configuration.

In some examples, circuitry 94 of delivery device 50 may couple to a proximal portion of a metallic conductive can of IMD 16A (e.g., the housing of IMD 16A) to create a first electrode at a distal portion of IMD 16A. For example, FIG. 2I is a conceptual diagram illustrating an example first electrode 90C comprised of the metal can of IMD 16A and second electrode 92D on elongated member 54 of delivery device 50. Second electrode 92D may be substantially similar to second electrodes 92A, 92B, 92C with the exception of any differences described herein. Second electrode 92D may be secured to an outer surface of a distal portion of elongated member 54 and may be configured to be exposed to fluid of patient 14 when deployment bay 52 is navigated to a target site. Further, delivery device 50 may include clamp 110 that includes teeth 112. Clamp 110 may be configured to be slideable within deployment mechanism 66 of delivery device 50. Specifically, clamp 110 may be configured to be longitudinally moveable within a lumen of deployment mechanism 66, such that teeth 112 of clamp 110 may close down on proximal catch 114 of IMD 16A. Teeth 112 may be actuatable (e.g., openable or closeable) as controlled by a clinician. For example, a clinician may actuate teeth 112 of clamp 110 open or close from a control mechanism for deployment mechanism 66 on or adjacent hub 56 as described above. Though clamp 110 is shown as not engaging proximal catch 114 in FIG. 2I for purposes of clarity, it is to be understood that clamp 110 may engage proximal catch 114 until IMD 16A is verified (e.g., by circuitry 94) as discussed herein to be securely fixed to the target site.

In some examples, clamp 110 and teeth 112 may be electrically coupled to a power source. For example, second electrode 92D may be electrically coupled to a first terminal of a power source while clamp and teeth are electrically coupled to a second terminal of the same power source. As such when teeth 112 closes on proximal catch 114 of a metal can of IMD 16A, the metal can may be electrically coupled to the second terminal of the power source, such that the metal can is first electrode 90C.

In some examples, some or most of IMD 16A may include coating 116. Coating 116 may include an electrically insulative material. For example, some or most of IMD 16A may be coated with coating 116 that includes a chemical-vapor-deposited material such as poly-para-xylylene, specifically Parylene. Part of coating 116 may be stripped away near proximal catch 114 and distal tip 96. The amount of IMD 16A that is covered by coating 116 is depicted for purposes only, as it is to be understood that more or less of IMD 16A may be covered by coating 116 in other examples. In some examples, it may be advantageous to maximize an amount of IMD 16A that is covered by coating 16A to better electrically insulate IMD 16A and therein potentially improve a battery life of power source of IMD 16A.

Teeth 112 of clamp 110 may engage proximal end 100 proximal catch 114 to "light up" the metallic can of IMD 16A (e.g., electrically couple can under insulative coating 116 to the power source). In this way, a surface of the metallic can near distal tip 96 of IMD 16A acts as a first electrode 90C as described herein, such that circuitry 94 may analyze impedance across a path between first electrode 90C out of distal opening 74 of deployment bay 52 to second electrode 92D on distal portion of elongated member 54.

In some examples, as described herein, a second electrode may not be directly affixed to deliver device 50 but may instead by a patch electrode or a subcutaneous electrode or the like. For example, delivery device 50 may not include second electrode 92D, but rather a second electrode may include a patch electrode on the skin of patient 14 or a subcutaneous electrode in a subcutaneous pocket of patient 14. This second electrode may be a return electrode that is coupled to the power source. Circuitry 94 as described herein may calculate an impedance of an electrical signal between first electrode 90C and this second electrode to verify if deployment bay 52 defines a fixation configuration.

Figure 3:
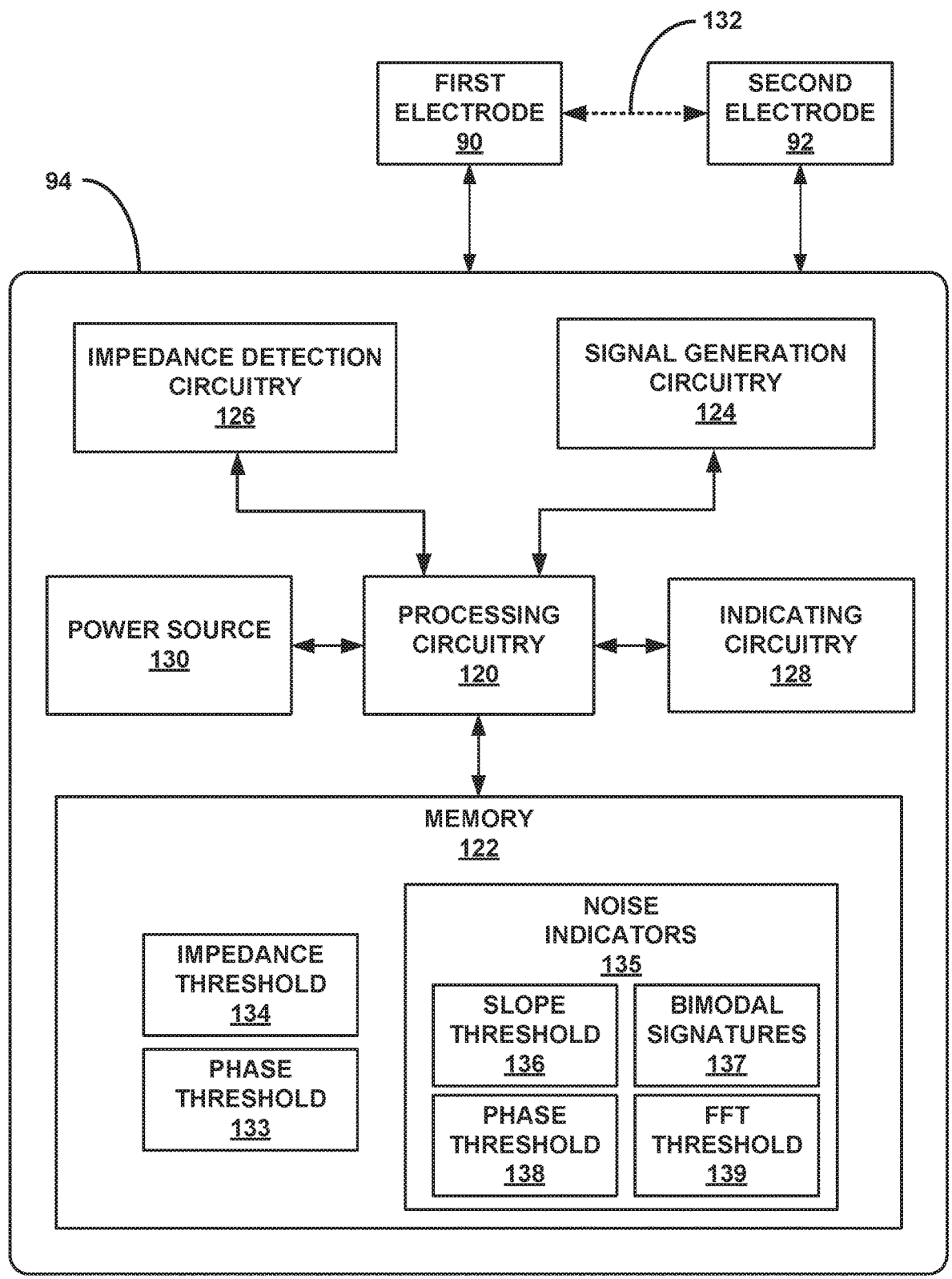
FIG. 3 is a conceptual block diagram illustrating example configuration of circuitry of a system including a delivery device, the circuitry configured to verify when a delivery device and/or IMD define one or more fixation configurations.

FIG. 3 shows a schematic block diagram of circuitry 94 that may be used with any of the devices described herein to verify whether a deployment bay and/or an IMD defines a first and/or second fixation configuration as described herein as identified by sending and analyzing an electrical signal between a first and second electrode. Though FIG. 3 depicts circuitry 94 as a set of blocks for purposes of illustration, it is to be understood that circuitry 94 may include any number of current sources, regulators, oscillators, transistors, capacitors, or the like. Further, through circuitry 94 of FIG. 3 is primarily discussed below in relation to delivery device 50 and corresponding first electrode 90 and second electrode 92 as in FIG. 2A for purposes of clarity, it is to be understood that circuitry 94 of FIG. 3 may additionally or alternatively be comprised within circuitry 28 of IMD 16A in some examples. Circuitry 94 includes processing circuitry 120, memory 122, signal generation circuitry 124, impedance detection circuitry 126, indicating circuitry 128, and power source 130.

Processing circuitry 120, may include any one or more microprocessors, controllers, digital signal processors (DSPs), application specific integrated circuits (ASICs), field-programmable gate arrays (FPGAs), discrete logic circuitry, or any processing circuitry configured to perform the features attributed to processing circuitry 120. The functions attributed to circuitry described herein, including processing circuitry 120, signal generation circuitry 124, impedance detection circuitry 126, and indicating circuitry 128, may be provided by a hardware device and embodied as software, firmware, hardware, or any combination thereof.

Memory 122 may include any volatile or non-volatile media, such as a random-access memory (RAM), read only memory (ROM), non-volatile RAM (NVRAM), electrically erasable programmable ROM (EEPROM), flash memory, and the like. Memory 122 may store computer-readable instructions that, when executed by circuitry of circuitry 94, cause circuitry 94 to perform various functions described herein. Memory 122 may be considered, in some examples, a non-transitory computer-readable storage medium including instructions that cause one or more processors, such as, e.g., processing circuitry 120, to implement one or more of the example techniques described in this disclosure. The term "non-transitory" may indicate that the storage medium is not embodied in a carrier wave or a propagated signal. However, the term "non-transitory" should not be interpreted to mean that memory 122 is non-movable. As one example, memory 122 may be removed from delivery device 50 and moved to another device. In certain examples, a non-transitory storage medium may store data that can, over time, change (e.g., in RAM).

Processing circuitry 120 is configured to cause signal generation circuitry 124 to generate and deliver the electrical signal to tissue of patient 14 along path 132 between first electrode 90 and second electrode 92. Signal generation circuitry 124 includes electrical signal generation circuitry such as a current source (e.g., a current mirror coupled to power source 130 and some transistors) and is configured to generate and deliver an electrical signal in the form of a known and/or constant voltage potential or current across first electrode 90 and second electrode 92 (e.g., such that, whatever the waveform of the electrical signal, signal generation circuitry 124 may compensate for impedance such that an amplitude of the electrical signal may remain consistent, though it may vary over time as intended in a predetermined manner). For example, the signal may include 100 microamps and may be between 8 kilohertz and 100 kilohertz.

In some examples, delivery device 50 may be configured such that conductors as described herein are independently coupled to one or more electrodes. For example, delivery device 50 may be configured to verify that distal surface 80 defining distal opening 78 of deployment bay 52 is defining a first fixation configuration with first electrode 90A within recess 74 and second electrode 92A secured to outer surface of outer wall 76 of deployment bay 52. Additionally, delivery device 50 may be configured to verify that IMD 16A is defining a second fixation configuration with first electrode 90B at distal tip 96 of IMD 16A and an alternate second electrode 92B on an outer surface of proximal portion 100 of IMD 16A. In such examples, processing circuitry 120 may control signal generation circuitry 124 to generate and deliver different electrical signal via different combinations of conductors and/or electrodes (e.g., to an initial second electrode 92A located outside of recess 74 and an alternate second electrode 92 on proximal portion 100 of IMD 16A). In these examples, circuitry 94 may include a switching circuitry to switch the delivery of the electrical signal between different pairs of first and second electrodes 90, 92 (e.g., switched as controlled by processing circuitry 120).

Impedance detection circuitry 126 may be configured to identify and analyze an impedance of the electrical signal sent across path 132 between first electrode 90 and second electrode 92. As described herein, an impedance may change depending upon a location of deployment bay 52 and IMD 16A relative to tissue of the target site. For example, an impedance may increase when path 132 includes tissue rather than just fluid of patient 14, and an impedance may reflect intrinsic waveforms of heart 12 with more or less noise and/or stability depending upon how well first electrode 90 is seated against tissue of the target site. Impedance detection circuitry 126 may be configured to isolate and identify this impedance.

Impedance detection circuitry 126 may identify impedance levels by including sample and hold circuitry to sample the voltage drop across the resistance. Using this voltage drop, impedance detection circuitry 126 may calculate the impedance. Impedance detection circuitry 126 may sample the voltage drop with a sampling rate that is sufficiently high enough to reliably identify the impedance signal. For example, impedance detection circuitry 126 may sample the voltage rate with a sampling rate around 1000 hertz.

Once impedance detection circuitry 126 determines an impedance, processing circuitry 120 may determine whether or not these impedance characteristics indicate that the deployment bay 52 and/or IMD 16A define the first or second fixation configuration relative to tissue of the target site. Though processing circuitry 120 is discussed herein as analyzing "raw" or otherwise unmanipulated impedance data, it is to be understood that processing circuitry 120 may execute one or more operations prior to determining whether or not the impedance data indicates the first or second fixation configuration. For example, processing circuitry 120 may identify one or more derivatives of impedance data prior to and/or in addition to executing the functionality discussed herein. Being as derivatives may highlight any sudden changes in impedance data over time, the use of identifying and analyzing derivative data may improve an ability of processing circuitry 120 to identify fixation configurations and/or non-fixation configurations For example, processing circuitry 120 may determine whether or not the electrical signal as generated and delivered by signal generation circuitry 124 to path 132 between first electrode 90 and second electrode 92 results in an impedance that is above impedance threshold 134 as stored in memory 122. Impedance threshold 134 may include a static value where a momentary spike is sufficient for impedance detection circuitry 126 to determine that deployment bay 52 has defined a first fixation configuration. Alternatively, impedance threshold 134 may include an average impedance magnitude over a period of time (e.g., over 1 or two seconds).

Additionally, or alternatively, processing circuitry 120 may be configured to identify an amount that the current leads or lags the voltage across path 132 in order to identify a phase of heart 12 from the impedance. Processing circuitry 120 may identify whether or not the phase satisfies phase threshold 133 as stored in memory 122. In some examples, processing circuitry 120 may be configured to determine whether the identified phase satisfies a plurality of phase thresholds 133 as relate to whether deployment bay 52 is generally contacting or pressing into tissue of a target site as discussed herein. Further, processing circuitry 120 may be configured to execute FFT on the electrical signal across path 132 to identify various frequency components as reflected in the impedance.

Where the impedance as detected by impedance detection circuitry 126 is above impedance threshold 134 and/or when phase as identified by processing circuitry 120 is above phase threshold 133, processing circuitry 120 may cause indicating circuitry 128 to provide a first fixation configuration indication on user interface 104. Indicating circuitry 128 may include components that can provide an output that is identifiable by a clinician as indicating a fixation or non-fixation configuration. For example, indicating circuitry 128 may include an LED (e.g., such as user interface 104 located on hub 56), a speaker, a haptic feedback device, a screen or the like. Processing circuitry 120 may cause indicating circuitry to provide a predetermined output (e.g., green color on the LED, or a positive ding on the speaker, or a success message on the screen) in response to determining that an impedance indicated a fixation configuration. For another example, indicating circuitry 128 may include telemetry circuitry, and processing circuitry 120 may cause indicating circuitry 128 to provide a message for external device 18 of FIGS. 1A and 1B to display a successful first fixation configuration on a display of external device 18.

For another example, circuitry 94 may be used to determine whether or not IMD 16A defines a second fixation configuration. In such examples, processing circuitry 120 may cause signal generation circuitry 124 to provide a signal to path 132 between electrodes 90, 92 that is similar or different than a signal (and/or path 132, as described herein) used to determine if deployment bay 52 defines a first fixation configuration. Processing circuitry 120 may cause signal generation circuitry 124 to provide a second signal and/or cause impedance detection circuitry 126 to therein identify an impedance with which processing circuitry 120 determines if the second signal indicates that IMD 16A defines a second fixation configuration in response to getting an input (e.g., from clinician) that specifically relates to verifying a second fixation configuration. Alternatively, processing circuitry 120 may cause signal generation circuitry 124 to generate a second signal and then cause impedance detection circuitry 126 to determine an impedance with which processing circuitry 120 determines whether the impedance of the second signal indicates a second fixation configuration automatically in response to impedance detection circuitry 126 identifying an impedance of a first signal that processing circuitry 120 determines is over impedance threshold 134 (such that deployment bay 52 defines a first fixation configuration). In some examples, processing circuitry 120 may cause signal generation circuitry 124 to provide an ongoing first signal and cause impedance detection circuitry 126 to continually determine a real-time impedance level in response to which processing circuitry 120 determines a real-time first fixation or non-fixation configuration. Processing circuitry 120 may cause signal generation circuitry 124 and impedance detection circuitry 126 to provide these ongoing functions and evaluations as signal generation circuitry 124 starts providing the second signal and processing circuitry 120 starts determining if an impedance of the second signal indicates a second fixation configuration (e.g., where different sets of conductors and electrodes provide the signal).

Processing circuitry 120 may determine whether or not the electrical signal as generated and delivered to first electrode 90 and second electrode 92 by signal generation circuitry 124 indicates that IMD 16A defines a second fixation configuration by evaluating an amount of noise in the impedance waveform. Put differently, processing circuitry 120 determines whether or not an impedance waveform of the second signal across path 132 includes and/or satisfies one or more noise indicators 135, or whether an impedance of the second signal is stable and smooth as described herein. Noise indicators 135 as stored in memory 122 and used by processing circuitry 120 include slope threshold 136, bimodal signatures 137, phase threshold 138, and FFT threshold 139.

Figure 8A:
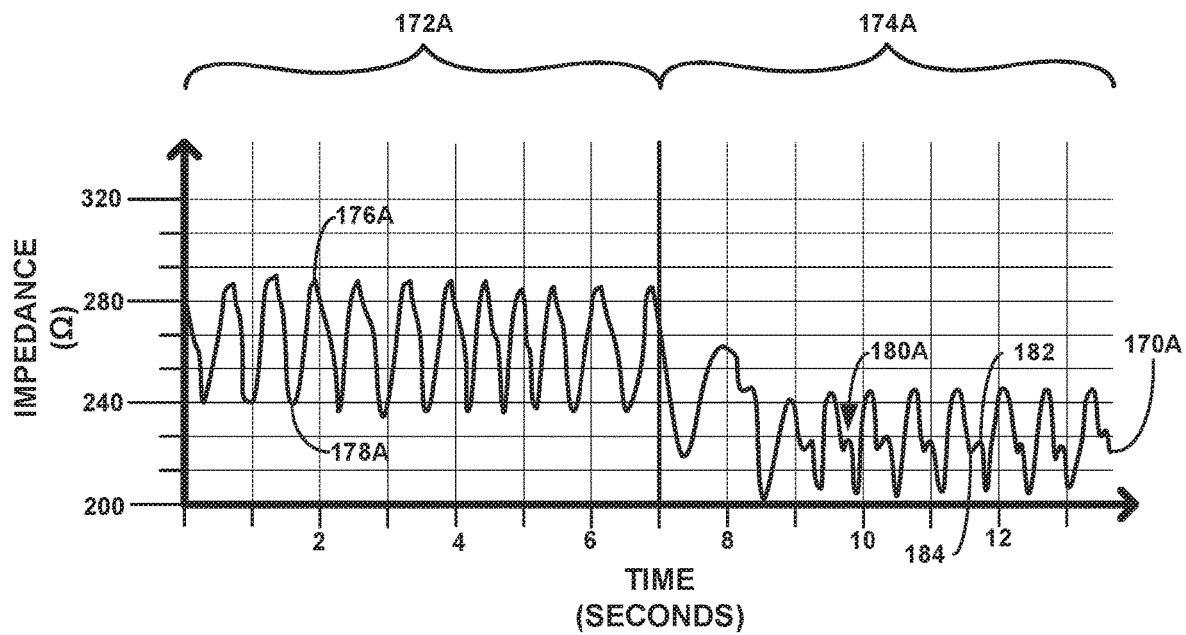
FIG. 8A is a chart of example impedance data that indicates a second non-fixation configuration.
Figure 8B:
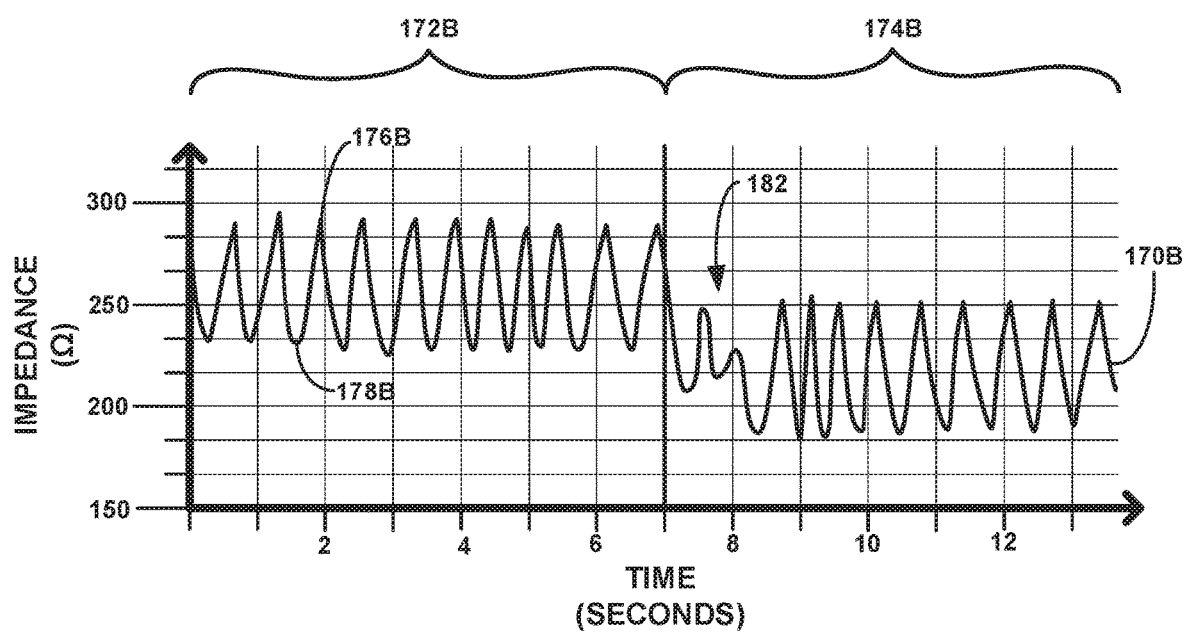
FIG. 8B is a chart of example impedance data that indicates a second fixation configuration.

Slope threshold 136 may include a threshold set of slopes that impedance may include or be within and be identified by processing circuitry 120 as defining a second fixation configuration. For example, a slope may satisfy slope threshold 136 where the slope is substantially smooth (e.g., linear or near-linear) between a peak and a valley of the impedance waveform, such that the slope substantially avoids defining steps, horizontal segments, sharp angles between the peak and the valley, or the like. FIGS. 8A and 8B and the discussion below depict and discuss slopes as may satisfy or fail slope threshold 136. Processing circuitry 120 may determine that the impedance waveform as identified by impedance detection circuitry 126 satisfies slope threshold 136, therein indicating that IMD 16A defines second fixation configuration. In response to this determination, processing circuitry 120 may cause indicating circuitry 128 to indicate a second fixation configuration using user interface 104.

Further, bimodal signatures 137 may include a mini-peak of an impedance waveform in an otherwise generally sinusoidal waveform (e.g., as depicted in FIG. 8A). Processing circuitry 120 may determine that the impedance waveform including bimodal signatures 137 indicates that IMD 16A defines second fixation configuration. In response to this determination, processing circuitry 120 may cause indicating circuitry 128 to indicate a second fixation configuration using user interface 104.

Further, as discussed herein, processing circuitry 120 may identify an amount of noise of the signal by analyzing a relative lag of the current and voltage across path 132. For example, processing circuitry 120 may identify and evaluate a phase of the impedance from the relative lag. Once identified, processing circuitry 120 may determine whether the phase is within phase thresholds 138. Processing circuitry 120 may determine that the phase is within phase thresholds 138 if the waveform of the phase defines relatively static peaks and valleys across the waveform. For example, if each peak is substantially similar (e.g., within 0.2°) to the adjacent peak and each valley is substantially similar (e.g., within 0.2°) to the adjacent valley, the phase may be within phase thresholds 138. Further, processing circuitry 120 may identify whether or not the phase waveform includes bimodal signatures 137 as discussed herein. If processing circuitry 120 determines that the phase waveform satisfies phase threshold 138 and fails to define bimodal signatures 137, impedance detection circuitry may determine that the phase waveform indicates that IMD 16A defines second fixation configuration. In response to this determination, processing circuitry 120 may cause indicating circuitry 128 to indicate a second fixation configuration using user interface 104.

Additionally, as discussed herein, processing circuitry 120 may identify a component of the impedance using FFT. Processing circuitry 120 may use FFT to isolate the frequency components of the signal across path 132. For example, processing circuitry 120 may identify a base frequency that corresponds to a heartbeat of patient 14 as well as a plurality of harmonic frequencies of the signal. Once identified, processing circuitry 120 may identify whether or not the amplitude of any of the identified harmonics satisfy FFT threshold 139 stored in memory 122. FFT threshold 139 may relate to a ratio of the amplitude of one or more harmonic frequencies to the amplitude of the base frequency. For example, FFT threshold 139 may include a ratio between 1:5 and 1:3, such as 1:4, between the first harmonic (e.g., the harmonic with the largest amplitude) and the base frequency. Processing circuitry 120 may be configured to use this FFT threshold 139 of 1:4 to identify that determined FFT data indicates that IMD 16A defines a fixation configuration (e.g., as a result of fixation elements 82 of IMD 16A successfully securing to tissue of the target site) when the amplitude of the first harmonic is less than 25% of the amplitude of the base frequency. Similarly, processing circuitry 120 may using this FFT threshold 139 to identify that FFT data indicates that IMD 16A defines a non-fixation configuration when the amplitude of the first harmonic is greater than 25% of the amplitude of the base frequency.

For another example, FFT threshold 139 may include a ratio between 1:3 and 2:3 between the sum of the amplitudes of the first two, three, or four harmonics (e.g., the 4 harmonics that have the four largest amplitudes) and the base frequency. In certain examples, FFT threshold 139 may include a ratio of 1:2 between the sum of the amplitudes of the first three harmonics and the base frequency. Processing circuitry 120 may be configured to use this FFT threshold 139 to identify that determined FFT data indicates that IMD 16A defines a fixation configuration when the sum of the amplitudes of the first three harmonic is less than 50% of the amplitude of the base frequency. Similarly, processing circuitry 120 may using this FFT threshold 139 to identify that FFT data indicates that IMD 16A defines a non-fixation configuration when the sums of the amplitudes of the first three harmonic is greater than 50% of the amplitude of the base frequency.

Though FFT of the impedance signal is discuss predominantly herein, other Fourier transforms and/or other transforms of other components into the frequency domain may be used in other examples to determine if the signal indicates a fixation or non-fixation configuration. For example, processing circuitry 120 may be configured to analyze an electrogram from a lead inserted/implanted in right ventricle 22, or a surface electrocardiogram from a surface patch, or left ventricle 26 pressure gathered from a pressure sensor inserted/implanted in left ventricle 26 using FFT techniques or other similar transforms. Upon transforming these data signals into a frequency domain, processing circuitry 120 may identify whether certain frequency components of these signals have a magnitude that is greater than a threshold (e.g., where a magnitude above a threshold is included in noise indicators 135 of memory 122 of circuitry 94) and may thus determine that one or more components of a signal that is delivered or otherwise captured or identified by delivery device 50 are defining non-fixation configuration 150 as a result of the frequency components defining the magnitude greater than the threshold.

In some examples, circuitry 94 may be configured to determine and indicate single momentary configuration arrangements of deployment bay 52 and IMD 16A relative to tissue of the target site. For example, processing circuitry 120 may cause signal generation circuitry 124 to create a voltage potential across first electrode 90 and second electrode 92 for a time period that is sufficient for processing circuitry 120 to determine and analyze an impedance of the electrical signal as delivered across path 132, in response to which processing circuitry 120 may cause signal generation circuitry 124 to cease the voltage potential (as well as causing indicating circuitry 128 to provide an indication of the configuration to user interface 104). For example, processing circuitry 120 may cause signal generation circuitry 124 to provide a signal for between 1 and 5 seconds, a duration which may provide indicative average values. In such an example, a clinician may provide an input (e.g., using user interface 104 and/or programmer 18 or the like) to circuitry 94, in response to which circuitry may provide a single configuration analysis (e.g., deployment bay 52 defining first fixation configuration, IMD 16A defining second fixation configuration, none of delivery device 50 in any fixation configuration). Put differently, in some examples circuitry 94 may be configured to provide "snapshots" of immediate and momentary spatial alignments of the delivery device 50 and tissue of the target site.

In other examples, circuitry 94 may be configured to determine and indicate changing configuration information over time. For example, processing circuitry 120 may cause signal generation circuitry 124 to create an ongoing and substantially static voltage potential across first electrode 90 and second electrode 92, such that impedance detection circuitry 126 identifies an ongoing impedance with which processing circuitry 120 provides an ongoing analysis of the ongoing impedance of the ongoing electrical signal as delivered across path 132. As a result of this, processing circuitry 120 may control indicating circuitry 128 to cause user interface 104 to provide changing fixation configurations over time in response to impedance updates from impedance detection circuitry 126. In such an example, a clinician may provide an initial input (e.g., using user interface 104 and/or external device 18 or the like) to circuitry 94 to start providing ongoing fixation configuration indications, in response to which circuitry 94 may continue providing indications until the clinician instructs circuitry 94 to stop providing fixation configuration indications. For example, a clinician may provide an initial input to start providing fixation indications, in response to which signal generation circuitry 124 may deliver an electrical signal to path 132 between first electrode 90 and second electrode 92, in response to which processing circuitry 120 may initially determine that an impedance detected by impedance detection circuitry 126 is below impedance threshold 134, in response to which indicating circuitry 128 may cause user interface 104 to indicate a failure to define first fixation configuration (e.g., by causing an LED to display a red light), in response to which a clinician may move deployment bay 52 against tissue of target site, in response to which processing circuitry 120 may determine that impedance of the electrical signal across path 132 as identified by impedance detection circuitry 126 has changed to be above impedance threshold 134, in response to which indicating circuitry 128 may cause user interface 104 to indicate a first fixation configuration (e.g., such a green light), in response to which a clinician may deploy IMD 16A, in response to which processing circuitry 120 may determine that impedance waveforms of a signal across path 132 do not include bimodal signatures 137, in response to which indicating circuitry 128 may cause user interface 104 to indicate a second fixation configuration (e.g., such as a blue light), in response to which the clinician may provide an input to circuitry 94 to cease delivering the electrical signal to path 132 between first electrode 90 and second electrode 92.

Power source 130 delivers operating power to various components of circuitry 94. In some examples, power source 130 may represent a hard-wired electrical supply of alternating or direct electrical current. In other examples, power source 130 may include a small rechargeable or non-rechargeable battery and a power generation circuitry to produce the operating power. Where power source 130 is rechargeable, recharging may be accomplished through proximal inductive interaction between an external charger and an inductive charging coil coupled to power source 130.

In some examples, as conceptually depicted, processing circuitry 120, memory 122, signal generation circuitry 124, impedance detection circuitry 126, indicating circuitry 128, and power source 130 may all be directly physically coupled to each other and to electrodes 90, 92 through a physical medium (e.g., wires or vias or traces or the like). Further, in some examples, each of processing circuitry 120, memory 122, signal generation circuitry 124, impedance detection circuitry 126, indicating circuitry 128, and power source 130 may be housed within a single enclosure, such as a hermetically sealed housing of IMD 16A or in hub 56 of delivery device 50 or the like. In other examples, different elements of circuitry 94 may be housed in two or more enclosures, and may communicate using a variety of physical (e.g., wired) connections and wireless communication protocols.

For example, IMD 16A may include some signal generation circuitry 124, impedance detection circuitry 126, power source 130 to power signal generation circuitry 124 and impedance detection circuitry 126, and some processing circuitry (e.g., processing circuitry that is similar but less powerful than processing circuitry 120) that is configured to cause signal generation circuitry 124 to create an electrical signal to path 132 between electrodes 90, 92 and cause impedance detection circuitry 126 to detect an impedance of the signal across path 132. In this example, this processing circuitry 120 may further be configured use telemetry circuitry (not depicted) to send the impedance data as detected by impedance detection circuitry 126 to another device that includes processing circuitry 120, memory 122, and indicating circuitry 128. For example, IMD 16A may send impedance data to another device that is external to IMD 16A (e.g., such as external device 18) that may include processing circuitry 120, memory 122, and indicating circuitry 128, in response to which the another device may analyze the impedance data and verify whether or not deployment bay 52 and/or IMD 16A defines first or second fixation configurations as described herein.

FIGS. 4A and 4B are conceptual diagrams illustrating views as taken along longitudinal axis 60 of delivery device 50 as not defining and then defining, respectively, a first fixation configuration relative to target site 140 in patient 14. FIGS. 4A and 4B are depicted without IMD 16A for purposes of clarity, as first fixation configuration is between deployment bay 52 and tissue of target site 140. As described herein, target site 140 may be in right atrium 20 of heart 12 of patient 14, though delivery device 50 may be used to delivery an implantable medical device to other areas of patient 14 in other examples. Target site 140 may include layer of tissue 142 to which IMD 16A is configured to pierce during deployment in order to secure IMD 16A to the target site 140. Put differently, in some examples IMD 16A is configured to mechanically attach itself to tissue layer 142 of target site 140. IMD 16A may be configured to secure itself to tissue layer 142 using fixation element 82 such as distal tines some other fixation means (e.g., helical coil) that are configured to distally extend from deployment bay 52 when IMD 16A is deployed (e.g., using deployment mechanism 66 of FIGS. 2A and 2B that distally pushes IMD 16A out of distal opening 78 of deployment bay 52). Further, in some examples, target site 140 may include muscle layer 144 that is beneath tissue 142 from the reference of delivery device 50, i.e., further away from delivery device 50 than tissue 142.

As depicted in FIG. 4A, a clinician has navigated delivery bay 52 of delivery device 50 to target site 140, such that IMD 16A (not depicted in FIG. 4A) as housed at least partially within deployment bay 52 is adjacent target 140. Deployment bay 52 may be navigated proximal to target site 140 as a result of a distal force 146 applied to delivery device 50. A clinician may apply distal force 146 by, e.g., manually applying a force to one or more proximal components of delivery device 50. For example, a clinician may apply distal force 146 to hub 56 (depicted in FIG. 2A), or otherwise apply distal force 146 using hub 56.

As depicted in FIG. 4A, deployment bay 52 may contact tissue 142 at target site 140 as a result of distal force 156 (e.g., as applied by clinician). Deployment bay 52 may contact tissue 142 at angle 148 relative to longitudinal axis 60 of delivery device 50. Put differently, FIG. 4A depicts distal surface 80 that defines distal opening 78 of deployment bay 52 defining angle 148 with a surface of target site 140 (e.g., rather than the two surfaces being flush or parallel with each other). As a result of approaching target site 140 at angle 148, deployment bay 52 may define path 132A (which may be substantially similar to path 132) between first electrode 90A and second electrode 92A. As depicted in FIG. 4A, path 132A initially extends substantially only through fluid (e.g., rather than tissue 142) of patient 14 as a result of deployment bay 52 contacting tissue 142 at angle 148. If delivery device 50 deploys IMD 16A when distal surface 80 that defines distal opening 78 of deployment bay 52 is at angle 148 to target site 140, tines or fixation elements 82 of IMD 16A may have difficulty fixating to target site 140 as intended. For example, tines or fixation elements 82 of IMD 16A that are close to a side of deployment bay 52 that is contacting tissue 142 may secure to muscle 144, while tines or fixation elements opposite side 162 may not successfully secure to any tissue 142 of target site 140.

A clinician may provide a prompt to circuitry 94 to send electric signal to path 132A between first electrode 90A and second electrode 92A. The depicted location of first electrode 90A and second electrode 92A in FIG. 4A is for purposes of illustration only, as both first electrode 90A and second electrode 92A may be at different locations and/or may be secured to or otherwise part of other components in other examples. For example, in some situations first electrode 90A may be a distal electrode on distal tip 96 of IMD 16A as described herein. For another example, in some cases first and/or second electrodes 90A, 92A may not extend fully around an inner or outer surface of deployment bay 52, respectively, but may only occupy a discrete circumferential portion of an inner or outer surface of deployment bay 52.

The clinician may provide the prompt to circuitry 94 in order to test if deployment bay 52 is defining the first fixation stage relative to tissue 142. The clinician may provide the prompt in response to detecting that deployment bay 52 has approached tissue 142 of target site 140. The clinician may detect that deployment bay 52 has approached tissue 142 of target site 140 by tracking one or more radiopaque elements (not depicted) secured to or adjacent deployment bay 52. In some examples, first electrode 90A and/or second electrode 92A may function as radiopaque elements. The clinician may provide the prompt to start testing using external device 18 or using user interface 104 on hub 56 or using some other input mechanism. In some examples, the clinician may provide a specific input to use first electrode 90A within deployment bay 52 and second electrode 92A outside of deployment bay 52 to test whether deployment bay 52 defines a first fixation configuration relative to tissue 142 of target site 140 (e.g., rather than testing whether or not IMD 16A defines a second fixation configuration relative to tissue 142 of target site 140).

Processing circuitry 120 may receive the input from the clinician and cause signal generation circuitry 124 to generate the signal along path 132A. Signal generation circuitry 124 may use conductors 102 that extend longitudinally through delivery device 50 to create a relatively static voltage potential across first and second electrodes 90A, 92A. It is to be understood that the depiction of conductors 102 within FIG. 4A (and also FIG. 4B) is for purposes of illustration only. Processing circuitry 120 may detect that impedance across path 132A as detected by impedance detection circuitry 126 is below impedance threshold 134 as a result of path 132A containing entirely fluid of patient 14. As such, processing circuitry 120 may detect that deployment bay 52 is defining non-fixation configuration 150A relative to tissue 142 of target site 140. Processing circuitry 120 may cause indicating circuitry 128 to provide an indication (e.g., using user interface 104) that deployment bay 52 is in non-fixation configuration 150A.

In response to the clinician noticing user interface 104 (e.g., as displayed on external device 18) indicating non-fixation configuration 150A, the clinician may navigate or otherwise manipulate or deflect deployment bay 52 relative to tissue 142 of target site 140. For example, as depicted in the conceptual view along longitudinal axis 60 of FIG. 4B, the clinician may control delivery device 50 (e.g., using one or more steering or movement or deflection mechanisms of hub 56) to cause deployment bay 52 to define first fixation configuration 152A relative to tissue 142 of target site 140. First fixation configuration 152A may include surface 80 that defines distal opening 78 of deployment bay 52 being substantially and/or entirely flush against tissue 142 of target site 140. Put differently, first fixation configuration 152A may include longitudinal axis 60 of delivery device 50 and therein deployment bay 52 being normal to (at a substantially right angle to) a surface defined by tissue 142 of target site 140.

As discussed herein, circuitry 94 may detect and verify when deployment bay 52 defines first fixation configuration 152A relative to tissue 142 of target site 140. For example, as discussed herein, processing circuitry 120 may cause signal generation circuitry 124 to generate an electrical signal across path 132A between first electrode 90A and second electrode 92A. As depicted in FIG. 4B, path 132A may include some tissue 142 when deployment bay 52 defines first fixation configuration 152A relative to tissue 142 of target site 140. Processing circuitry 120 may detect that an impedance detected by impedance detection circuitry 126 has raised above impedance threshold 134 (e.g., as a result of path 132A including tissue 142 of patient 14. In response to processing circuitry 120 detecting that the impedance of path 132A has raised above impedance threshold 134, processing circuitry 120 may cause indicating circuitry 128 to provide an indication using user interface 104 that deployment bay 52 is defining first fixation configuration 152A.

In some examples, circuitry 94 may generate an ongoing electrical signal on path 132A and may therein provide an ongoing indication as to whether or not deployment bay 52 is defining first fixation configuration 152A. For example, in response to processing circuitry 120 determining that impedance of path 132A was below impedance threshold 134 in FIG. 4A as a result of deployment bay 52 defining non-fixation configuration 150A, processing circuitry 120 may cause indicating circuitry 128 to provide an ongoing indication of non-fixation configuration 150A. Processing circuitry 120 may cause indicating circuitry 128 to provide an ongoing indication until processing circuitry 120 receives input from a clinician to cease providing an indication. If processing circuitry 120 detects that impedance of path 132A as detected by impedance detection circuitry 126 rises above impedance threshold 134 (e.g., as in FIG. 4B), processing circuitry 120 may cause indicating circuitry 128 to provide a different ongoing indication indicating first fixation configuration 152A. In this way a clinician may receive an ongoing indication as to whether deployment bay 52 is stably defining first fixation configuration 152A (e.g., when deployment bay 52 defines first fixation configuration 152A for two second straight as indicated on user interface 104), and therein the clinician may deploy IMD 16A in response to deployment bay 52 stably defining first fixation configuration 152A. By configuring circuitry 94 to determine and indicate an ongoing and real-time (e.g., substantially instantaneous) fixation status of deployment bay 52, circuitry 94 may improve an ability of delivery device 50 to deploy IMD 16A in an efficacious fixation alignment as discussed herein.

In some examples, first fixation configuration 152A may include surface 80 that defines distal opening 78 contacting tissue 142, such that delivery device 50 is efficaciously arranged to deploy IMD 16A as soon as surface 80 contacts tissue 142. Put differently, in such examples, as soon as substantially all of distal surface 80 contacts tissue 142, deployment bay 52 may define first fixation configuration 152A. In other examples, first fixation configuration 152A may include surface 80 that defines distal opening 78 pressing against tissue 142 of target site, such that delivery device 50 is efficaciously arranged to deploy IMD 16A as soon as surface 80 presses into tissue 142. Distal surface 80 of deployment bay 52 may press against tissue 142 as a result of distal force 146. Distal surface 80 may press into tissue 142 with enough force to momentarily deflect and/or deform tissue 142 but not penetrate or otherwise damage tissue 142. Whether first fixation configuration 152A includes contacting or pressing into tissue 142 may relate to the manner in which fixation elements 82 of IMD 16A are deployed from deployment bay 52 to become secured to tissue 142 of target site 140. For example, in some situations fixation elements 82 may be configured such that fixation elements 82 may be relatively more likely to secure IMD 16A according to a preferred manner when surface 80 initially contacts tissue 142. Alternatively, in other situations fixation elements 82 may be configured such that fixation elements 82 are relatively more likely to secured IMD 16A in a preferred manner when surface 80 presses against tissue 142. In either situation, circuitry 94 may be configured to verify when distal surface 80 defines such fixation configuration.

For example, an impedance of an electrical signal across path 132A may be relatively lower as a result of distal surface 80 being flush with (rather than being pressed against) tissue 142 of target site 140. The impedance may be relatively lower as a result of slight deviations (e.g., non-flat features) in the surface of tissue 142 that define small channels between surface 80 and tissue 142 through which a small amount of fluid may pass (e.g., because surface 80 is not pressing against tissue 142 to deform tissue 142 and therein effectively eliminate the presence of such channels). As such, where fixation elements 82 and IMD 16A are configured such that IMD 16A is more likely to be efficaciously secured when distal surface 80 contacts (rather than presses against) tissue 142, impedance threshold 134 as stored within memory 122 and utilized by processing circuitry 120 may be relatively lower. Similarly, where fixation elements 82 and IMD 16A are configured such that IMD 16A is more likely to be efficaciously secured when distal surface 80 presses against (rather than merely is flush with) tissue 142, impedance threshold 134 as stored within memory 122 and utilized processing circuitry 120 may be relatively higher.

Further, as discussed herein, circuitry 94 may be configured to detect and verify when and/or whether IMD 16A defines a second fixation configuration relative to tissue 142 of target site 140 upon IMD 16A being deployed. For example, FIGS. 5A-5D depict conceptual illustrations of IMD 16A being deployed from deployment bay 52 at target site 140. Though FIGS. 5A-5D are depicted with outer wall 76 of deployment bay 52 being transparent to depict IMD 16A for purposes of illustration, it is to be understood that in some examples outer wall 76 of deployment bay 52 may not be transparent. Circuitry 94 may generate an electrical signal to be sent through tissue 142 and fluid of patient 14 along path 132B (which may be substantially similar to path 132 and path 132A with the exception of any differences described herein) between first electrode 90B and second electrode 92B. As depicted, first electrode 90B may be secured to distal tip 96 of IMD 16A, while second electrode 92B includes a band that runs around at least a part of an outer perimeter of IMD 16A. First electrode 90B may be substantially similar to first electrode 90 and first electrode 90A, and second electrode 92B may be substantially similar to second electrode 92 and second electrode 92B FIGS. 5A-5D depict fixation elements 82A, 82B (collectively, "fixation elements 82") deploy from deployment bay 52 to secure IMD 16A to tissue 142. As depicted in FIGS. 5A-5D, fixation elements 82 may include tines. Fixation elements 82 include two tines that are mirrored across electrode 90B in FIGS. 5A-5D for purposes of clarity, but more or less fixation elements 82 may be included in other examples. For example, IMD 16A may include three, four, or more tine fixation elements 82 that are arranged around first electrode 90B in a circular arrangement on distal tip 96 of IMD 16A, or IMD 16A may include a single helical coil that wraps around electrode 90B as the helical coil extends distally from distal tip 96 of IMD 16A. Fixation elements 82 that include tines may comprise distal ends that are configured to extend into tissue 142 and then curl back proximally out of tissue 142 toward IMD 16A. However, in other examples fixation elements 82 may include tines that operate differently, or fixation elements 82 may include distal helical coils or the like. Fixation elements 82 may be configured to secure IMD 16A to tissue 142 such that first electrode 90B contacts tissue 142. Further, fixation elements 82 may be configured to provide a forward pressure onto electrode 90B such that electrode 90B presses into tissue 142 to assure proper electrode-tissue contact.

Figure 5A:
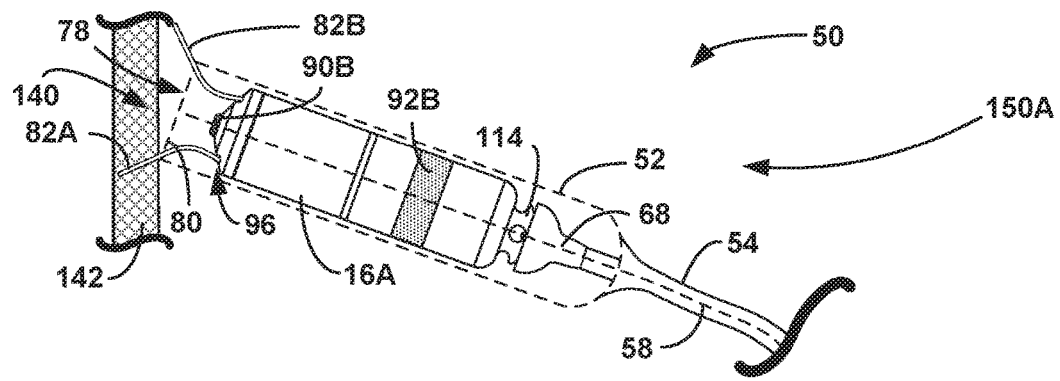
FIGS. 5A and 5B are conceptual diagrams illustrating views of the delivery device and IMD of FIG. 2A approaching a target site and defining a second non-fixation configuration relative to the target site, respectively.
Figure 5B:
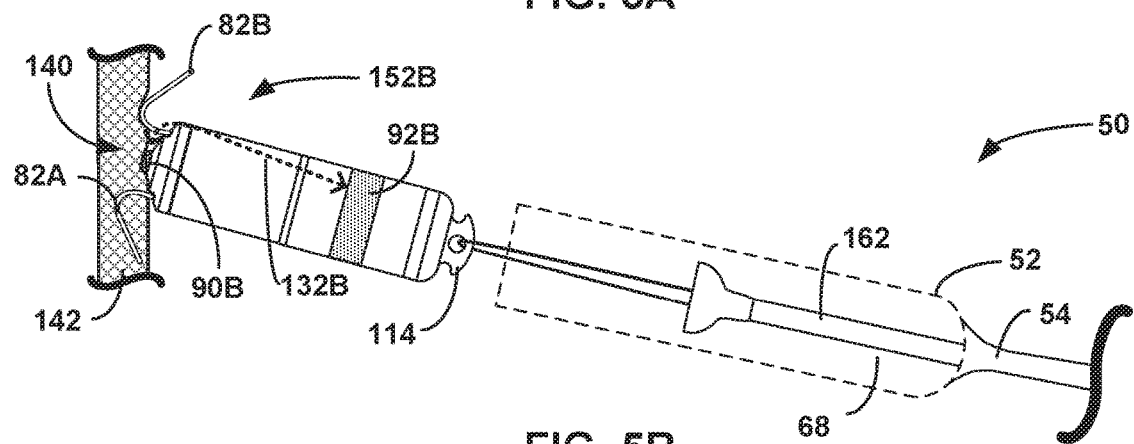

As depicted in FIG. 5A, deployment bay 52 may contact tissue 140 at an angle (e.g., an angle similar to angle 148 of FIG. 4A) such that surface 80 of deployment bay 52 is not flush with tissue 142. As a result of surface 80 not being flush with tissue 142, deployment bay 52 may define non-fixation configuration 150A relative to tissue 140. In some examples, deployment bay 52 may define non-fixation configuration 150A as a result of a clinician not testing if deployment bay 52 defines first fixation configuration 152A (e.g., as a result of delivery device 50 not being configured to test if deployment bay 52 defines first fixation configuration 152A). Alternatively, deployment bay 52 may have previously defined first fixation configuration 152A as determined by circuitry 94 and indicated to a clinician using user interface 104, after which deployment bay 52 and/or tissue 142 may have moved relative to each other as IMD 16A was deployed.

As depicted in FIG. 5A, fixation elements 82 may extend distally out of distal opening 78. Fixation elements 82 may extend distally out of distal opening 78 as a result of pushing element 68 pushing IMD 16A distally within deployment bay 52. Where deployment bay 52 defines non-fixation configuration 150A, some of fixation elements 82 may not fully engage tissue 142 as fixation elements 82 extend distally from deployment bay 52. For example, as depicted, fixation element 82A may extend into tissue 142 while fixation element 82B does not contact/engage tissue 142. In some cases, as discussed above, fixation element 82A close to tissue 142 when IMD 16A is deployed may pierce muscle 144 (e.g., as depicted in FIGS. 4A and 4B) of target site 140, though such piercing is not depicted in FIGS. 5A and 5B for purposes of clarity. As depicted in FIG. 5B, fixation elements 82 may pull electrode 90B in contact with tissue 142. Upon some or all fixation elements 82 engaging tissue 142, a clinician may partially proximally retract deployment bay 52 and delivery device 50 to test a fixation of IMD 16A.

For example, as discussed herein, a clinician may attempt a tug test, where a clinician tugs on a proximal end of IMD 16A to verify that IMD 16A is securely attached to tissue 142. A clinician may use a longitudinal member that engages a proximal end of IMD 16A to execute a tug test. For example, IMD 16A may include proximal catch 114 that extends proximally from IMD 16A and may be engaged with tether 162 of delivery device 50. Tether 162 may be configured to engage an aperture of proximal catch 114 as depicted in FIGS. 5A-5D. Tether 162 may be configured to move within delivery device 50. For example, tether 162 may be configured to be slideable within a deployment mechanism (e.g., such as deployment mechanism 66 of FIGS. 2A and 2B) of delivery device 50 and operable from hub 56 of delivery device 50. A clinician may tug on IMD 16A by tugging on tether 162 that is engaged with catch 114.

However, tissue 142 of target site 140 may be too thin for a clinician to visually identify if fixation elements 82 are secured to tissue 142. For example, where target site 140 is in right atrium 20, tissue 142 may be between 2 to 3 millimeters (mm) thick, such that where fixation elements 82 are attempting to avoid muscle 144 behind tissue 142 fixation elements may only extend 1 or 2 mm into tissue 142. As such, depending upon an angle of IMD 16A and tissue 142 of target site 140, it may be difficult or impossible to see if fixation elements 82 have engaged any of tissue 142 upon deployment.

Therefore, as discussed herein, a clinician may use circuitry 94 to verify if IMD 16A defines a second fixation configuration relative to tissue 142. Circuitry 94 may generate an electrical signal to path 132B (which may be substantially similar to path 132 and path 132A with the exception of any differences discussed herein) between first electrode 90B and second electrode 92B. In some examples, circuitry of IMD 16A (e.g., circuitry 28 of FIG. 1A) may comprise some or all of circuitry 94.

Circuitry 94 may include processing circuitry 120 that causes signal generation circuitry 124 to generate the electrical signal. As discussed herein, the electrical signal can be transmitted by generating a voltage potential across first electrode 90B and second electrode 92B. Processing circuitry 120 may analyze an impedance of the electrical signal on path 132B between first and second electrodes 90B, 92B that is detected by impedance detection circuitry 126. For example, where tissue 142 is tissue 142 of heart 12, impedance as detected by impedance detection circuitry 126 may include and/or reflect one or more intrinsic waveforms of heart 12. Processing circuitry 120 may detect whether these one or more impedance waveforms of electrical signal as impacted by heart 12 are stable, or whether impedance waveforms have more than a threshold amount of noise (e.g., as determined by the presence of bimodal signatures 137 as stored in memory 122 of circuitry 94 from FIG. 3). The waveforms as reflected in impedance may be stable as a result of how well engaged first electrode 90A is with tissue 142 of heart 12 (as a result of fixation elements 82 engaging tissue 142). For example, electrode 90A may be engaged with tissue 142 of heart 12 sufficiently when a threshold amount of fixation elements 82 engage tissue 142 (e.g., at least two circumferentially adjacent fixation elements 82 of four fixation elements 82 that surround first electrode 90A in a circular arrangement, or at least 75% of helical screws of a single distal screw that extends from a respective IMD).

In some examples, processing circuitry 120 may detect that the impedance waveform of the electrical signal includes bimodal signatures 137 and therein indicate that IMD 16A defines non-fixation configuration 150B relative to tissue 142. In some examples, processing circuitry 120 may detect that the impedance waveform includes bimodal signatures 137 while a clinician executes a tug test. For example, a tug test may exacerbate or make pronounced any errors or shortcomings of the fixation of IMD 16A to tissue 142. By testing path 132B between electrodes 90B, 92B while a clinician is tugging on proximal catch 114 using tether 162, a clinician may increase an ability of circuitry 94 to determine whether or not IMD 16A is deployed such that IMD 16A defines a second fixation configuration relative to tissue 142.

In response to processing circuitry 120 detecting that an impedance waveform includes bimodal signatures 137, processing circuitry 120 may cause indicating circuitry 128 to provide indication on user interface 104 of second non-fixation configuration 150B. A clinician may see this indication of non-fixation configuration 150B of IMD 16A relative to tissue 142 and therein decide to retract 16A fully back into deployment bay 52 to redeploy IMD 16A. Delivery device 50 may include any of a plurality of retraction mechanism to retract IMD 16A into deployment bay 52 once fixation elements 82 are deployed from deployment bay 52 are partially affixed to tissue 142. For example, a clinician may pull on tether 162 to remotely pull IMD 16A back into deployment bay 52. Pulling IMD 16A back into deployment bay 52 may release IMD 16A from patient tissue 142 and returns IMD 16A to the position shown in FIG. 2A. For example, pulling IMD 16A back into deployment bay 52 may return fixation elements 82 back from the deployed position (where the distal ends of fixation elements 82 extend proximally back towards IMD 16A) into a deployable position (where the distal ends of fixation elements 82 extend distally from IMD 16A). From this position, a clinician may reposition IMD 16A as desired and redeploy IMD 16A.

Figure 5C:
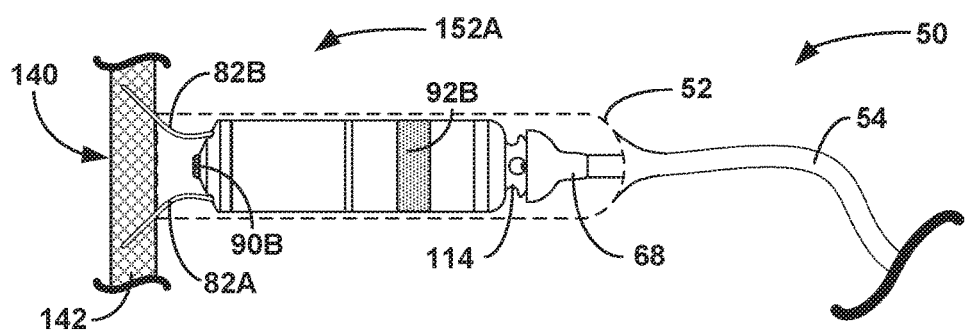
FIGS. 5C and 5D are conceptual diagrams illustrating views of the delivery device and IMD of FIG. 2A approaching a target site and defining a second fixation configuration relative to the target site, respectively.
Figure 5D:
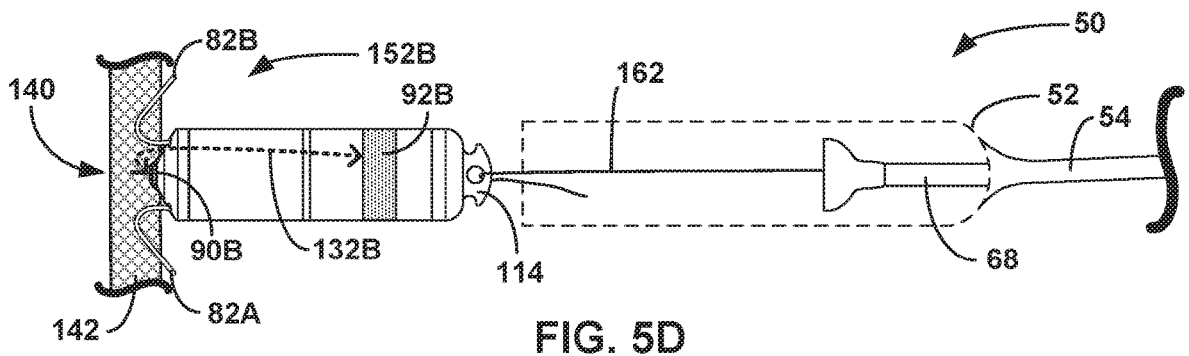

For example, as depicted in FIG. 5C, deployment bay 52 may be repositioned relative to tissue 142. Deployment bay 52 may be positioned into first fixation configuration 152A. For example, a clinician may use electrodes and circuitry 94 of delivery device 50 to verify that distal surface 80 the defines distal opening 78 of deployment bay 52 is flush with tissue 142. Circuitry 94 may verify that the impedance of the electrical signal provided across a path (e.g., path 132A) is over impedance threshold 134 before processing circuitry 120 causes indicating circuitry 128 to provide indication of first fixation configuration 152A to user interface 104.

Once deployment bay 52 defines first fixation configuration 152A relative to tissue 142, IMD 16A may be pushed distally (e.g., using pushing element 68) such that fixation elements 82 extend distally out of deployment bay 52 and engage tissue 142 as depicted in FIG. 5C. Once fixation elements 82 extend distally out of deployment bay 52 to engage tissue 142, fixation elements 82 may be configured to push IMD 16A distally to secure IMD to tissue 142. In other examples, fixation elements 82 may have to be manually secured to tissue 142.

In response to fixation elements 82 deploying IMD 16A from deployment bay 52, delivery device 50 may verify whether or not IMD 16A is in a second fixation configuration relative to tissue 142. For example, as described above, circuitry 94 may generate an electrical signal across path 132B and identify if impedance waveforms are stable (e.g., stable through a tug test) or if impedance waveforms include bimodal signatures 137. Where first electrode 90A is pressed into tissue 142 sufficiently as depicted in FIG. 5D, impedance waveforms may be relatively stable and may have little or no noise indicators 135, such that internal processing 94 may identify that IMD 16A defines second fixation configuration 152B relative to tissue 142. In some examples, as described herein, a clinician may perform one or more tug tests while circuitry 94 is providing the electrical signal to electrodes 90B, 92B as well as when circuitry 94 is verifying that IMD 16A defines second fixation configuration 152B. For example, a clinician may initially wait for a few seconds (e.g., approximately 5 seconds) before starting a tug test, and then a clinician may maintain the pressure on tether 162 for a few second (e.g., approximately 5 seconds) to improve an ability of circuitry 94 to gather an adequate baseline for comparison. In response to IMD 16A defining second fixation configuration 152, processing circuitry 120 of circuitry 94 may provide an indication of a successful second fixation configuration 152B using user interface 104 to a clinician.

As shown in FIG. 5D, once IMD 16A is secured to patient tissue 142 in second fixation configuration 152B, the clinician may release IMD 16A from tether 162. For example, the clinician may sever tether 162 at a port in hub 56 of delivery device 50 and remove tether 162 from delivery device 50 by pulling on one of the severed ends of tether 162. As shown in FIG. 5D, once IMD 16A is released from tether 162, the clinician may remove delivery device 50, leaving IMD 16A secured to patient tissue 142.

Figure 6:
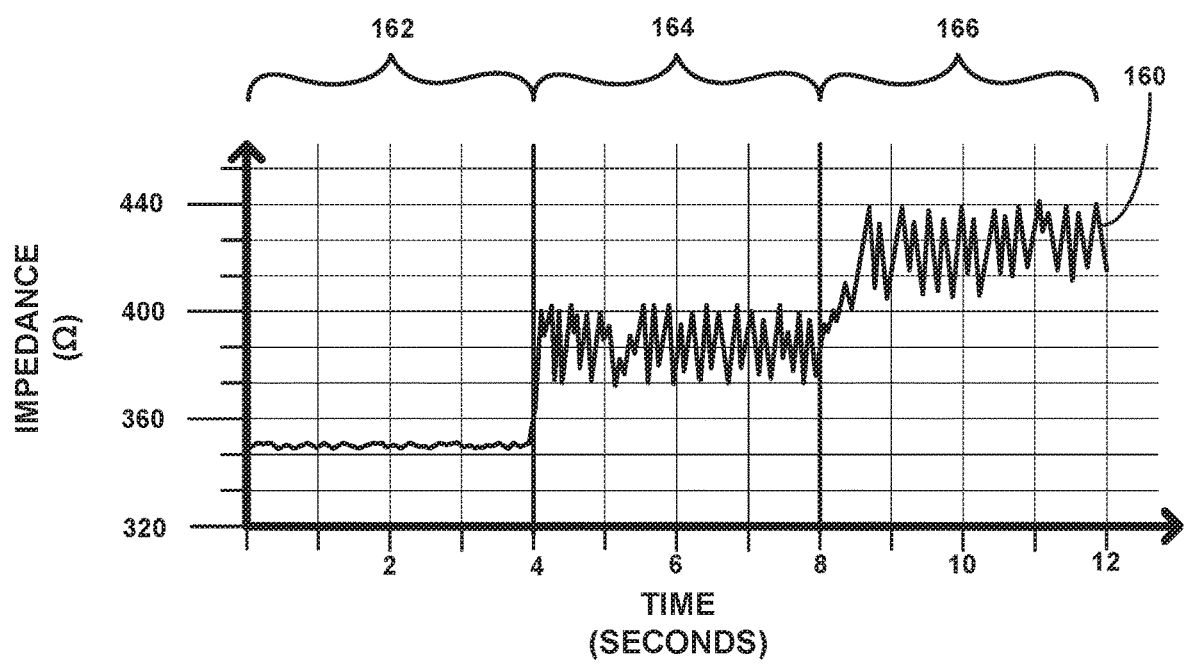
FIG. 6 is a chart of example impedance data that indicates a first fixation configuration.

FIG. 6 is a chart of example impedance data 114 as may be identified by processing circuitry 120 as indicating first fixation configuration 152A. It is to be understood that impedance data 114 provided in FIG. 6 is provided for purposes of illustration only, as other systems may alter impedance values and similar systems may generate different impedance values depending upon medical conditions of patient 14. As depicted, impedance data 114 may cover testing over multiple stages. For example, first stage 162 includes impedance data 114 of an electrical signal across path 132 that included substantially only fluid of patient 14 (e.g., such as FIG. 4A). Further, second stage 164 includes impedance data 114 of an electrical signal across path 132 when distal opening 80 of deployment bay 52 is flushly contacting but not pressing against tissue 142. Lastly, third stage 166 includes impedance data 114 of an electrical signal across path 132 when distal opening of deployment bay 52 is both flush with and pressing against tissue 142 of target site 140. As will be understood by one of ordinary skill in the art, oscillations in the signal as indicated in FIG. 6 (as well as FIG. 7-FIG. 9B) represent movement and activity of heart 12 during the cardiac cycle as picked up by electrodes 90, 92.

As depicted, impedance data 114 may increase in magnitude as deployment bay 52 contacts and then presses up against tissue 142 of target site 140. For example, impedance data 114 may initially hold relatively steady around 350Ω during first stage 162, after which impedance data 114 may fluctuate between around 400Ω and 370Ω during second stage 164, after which impedance data 114 may fluctuate between approximately 405Ω and 440Ω in third stage 166. In this example, circuitry 94 may use impedance threshold 134 of around 370Ω where first fixation configuration 152A includes merely contacting tissue 142 of target site 140 flush, or circuitry 94 may use impedance threshold 134 of around 400Ω where first fixation configuration 152A includes pressing into tissue 142. Alternatively, circuitry 94 may include impedance threshold 134 of impedance data 114 increasing in value between 100% and 150% above impedance data 114 of first stage 162. Other examples are also possible.

Figure 7:
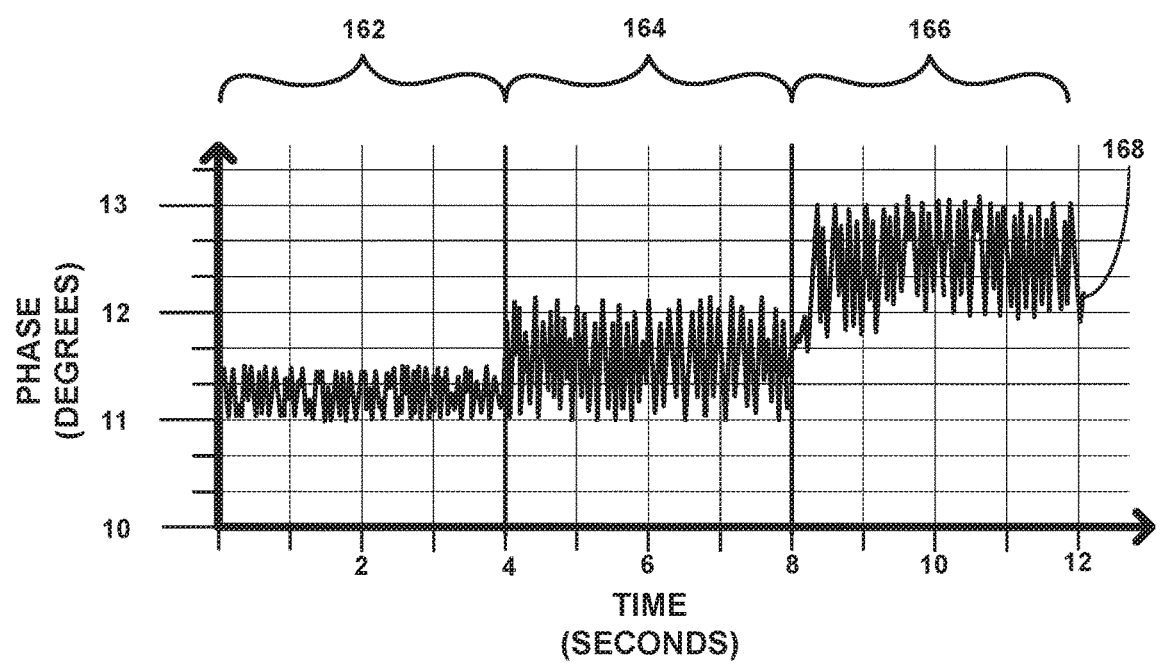
FIG. 7 is a chart of example phase data that indicates a first fixation configuration.

FIG. 7 is a chart of example phase data 168 as may be identified by impedance detection circuitry 126 and as determined by processing circuitry 120 to indicate first fixation configuration 152A. For example, as discussed herein, phase data 168 may be identified by monitoring the angle that the voltage leads or lags the current. It is to be understood that phase data 168 provided in FIG. 7 is provided for purposes of illustration only, as other systems may capture slightly different phase values and similar systems may capture different phase values depending upon medical conditions of patient 14. As depicted, phase data 168 may cover testing over multiple stages, similar to the chart of FIG. 6 as discussed above (e.g., where first stage 162 includes phase data 168 when path 132 includes substantially only fluid, second stage 164 includes phase data 168 when distal opening 80 is flush against tissue 142, and third stage 166 includes phase data 168 when distal opening of deployment bay 52 is pressing against tissue 142).

As depicted, phase data 168 may increase in magnitude as deployment bay 52 contacts and then presses up against tissue 142 of target site 140. For example, phase data 168 may initially fluctuate between 11° and 11.5° during first stage 162, after which phase data 168 may increase in range and fluctuate between around 11° and 12° during second stage 164, after which phase data 168 may fluctuate between approximately 12° and 13° in third stage 166. In this example, circuitry 94 may use phase threshold 133 of around 11.6° where first fixation configuration 152A includes merely contacting tissue 142 of target site 140 flush, or circuitry 94 may use phase threshold 133 of around 12.5° where first fixation configuration 152A includes pressing into tissue 142. Alternatively, circuitry 94 may include phase threshold 133 of a percentage increase (e.g., an increase of an average value of phase data 168 of first stage 162 of between 5% and 20%). Other examples are also possible.

FIG. 8A is a chart of example impedance data 170A as may be identified by impedance detection circuitry 126 and determined by processing circuitry 120 to indicate second non-fixation configuration 150B. It is to be understood that impedance data 170A provided in FIG. 8A is provided for purposes of illustration only, as other systems may alter impedance values and similar systems may generate different impedance values depending upon medical conditions of patient 14. As depicted, impedance data 170A may cover testing over multiple stages. For example, first stage 172A includes impedance data 170A of an electrical signal across path 132 before a tug test (e.g., using tether 162) while second stage 174A includes impedance data 170A of an electrical signal across path 132 during a tug test (e.g., using tether 162).

As depicted, impedance data 170A of IMD 16A that defines non-fixation configuration 150B may generally curve up and down between primary peaks 176A and primary valleys 178A. During first stage 172A, impedance data 170A may define relatively noisy slopes between primary peaks 176A and primary valleys 178A. For example, impedance data 170A defines slopes with ledges or steps, slopes that change a direction of a curve, slopes that are substantially horizontal, or the like between primary peaks 176A and primary valleys 178A. Processing circuitry 120 may be configured to detect these relatively complex slopes as exceeding slope threshold 136 stored in memory 122. As such, processing circuitry 120 may be configured to detect that first stage 172A of impedance data 170A indicates second non-fixation configuration 150B.

Additionally, or alternatively, processing circuitry 120 may analyze second stage 174A. Second stage data 174A may indicate second non-fixation configuration 150B with more clarity and repeatability than first stage data 172A in some examples (e.g., due to the tug test highlighting potential deficiencies in the manner in which IMD 16A is secured to tissue 142), improving an ability of processing circuitry 120 detecting second non-fixation configuration 150B. For example, processing circuitry 120 may detect bimodal signatures 180A incorporated into impedance data 170A during second stage 174A of tug test. Bimodal signatures 180A, as depicted and used herein, include more pronounced deviations in slopes between peaks 176A and valleys 178A than impedance data 170A of first stage 172A. For example, each of bimodal signatures 180A may define secondary peak 182 and secondary valley 184 in between defining primary peak 176A and primary valley 178A. For example, as depicted, during second stage 174A impedance data 170A defines secondary peaks 182 around 225Ω and secondary valleys 184 around 215Ω in addition to defining primary peaks 176A around 240Ω and primary valleys 178A around 220Ω Processing circuitry 120 may be configured to detect these secondary peaks 182 and valleys 184 as bimodal signatures 180A. As thusly detected, processing circuitry 120 may be configured to detect that impedance data 170A indicates second non-fixation configuration 150B.

FIG. 8B is a chart of example impedance data 170B as may be identified by impedance detection circuitry 126 and determined by processing circuitry 120 to indicate second fixation configuration 152B. It is to be understood that impedance data 170B provided in FIG. 8B is provided for purposes of illustration only, as other systems may alter impedance values and similar systems may generate different impedance values depending upon medical conditions of patient 14. As depicted, impedance data 170B may cover testing over multiple stages. For example, first stage 172B includes impedance data 170B of an electrical signal across path 132 before a tug test (e.g., using tether 162) while second stage 174B includes impedance data 170B of an electrical signal across path 132 during a tug test (e.g., using tether 162).

As depicted, impedance data 170B of IMD 16A that defines second fixation configuration 152B may generally curve up and down between primary peaks 176B and primary valleys 178B. However, as compared to impedance data 170A as detected by impedance detection circuitry 126 when IMD 16A defined second non-fixation configuration 150B, slopes between primary peaks 176B and primary valleys 178B are relatively smooth. For example, impedance data 170B defines slopes that substantially avoid defining ledges or steps, changes of direction, substantially horizontal sections, or the like between primary peaks 176B and primary valleys 178B. Processing circuitry 120 may be configured to detect these relatively smooth slopes as within or otherwise satisfying slope threshold 136 stored in memory 122. As such, processing circuitry 120 may be configured to detect that first stage 172B of impedance data 170B indicates second fixation configuration 152B.

Additionally, or alternatively, processing circuitry 120 may analyze second stage 174B. Impedance data of a second stage that is gathered during a tug test may indicate a possible second non-fixation configuration 150B with more clarity and repeatability than impedance data gathered when no tug test is being executed. Thus, processing circuitry 120 may categorize impedance data 170B as indicating second fixation configuration 152B with a higher degree of confidence (e.g., a higher confidence score) when processing circuitry 120 analyzes impedance data 170B of second stage 174B. For example, processing circuitry 120 may analyze impedance data 170B of second stage 174B and identify that slopes between primary peaks 176B and primary valleys 178B are substantially smooth. In some examples, processing circuitry 120 may be configured to disregard (e.g., not consider) transition data 182 at an initial period of second stage 174B where impedance data 170B later defines slopes within slope threshold 136. As a result of slopes of impedance data 170B being within slope threshold 136 during first stage 172A and second stage 172B, processing circuitry 120 may identify impedance data 170B as indicating second fixation configuration 152B.

Figure 9A:
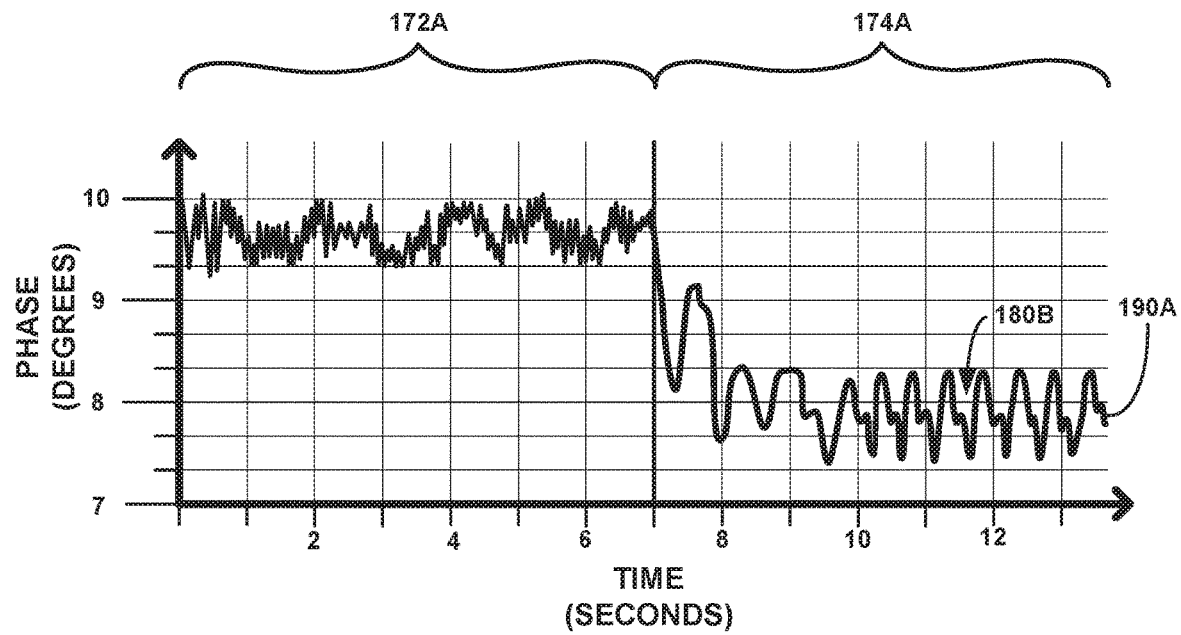
FIG. 9A is a chart of example phase data that indicates a second non-fixation configuration.
Figure 9B:
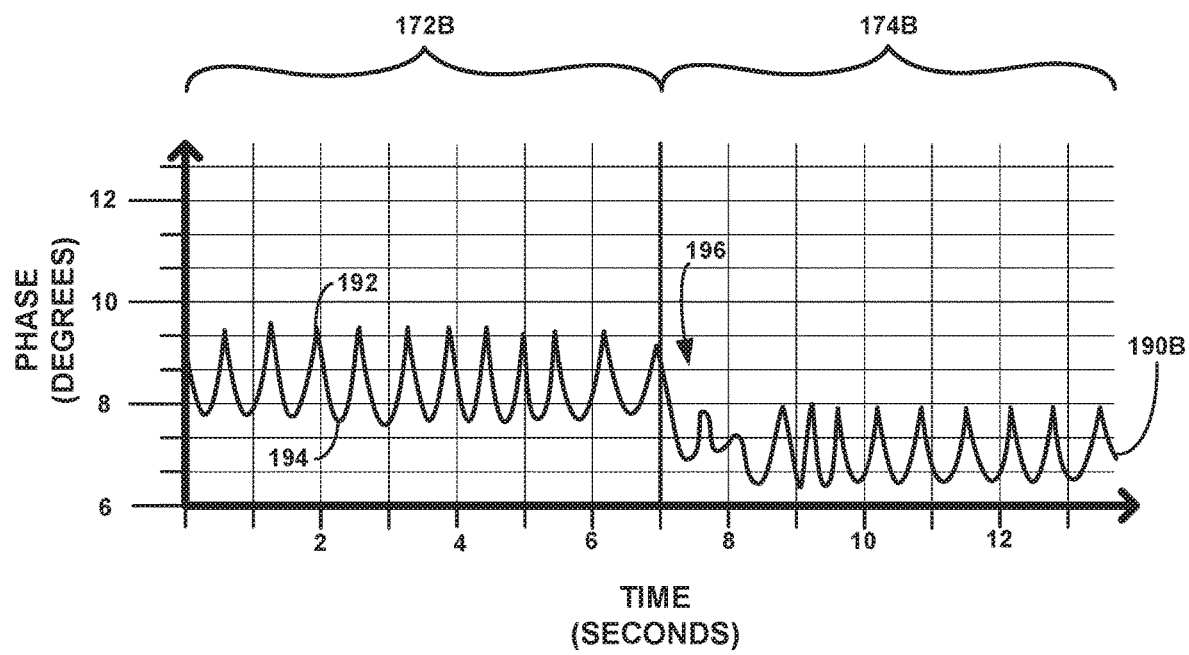
FIG. 9B is a chart of example phase data that indicates a second fixation configuration.

Additionally, or alternatively, processing circuitry 120 may analyze phase of the sets of impedance data 170A, 170B to determine whether or not the sets of impedance data 170A, 170B indicate second non-fixation configuration 150B or second fixation configuration 152B. FIGS. 9A and 9B are charts of example sets of phase data 190A, 190B as may be identified by processing circuitry 120 as indicating second non-fixation configuration 150B, and second fixation configuration 152B, respectively. For example, as discussed herein, each set of phase data 190A, 190B may be identified by identify an amount of lag between voltage and current from respective sets of impedance data 170A, 170B of FIGS. 8A and 8B. It is to be understood that phase data 190A illustrated in FIG. 9A and phase data 190B illustrated in FIG. 9B are both provided for purposes of illustration only, as other systems may capture slightly different phase values and similar systems may capture different phase values depending upon medical conditions of patient 14. As depicted, both phase data 190A and phase data 190B may cover testing over multiple stages, similar to the charts of FIGS. 8A and 8B as discussed above (e.g., where phase data of first stages 172A and 172B is gathered prior to a tug test and phase data of second stages 174A and 174B is gathered during a tug test).

As depicted, phase data 190A during first stage 172A may fluctuate dramatically between a general high value (e.g., approximately 10°) and a general low value (e.g., approximately 9.3°). Outside of these approximate upper and lower thresholds, phase data 190A may substantially avoid defining a repeating pattern. Put differently, phase data 190A may avoid defining a relatively consistent max value (e.g., a phase value that is the same as other peak values within first stage 172A, ±0.1°) or a relatively consistent minimum value (e.g., a phase value that is the same as other valley values within first stage 172A, ±0.1°) in first stage 17A. As a result of phase data 190A defining a slope that fails to define relatively consistent maximum and minimum values, processing circuitry 120 may determine that phase data 190A is outside of phase threshold 138. Thus, processing circuitry 120 may determine that phase data 190A indicates that IMD 16A defines non-fixation configuration 150B.

Additionally, or alternatively, processing circuitry 120 may analyze impedance data 190A of second stage 174A. Second stage data 174A may indicate second non-fixation configuration 150B with more clarity and repeatability than first stage data 172A in some examples (e.g., due to the tug test highlighting potential deficiencies in the manner in which IMD 16A is secured to tissue 142), improving an ability of processing circuitry 120 detecting second non-fixation configuration 150B. For example, processing circuitry 120 may detect bimodal signatures 180B incorporated into phase data 190A during second stage 174A of tug test. Bimodal signatures 180B may be substantially similar to bimodal signatures 180A of impedance data 170A. For example, each of bimodal signatures 180B may define a secondary peak and a secondary valley in between defining a primary peak and a primary valley. Processing circuitry 120 may be configured to detect these secondary peaks and valleys as bimodal signatures 180B. As thusly detected, processing circuitry 120 may be configured to detect that phase data 170A indicates second non-fixation configuration 150B.

As discussed herein, processing circuitry 120 may also analyze phase data and determine that phase data indicates that IMD 16A defines second fixation configuration 152B. For example, as depicted in FIG. 9B, phase data 190B of IMD 16A that defines second fixation configuration 152B may generally curve up and down between primary peaks 192 and primary valleys 194. As depicted, phase values of primary peaks 192 and primary valleys 194 may both be substantially consistent (e.g., ±0.1°). Further, slopes between primary peaks 192 and primary valleys 194 are relatively smooth (e.g., such that phase data 170B defines slopes that substantially avoid defining ledges, steps, changes of direction, substantially horizontal sections, or the like between primary peaks 192 and primary valleys 194). Processing circuitry 120 may be configured to detect that these substantially consistent maximum and minimum values (and or these relatively smooth slopes) as being within or otherwise satisfying phase threshold 138 stored in memory 122. As such, processing circuitry 120 may be configured to detect that first stage 172B of phase data 190B indicates second fixation configuration 152B.

Additionally, or alternatively, processing circuitry 120 may analyze phase data 190B of second stage 174B. Phase data of a second stage that is gathered during a tug test may indicate a possible second non-fixation configuration 150B with more repeatability than phase data gathered when no tug test is being executed. Thus, processing circuitry 120 may categorize phase data 190B as indicating second fixation configuration 152B with a higher degree of confidence (e.g., a higher confidence score) when processing circuitry 120 analyzes phase data 190B of second stage 174B. For example, processing circuitry 120 may analyze phase data 190B of second stage 174B and identify that slopes between primary peaks 192 and primary valleys 194 are substantially smooth, such that phase data 190B of second stage 174B does not define bimodal signatures 180B. In some examples, processing circuitry 120 may be configured to disregard (e.g., not consider) transition data 196 of phase data 190B at an initial period of second stage 174B where phase data 190B later defines slopes within phase threshold 138 without bimodal signatures 180B. As a result of slopes of phase data 190B being within phase threshold 138 during first stage 172A and second stage 172B without defining bimodal signatures 180B, processing circuitry 120 may identify phase data 190B as indicating second fixation configuration 152B.

Figure 10A:
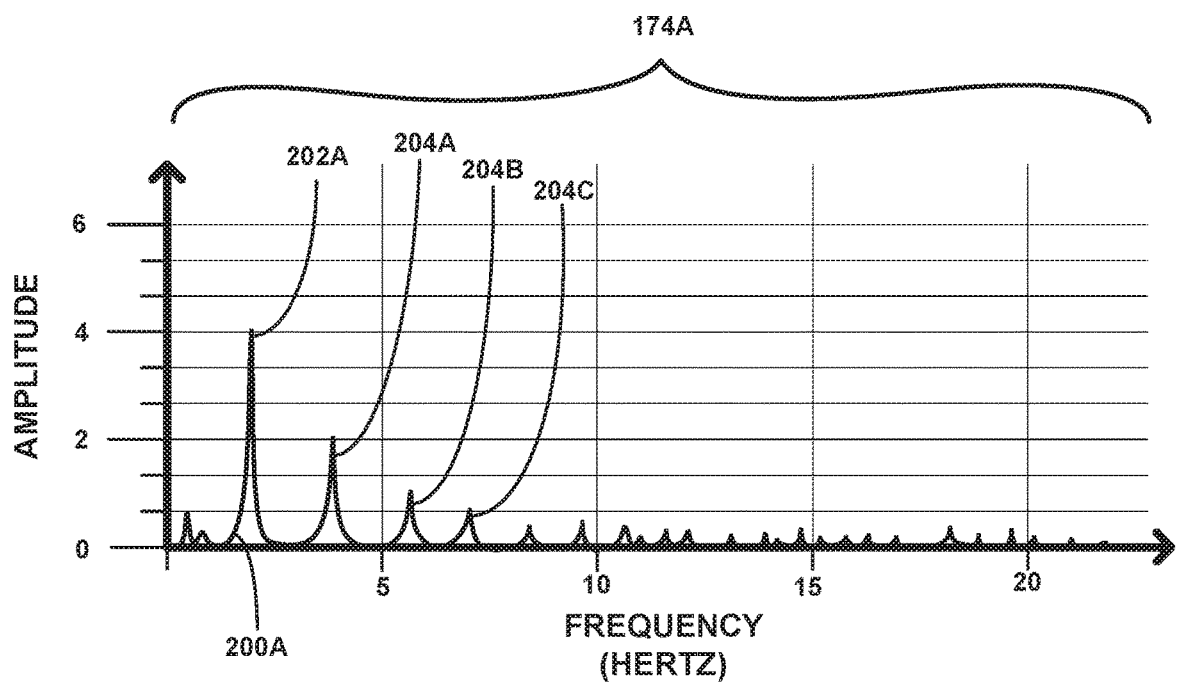
FIG. 10A is a chart of example FFT data that indicates a second non-fixation configuration.

As discussed, in some examples processing circuitry 120 may execute FFT techniques on impedance data 170 to identify FFT data 200A, 200B (collectively, "FFT data 200"). For example, FIG. 10A is a chart of example FFT data 200A created by processing circuitry 120 by executing FFT techniques on impedance data 170A (though it is to be understood that processing circuitry 120 may execute FFT techniques on other sets of impedance data in other examples). Processing circuitry 120 may identify FFT data 200A as indicating second non-fixation configuration 150B as described below. It is to be understood that FFT data 200A provided in FIG. 10A is provided for purposes of illustration only, as other systems may alter impedance values and similar systems may generate different impedance values depending upon medical conditions of patient 14. As depicted, processing circuitry 120 may only execute FFT techniques to identify FFT data 200A of impedance data 170 during second stage 174. Put differently, processing circuitry 120 may be configured to identify FFT data 200 that occurred while a clinician was executing a tug test. In other examples, processing circuitry 120 may identify more or less FFT data 200. For example, processing circuitry 120 may additionally identify FFT data 200 during first stage 172 which is subsequent to the deployment of IMD 16A but prior to the tug test.

Processing circuitry 120 may identify includes base frequency 202A and a plurality of harmonic frequencies 204A, 204B, 204C (collectively, "harmonic frequencies 204") of FFT data 200A. As discussed above, base frequency 202A may correspond to a heartbeat of patient 14. Processing circuitry 120 may determine that a ratio between one or more harmonic frequencies 204 and base frequency 202A does not satisfy FFT threshold 139. For example, FFT threshold 139 may include a ratio of 1:4 between base frequency 202A and a first harmonic (e.g., the harmonic frequency with the largest amplitude, which processing circuitry 120 may identify as harmonic frequency 204A). Processing circuitry 120 may identify that first harmonic frequency 204A has an amplitude that is larger than 25% of the amplitude of base frequency 202A as depicted in FIG. 10A, where first harmonic frequency 204A has an amplitude that is around 50% of base frequency 202A. In response to determining that first harmonic frequency 204A has an amplitude that is more than 25% the amplitude of base frequency 202A, processing circuitry 120 may cause indicating circuitry 128 to indicate second non-fixation configuration 150B on user interface 104 as described herein.

Additionally, or alternatively, FFT threshold 139 may include a ratio between an amplitude of base frequency 202A and a sum of a plurality of amplitudes of a plurality of harmonic frequencies 204, and processing circuitry 120 may identify if the ratio satisfies the FFT threshold 139. For example, FFT threshold 139 may include a 3:5 ratio between the amplitude of base frequency 202A and the sum of the amplitudes of the first three harmonic frequencies 204A, 204B, 204C. Processing circuitry 120 may identify that the sum of the amplitudes of the first three harmonic frequencies 204A, 204B, 204C is higher than 60% of the amplitude of base frequency 202A as depicted in FIG. 10A. In response to determining that the sum of the amplitudes of the first three harmonic frequencies 204A, 204B, 204C is greater than 60% of the amplitude of base frequency 202A, processing circuitry 120 may cause indicating circuitry 128 to indicate second non-fixation configuration 150B on user interface 104 as described herein.

Figure 10B:
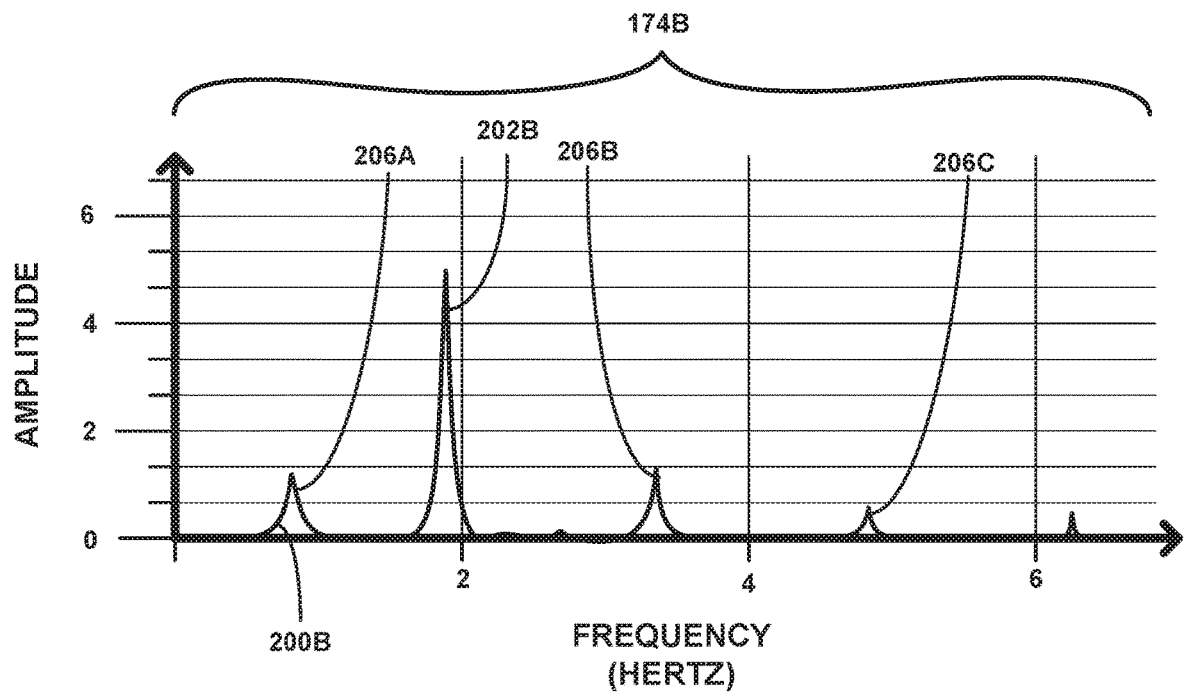
FIG. 10B is a chart of example FFT data that indicates a second fixation configuration.

Additionally, processing circuitry 120 may execute FFT techniques on impedance data 170 to determine that IMD 16A indicates second fixation configuration 152B. For example, FIG. 10B is a chart of example FFT data 200B created by processing circuitry 120 by executing FFT techniques on impedance data 170B (though it is to be understood that processing circuitry 120 may execute FFT techniques on other sets of impedance data in other examples as discussed above). As depicted, processing circuitry 120 may only execute FFT techniques to identify FFT data 200B of impedance data 170B during second stage 174B, though processing circuitry 120 may execute FFT techniques on other portions of impedance data 170 (e.g., such as during first stage 172 which is subsequent to the deployment of IMD 16A but prior to the tug test) in other examples.

Processing circuitry 120 may identify base frequency 202B and a plurality of harmonic frequencies 206A, 206B, 206C (collectively, "harmonic frequencies 206") of FFT data 200B. As discussed above, base frequency 202B may correspond to a heartbeat of patient 14. Processing circuitry 120 may determine that a ratio between one or more harmonic frequencies 206 and base frequency 202B satisfies FFT threshold 139. For example, FFT threshold 139 may include a ratio of 1:4 between base frequency 202B and a first harmonic (e.g., the harmonic frequency with the largest amplitude, which processing circuitry 120 may identify as harmonic frequency 206B). Processing circuitry 120 may identify that first harmonic frequency 206B has an amplitude that is smaller than 25% of the amplitude of base frequency 202B as depicted in FIG. 10B, where first harmonic frequency 206B has an amplitude that is around 20% of base frequency 202B. In response to determining that first harmonic frequency 206B has an amplitude that is less than 25% the amplitude of base frequency 202B, processing circuitry 120 may cause indicating circuitry 128 to indicate second fixation configuration 152B on user interface 104 as described herein.

Additionally, or alternatively, FFT threshold 139 may include a ratio between an amplitude of base frequency 202B and a sum of a plurality of amplitudes of a plurality of harmonic frequencies 206, and processing circuitry 120 may identify if the ratio satisfies the FFT threshold 139. For example, FFT threshold 139 may include a 1:2 ratio between the amplitude of base frequency 202B and the sum of the amplitudes of the first three harmonic frequencies 206A, 206B, 206C. Processing circuitry 120 may identify that the sum of the amplitudes of the first three harmonic frequencies 206A, 206B, 206C is lower than 50% of the amplitude of base frequency 202B as depicted in FIG. 10BA. In response to determining that the sum of the amplitudes of the first three harmonic frequencies 206A, 206B, 206C is lower than 50% of the amplitude of base frequency 202B, processing circuitry 120 may cause indicating circuitry 128 to indicate second fixation configuration 152B on user interface 104 as described herein.

Figure 11:
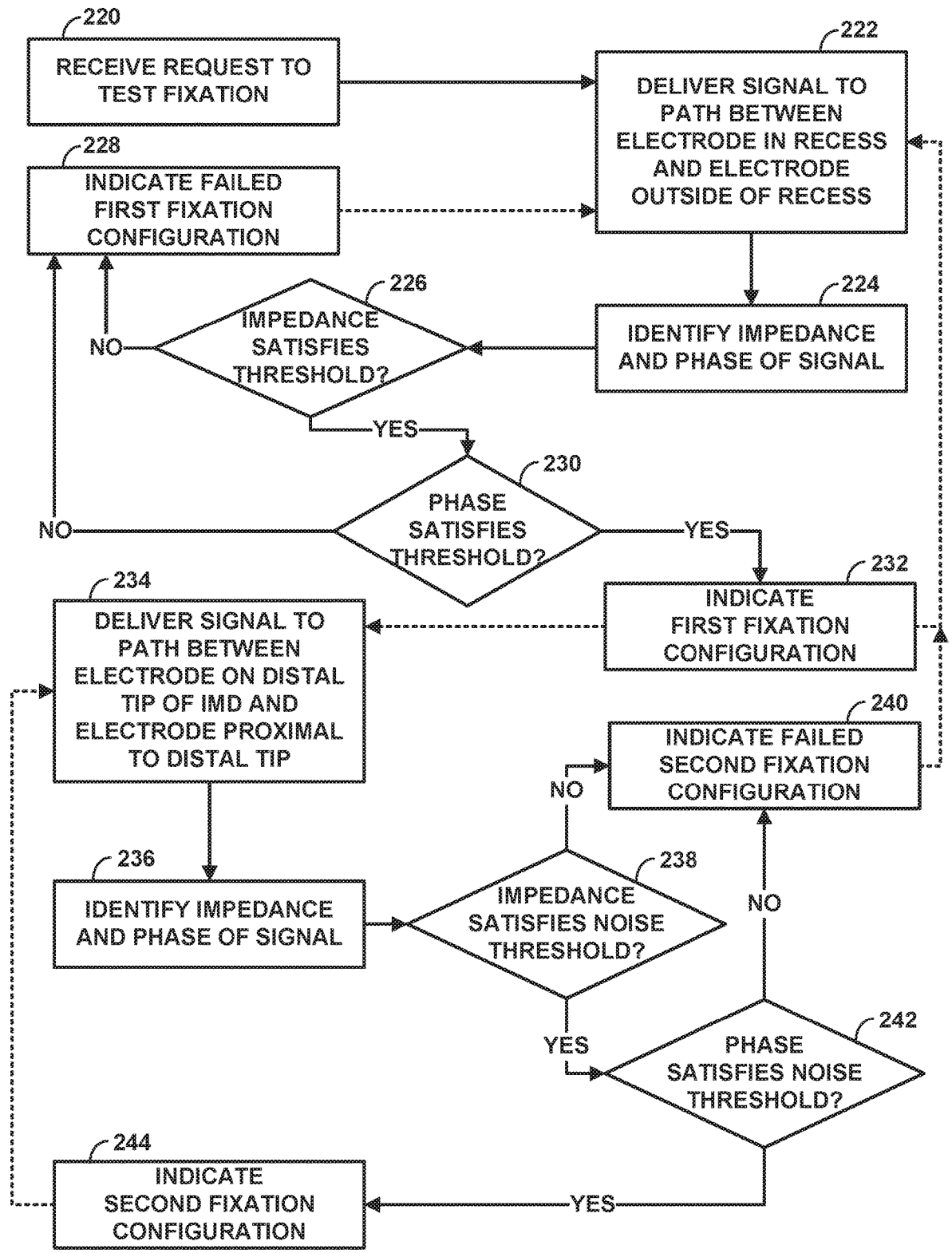
FIG. 11 depicts a flowchart of an example method of processing circuitry verifying that electrical signals indicate that a delivery device and IMD are defining one or more fixation configurations relative to a target site.

FIG. 11 depicts a flowchart of a method of delivering a medical device to a target site within a patient using a delivery device as described herein. FIG. 11 is discussed with reference to circuitry 94 of FIG. 3 as well as IMD 16A and delivery device 50 of FIG. 2A, but it is to be understood that the method of FIG. 11 may be completed using other delivery devices and circuitry described herein to deliver implantable medical devices in other examples. Processing circuitry 120 may receive a request to test fixation (220). This request may be received from a clinician accessing user interface 104. In some examples, processing circuitry 120 may receive this request using telemetry techniques.

Processing circuitry 120 may cause signal generation circuitry 124 to delivery an electrical signal to path 132 between first electrode 90 and second electrode 92 (222). Path 132 may include both tissue and fluid of patient 14. Signal generation circuitry 124 may deliver this electrical signal by providing a known (e.g., sinusoidal or pulse) voltage potential across electrodes 90, 92. Impedance detection circuitry 126 may detect impedance levels and processing circuitry 120 may identify a phase of the signal across electrodes 90, 92 on the impedance (224). Identifying phase across path 132 may include identifying an amount that the voltage lags or leads current across path 132. Processing circuitry 120 may verify whether or not this impedance satisfies (e.g., is over) impedance threshold 134 as stored in memory 122 (226). Where processing circuitry 120 determines that the impedance does not satisfy (e.g., is under) impedance threshold 134, processing circuitry 120 may cause indicating circuitry 128 to provide an indication on user interface 104 of first non-fixation configuration 150A (228). For example, where user interface 104 is an LED, indicating circuitry 128 may cause this LED to provide a red color. For another example, where user interface 104 is a screen of external device 18, indicating circuitry 128 may cause user interface 104 screen of external device 18 to display a failure message. In certain examples, processing circuitry 120 may cause signal generation circuitry 124, impedance detection circuitry 126, and indicating circuitry 128 to continue this logical loop until, e.g., processing circuitry 120 receives a message (from a clinician) to stop testing for the first fixation configuration.

Conversely, in response to processing circuitry 120 determining that the impedance satisfies (e.g., is over) impedance threshold 134, impedance detection circuitry 128 may additionally determine whether phase (as identified at 224) satisfies (e.g., is over) phase threshold 133 (230). Where processing circuitry 120 determines that the phase does not satisfy (e.g., is under) phase threshold 133, processing circuitry 120 may cause indicating circuitry 128 to provide an indication on user interface 104 of first non-fixation configuration 150A (228). Alternatively, when processing circuitry 120 determines that both impedance satisfies impedance threshold 134 and phase satisfies phase threshold 133, processing circuitry 120 may cause indicating circuitry 128 to indicate a successful first fixation configuration 152A (232). A successful first fixation configuration 152 may relate to distal opening 78 of deployment bay 52 of delivery device 50 that deploys IMD 16A being flush with a surface of tissue 142 and/or pressing into tissue 142 at target site 140. In some examples, indicating circuitry 128 may continue providing an indication of first fixation configuration 152A for as long as processing circuitry 120 continues detecting that an impedance of an electrical signal across path 132 is over impedance threshold 134 (which is to say that step 232 may naturally return to step 222 unless an affirmative input from a clinician is received that overrides this return).

In some examples, circuitry 94 may further test if IMD 16A defines second fixation configuration. In such examples, processing circuitry 120 may cause signal generation circuitry 124 to deliver an electrical signal to path 132 between first electrode 90 on distal tip 96 of IMD 16A and second electrode 92 (234). Impedance detection circuitry 126 may identify an impedance of this signal, with which processing circuitry 120 may identify the phase of the signal (236). For example, processing circuitry 120 may determine a phase of heart 12 by identifying an amount that voltage of the signal across path 132 leads or lags a current. Processing circuitry 120 may determine whether the impedance is noisy (238). Processing circuitry 120 may determine that the impedance of the signal is noisy if the impedance fails to satisfy slope threshold 136 or if the impedance includes bimodal signatures 137 as stored in memory 122. Where the impedance waveform fails to satisfy slope threshold 136 and/or includes bimodal signatures 137, processing circuitry 120 may cause indicating circuitry 128 to provide second non-fixation configuration 150B message to user interface 104 (240). In some examples, processing circuitry 120 may cause signal generation circuitry 124 to delivery an electrical signal to path 132 to test for first fixation configuration (222) in response to determining that impedance indicates second non-fixation configuration 150B.

Where the impedance waveform is stable such that the impedance waveform satisfies slope threshold 136 and does not define bimodal signatures 137, processing circuitry 120 may determine whether a phase (as identified in 236) satisfies phase threshold 138 (242). Processing circuitry 120 may determine that the phase does not satisfy phase threshold 138 as a result of peaks and valleys of phase being inconsistent, and/or as a result of phase include bimodal signatures 137. As a result of a phase of the electrical signal failing phase threshold 138, processing circuitry 120 may cause indicating circuitry 128 to provide second non-fixation configuration 150B message to user interface 104 (240). Similar to above, in some examples, processing circuitry 120 may cause signal generation circuitry 124 to delivery an electrical signal to path 132 to test for first fixation configuration (222) in response to determining that impedance indicates second non-fixation configuration 150B (e.g., in order for deployment bay 52 to be reoriented by tissue to redeploy IMD 16A).

If processing circuitry 120 determines that phase of the electrical signal satisfies phase threshold 138 and/or does not define bimodal signatures 137, processing circuitry 120 may cause indicating circuitry 128 to provide indication of second fixation configuration 152B (244). Second fixation configuration 152B may include IMD 16A being secured to tissue 142 according to a predetermined manner. For example, second fixation configuration 152B may include distal electrode 90 of IMD 16A pressing into tissue 142 securely and uniformly and with at least a threshold amount of force. In some examples, processing circuitry 120 may be configured to chronically determine whether IMD 16A defines second fixation configuration 152B. For example, as indicated in the flowchart of FIG. 11, processing circuitry 120 may cause signal generation circuitry 124 to continue sending an electrical signal across path 132 such that processing circuitry 120 may continually identify if IMD 16A continually defines second fixation configuration 152B. Processing circuitry 120 may be configured to thusly verify whether or not IMD 16A defines second fixation configuration 152B on a regular schedule, such as once an hour, once a day, once a week, or the like. Processing circuitry 120 may be configured to cause indicating circuitry 128 to send a message (e.g., to external device 18) if IMD 16A is still defining second fixation configuration 152B, or whether IMD 16A has shifted such IMD 16A has started defining second non-fixation configuration 150B.

Figure 12:
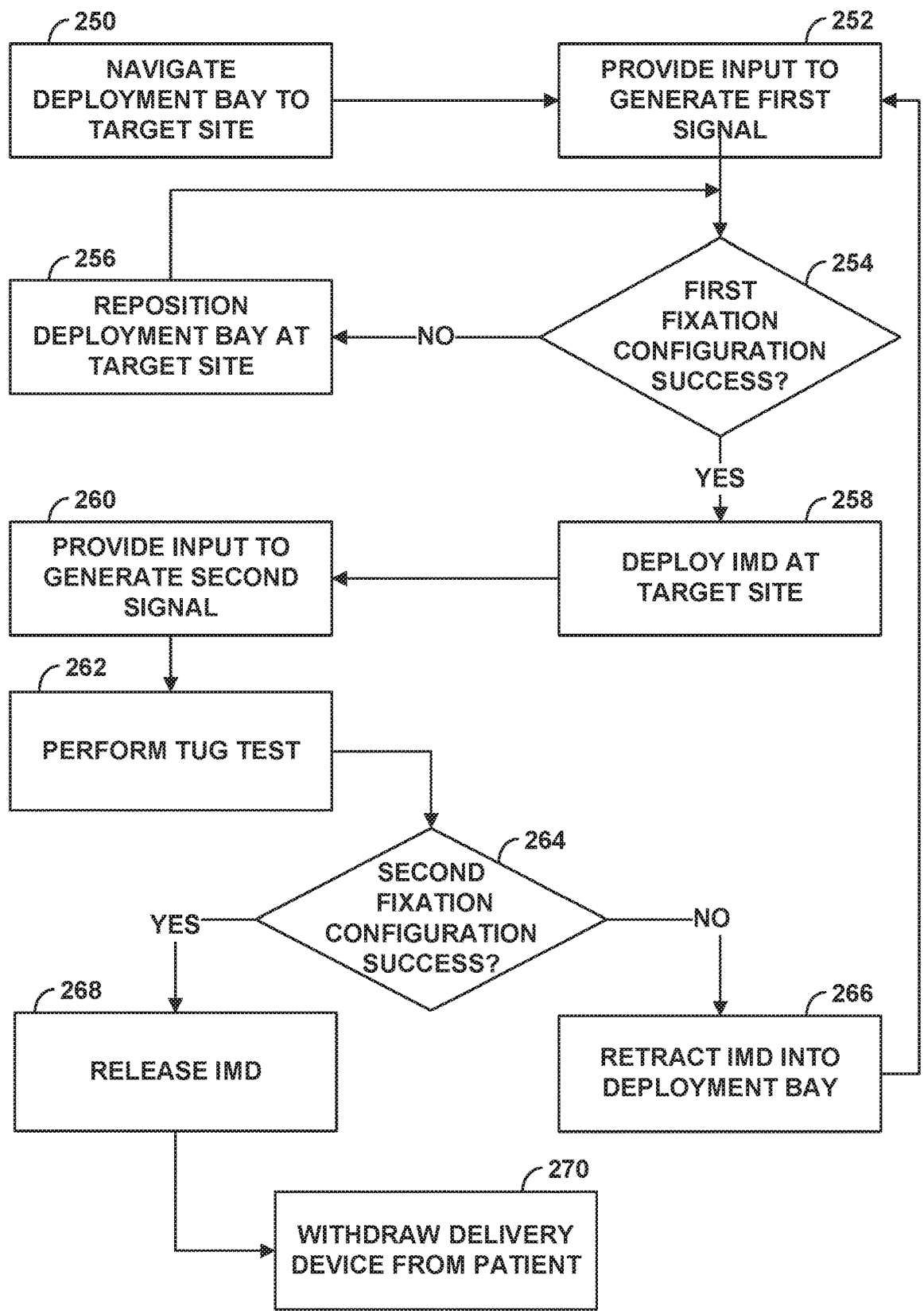
FIG. 12 depicts a flowchart of an example method of a clinician deploying an IMD to a target site while verifying that a delivery device and IMD are defining one or more fixation configurations relative to the target site.

FIG. 12 depicts a flowchart of a method of delivering a medical device to a target site within a patient using a delivery device as described herein. FIG. 12 is discussed with reference to delivery device 50 of FIGS. 2A-7 as well as IMD 16A of FIG. 1A, but it is to be understood that the method of FIG. 12 may be completed using the other delivery device described herein to delivery any insertable or implantable medical device in other examples. A clinician may navigate delivery device 50 to target site 140 within patient 14 (250). For example, a clinician may navigate deployment bay 52 of delivery device 50 to right atrium 20 of heart 12 of patient 14 (as depicted in FIG. 1A). The clinician may navigate delivery device 50 to target site 140 after inserting delivery device 50 into an introducer sheath inserted into patient 14. The clinician may navigate delivery device 50 to target site 140 using one or more deflection members 102 as deflected using a steering or deflecting mechanism of hub 56. Once the clinician has navigated deployment bay 52 to target site 140, the clinician may press deployment bay 52 against the target site 140. The clinician may use radiopaque elements of delivery device 50 (e.g., such as electrodes 90, 92) to navigate the deployment bay 52 to target site 140 using fluoroscopy techniques.

Once the clinician has arranged the deployment bay 52 at the target site 140, the clinician may provide an input to generate a first signal across a path between first electrode 90 within recess 74 of deployment bay 52 and second electrode 90 outside of recess 74 of deployment bay 52 (252). The clinician may check to see whether or not circuitry 94 indicates that deployment bay 52 defines first fixation configuration 152A (254). The clinician may use user interface 104 to determine whether or not circuitry 94 indicates that deployment bay 52 defines first fixation configuration 152A. Where the user interface 104 does not indicate first fixation configuration 152A (e.g., but instead indicates first non-fixation configuration 150A), the clinician may reposition deployment bay 52 at target site 140 (256).

Once the clinician sees (as indicated by user interface 104) that circuitry 94 indicates that deployment bay 52 defines first fixation configuration 152A, the clinician may deploy IMD 16A at target site 140 (258). Deploying IMD 16A may include using deployment mechanism 66 to distally push IMD 16A relative to deployment bay 52 until fixation means 82 engage tissue 142. Once IMD 16A is deployed, the clinician provides an input to circuitry 94 to provide an input to generate a second signal to path 132 between first electrode 90 on distal tip 96 of IMD 16A and second electrode 92 that is proximal to distal tip 96 (260). The clinician may provide the input to generate the second signal in the same manner as the clinician provided the input for the first signal. Upon providing the input, the clinician may execute a tug test on IMD 16A (262). For example, the clinician may tug on tether 262 of delivery device 50 subsequent to providing the input to circuitry 94 to generate the second signal and therein verify a fixation of IMD 16A.

The clinician may determine whether IMD 16A defines second fixation configuration 152B (264). For example, the clinician may use user interface 104 to see if circuitry 94 indicates that IMD 16A defines second fixation configuration 152B. Where circuitry 94 indicates that IMD 16B does not define second fixation configuration 152B (e.g., but instead defines second non-fixation configuration 150B), the clinician may retract IMD 16A into deployment bay 52 (266). For example, the clinician may use tether 162 as engaged with proximal catch 114 of IMD 16A to retract IMD 16A into deployment bay 52. In some examples, in response to retracting IMD 16A, the clinician may look to reposition deployment bay 52 into first fixation configuration 152A by providing an input to generate the first signal again (252).

In other examples, the clinician may identify that user interface 104 indicates that IMD 16A defines second fixation configuration 152B. Where the clinician identifies that circuitry 94 indicates that IMD 16A defines second fixation configuration 152B, the clinician may release IMD 16A (e.g., by cutting tether 162) (268). Once IMD 16A is deployed and fully release, the clinician may retract delivery device 50 out of patient 14 (270). The clinician may withdraw delivery device 50 out of introducer sheath through which delivery device 50 was inserted.

This disclosure is primary directed to medical delivery devices that use an impedance between electrodes to verify when deployment bays that contain implantable devices and/or the devices themselves define various fixation configurations that indicate that the implantable devices either are aligned to be or are currently properly secured to a target site in a heart. However, one or more aspects of this disclosure may also be applicable to delivering other insertable or implantable medical devices to other areas of a patient. For one example, as discussed herein, aspects of this disclosure may be applicable to delivering a lead that includes distal fixation elements to a target site within a patient. Further, aspects of this disclosure may be applicable to delivering a lead to a spinal cord or another organ of a patient. Other applications for aspects of this disclosure would also be understood by one of ordinary skill in the art.

Various examples have been described. These and other examples are within the scope of the following claims.

The invention claimed is:

1. An implantable medical device delivery system comprising:
  an elongated member configured to navigate an intravascular system of a patient;
  a deployment bay connected to a distal portion of the elongated member and configured to house at least a portion of an implantable medical device (IMD), the deployment bay defining a distal opening configured for deployment of the IMD out of the deployment bay at a target site in a patient;
  signal generation circuitry configured to deliver an electrical signal to a path between a first electrode located inside of the deployment bay and a second electrode through at least one of a fluid or a tissue of the patient; and
  processing circuitry configured to:
    determine an impedance of the path based on the electrical signal;
    determine that the impedance of the path satisfies an impedance threshold, the impedance threshold corresponding to tissue of the patient being in the path; and
    generate an output via a user interface indicating that at least one of the IMD or the distal opening is in a fixation configuration relative to the target site of the patient based on the satisfied impedance threshold.

2. The medical delivery system of claim 1, wherein the fixation configuration includes a first fixation configuration wherein the distal opening of the deployment bay is substantially flush against a tissue of the target site.

3. The medical delivery system of claim 2, wherein the deployment bay is pressed against the tissue with a threshold amount of force in the first fixation configuration.

4. The medical delivery system of claim 2, further comprising the IMD, wherein the first and second electrodes are first and second electrodes of the IMD.

5. The medical delivery system of claim 4, wherein the deployment bay defines one or more holes that extend radially in through the deployment bay to expose the second electrode to fluids of the patient.

6. The medical delivery system of claim 5, further comprising one or more ribs that extend radially in from an inner surface of the deployment bay to engage the housing of the IMD, wherein the one or more holes extend radially in through the one or more ribs.

7. The medical delivery system of claim 2, wherein the first electrode is secured to an inner surface of the deployment bay.

8. The medical delivery system of claim 2, wherein the second electrode is secured to an outer surface of the deployment bay or an outer surface of the elongated member.

9. The medical delivery system of claim 1, further comprising the IMD, wherein the first and second electrodes are first and second electrodes of the IMD and the IMD comprises one or more fixation elements, and wherein the fixation configuration includes a second fixation configuration wherein a threshold amount of the one or more fixation elements of the IMD are secured to the tissue of the target site.

10. The medical delivery system of claim 1, wherein the user interface comprises a display of an external device, the system further comprising telemetry circuitry, wherein the processing circuitry is configured to use the telemetry circuitry to cause the display of the external device to indicate when the impedance threshold corresponds to at least one of the IMD or the distal opening in the fixation configuration relative to the target site of the patient.

11. The medical delivery system of claim 1, wherein the user interface is located adjacent a proximal portion of the elongated member and is electrically coupled to the processing circuitry.

12. The medical delivery system of claim 1, wherein the target site is a wall of an atrium of the patient.

13. A system for using an implantable medical device delivery system to deliver an implantable medical device to tissue of a patient, the system comprising:
    signal generation circuitry configured to deliver an electrical signal to a path between a first electrode and a second electrode through at least one of a fluid or the tissue of the patient; and
    processing circuitry configured to:
        determine an impedance of the path based on the electrical signal;
        determine whether the impedance of the path satisfies an impedance threshold, the impedance threshold corresponding to at least one of a first fixation configuration where a distal portion of the implantable medical device delivery system is substantially flush with the tissue of the patient or a second fixation configuration where one or more fixation elements of the implantable medical device satisfy a fixation threshold to the tissue of the patient; and
        provide an indication when the satisfied impedance threshold corresponds to at least one of the first fixation configuration or the second fixation configuration.

14. The system of claim 13, where the processing circuitry is configured to determine that the impedance threshold corresponds to the first fixation configuration when the impedance of the path is over a threshold impedance.

15. The system of claim 13, where the processing circuitry is configured to determine that the impedance threshold corresponds to the first fixation configuration by identifying that a phase waveform is above a threshold.

16. The system of claim 13, wherein the processing circuitry is configured to determine if the impedance threshold corresponds to at least one of the first or second fixation configuration by at least determining a first derivative amplitude of the impedance of the path.

17. The system of claim 13, wherein the processing circuitry is configured to determine whether the impedance threshold corresponds to a second fixation configuration by being configured to:
    determine an amount of noise of a waveform of the impedance of the path; and
    determine whether the amount of noise satisfies a noise threshold.

18. The system of claim 17, wherein the noise includes bimodal signatures and the processing circuitry is configured to determine that the waveform of the impedance of the path indicates the second fixation configuration based on identification of the bimodal signatures.

19. The system of claim 18, wherein the processing circuitry is configured to determine the amount of noise by at least identifying frequency components of the signal.

20. The system of claim 13, wherein the system is integrated into the implantable medical device delivery system.

21. The system of claim 13, wherein the system is integrated into the implantable medical device.

22. An implantable medical device (IMD) comprising:
    a housing configured to be secured to a target site in a patient via one or more fixation elements extending distally from a distal tip of the housing;
    a first electrode secured to the distal tip of the housing;
    a second electrode secured to an outer surface of a proximal portion of the housing;
    signal generation circuitry configured to deliver an electrical signal to a path between the first electrode and the second electrode through at least one of a fluid or a tissue of the patient; and
    processing circuitry configured to:
        determine an impedance of the path based on the electrical signal;
        determine that the impedance of the path satisfies an impedance threshold, the impedance threshold corresponding to tissue of the patient is in the path; and
        generate an output via a user interface indicating that the IMD is in a fixation configuration relative to the target site of the patient based on the satisfied impedance threshold.

23. The IMD of claim 22, wherein:
    the fixation configuration includes a threshold number of the fixation elements of the IMD being secured to the tissue of the target site;
    the processing circuitry is configured to determine an amount of noise of a waveform of the impedance of the path and determine whether the impedance threshold corresponds to the IMD in the fixation configuration based on the amount of noise.

24. The IMD of claim 23, wherein the noise includes bimodal signatures and the processing circuitry is configured to determine that the impedance threshold corresponds to the IMD being in the fixation configuration when the waveform does not define the bimodal signatures.

25. The IMD of claim 23, wherein the processing circuitry is configured to determine the amount of noise by at least one of:
    identifying frequency components above a threshold; or
    decomposition of the impedance signal via frequency components.

26. The IMD of claim 22, wherein the IMD is a leadless pacemaker.

27. The IMD of claim 22, wherein the one or more fixation elements comprise one or more fixation tines.

28. The IMD of claim 22, further comprising telemetry circuitry, wherein the processing circuitry generates the output via the telemetry circuitry.

\* \* \* \* \*